United States Patent
Vyavahare et al.

(10) Patent No.: US 12,371,479 B2
(45) Date of Patent: Jul. 29, 2025

(54) ANTI-ELASTIN ANTIBODIES AND METHODS OF USE

(71) Applicant: CLEMSON UNIVERSITY RESEARCH FOUNDATION, Clemson, SC (US)

(72) Inventors: Narendra R. Vyavahare, Clemson, SC (US); Charles D. Rice, Clemson, SC (US); Nasim Nosoudi, Clemson, SC (US); Saketh Karamched, Clemson, SC (US); Vaideesh Parasaram, Clemson, SC (US)

(73) Assignee: CLEMSON UNIVERSITY RESEARCH FOUNDATION, Clemson, SC (US)

( * ) Notice: Subject to any disclaimer, the term of this patent is extended or adjusted under 35 U.S.C. 154(b) by 988 days.

(21) Appl. No.: 17/423,999

(22) PCT Filed: Jan. 22, 2019

(86) PCT No.: PCT/US2019/014537
§ 371 (c)(1),
(2) Date: Jul. 19, 2021

(87) PCT Pub. No.: WO2020/153940
PCT Pub. Date: Jul. 30, 2020

(65) Prior Publication Data
US 2022/0089706 A1  Mar. 24, 2022

(51) Int. Cl.
| | |
|---|---|
| *A61K 39/395* | (2006.01) |
| *A61K 47/68* | (2017.01) |
| *A61K 49/00* | (2006.01) |
| *C07K 14/78* | (2006.01) |
| *C07K 16/18* | (2006.01) |
| *G01N 33/53* | (2006.01) |
| *G01N 33/68* | (2006.01) |
| *A61K 39/00* | (2006.01) |

(52) U.S. Cl.
CPC .......... *C07K 16/18* (2013.01); *A61K 39/3955* (2013.01); *A61K 47/6843* (2017.08); *A61K 49/0058* (2013.01); *C07K 14/78* (2013.01); *G01N 33/53* (2013.01); *G01N 33/6887* (2013.01); *A61K 2039/505* (2013.01); *G01N 2333/78* (2013.01)

(58) Field of Classification Search
CPC ............ A61K 2039/505; A61K 39/395; A61K 39/3955; A61K 38/39; C07K 14/78; C07K 16/18; G01N 33/53; G01N 33/6887; G01N 2333/78

See application file for complete search history.

(56) References Cited

U.S. PATENT DOCUMENTS

| | | |
|---|---|---|
| 3,918,455 A | 11/1975 | Coplan |
| 3,997,396 A | 12/1976 | Delente |
| 4,027,676 A | 6/1977 | Mattei |
| 5,123,912 A | 6/1992 | Kaplan et al. |
| 5,162,225 A | 11/1992 | Sager et al. |
| 5,200,248 A | 4/1993 | Thompson et al. |
| 5,242,644 A | 9/1993 | Thompson et al. |
| 5,263,984 A | 11/1993 | Li et al. |
| 5,268,229 A | 12/1993 | Phillips et al. |
| 5,496,627 A | 3/1996 | Bagrodia et al. |
| 5,512,600 A | 4/1996 | Mikos et al. |
| 5,518,680 A | 5/1996 | Cima et al. |
| 5,611,981 A | 3/1997 | Phillips et al. |
| 5,716,404 A | 2/1998 | Vacanti et al. |
| 5,723,159 A | 3/1998 | Phillips et al. |
| 5,759,830 A | 6/1998 | Vacanti et al. |
| 5,770,193 A | 6/1998 | Vacanti et al. |
| 5,804,318 A | 9/1998 | Pinchuk et al. |
| 5,906,828 A | 5/1999 | Cima et al. |
| 5,942,436 A | 8/1999 | Dunn et al. |
| 5,972,505 A | 10/1999 | Phillips et al. |
| 6,303,136 B1 | 10/2001 | Li et al. |
| 6,306,424 B1 | 10/2001 | Vyakarnam et al. |
| 6,333,029 B1 | 12/2001 | Vyakarnam et al. |
| 6,365,149 B2 | 4/2002 | Vyakarnam et al. |

(Continued)

FOREIGN PATENT DOCUMENTS

| | | |
|---|---|---|
| JP | 2011-503564 | 1/2011 |
| WO | WO 00/47716 | 8/2000 |

(Continued)

OTHER PUBLICATIONS

Casset et al. A peptide mimetic of an anti-CD4 monoclonal antibody by rational design. Biochem Biophys Res Comm 307: 198-205, 2003.*
Chen et al. Selection and analysis of an optimized anti-VEGF antibody: crystal structure of an affinity-matured Fab in complex with antigen. J Mol Biol 293: 865-881, 1999.*
De Pascalis et al. Grafting of "abbreviated" complementarity-determining regions containing specificity-determining residues essential for ligand contact to engineer a less immunogenic humanized monoclonal antibody. J Immunol 169: 3076-3084, 2002.*
Holm et al. Functional mapping and single chain construction of the anti-cytokeratin 8 monoclonal antibody TS1. Mol Immunol 44: 1075-1084, 2007.*

(Continued)

*Primary Examiner* — Bridget E Bunner
(74) *Attorney, Agent, or Firm* — DORITY & MANNING, P.A.

(57) ABSTRACT

Antibodies and antigen binding fragments thereof that specifically recognize and bind an epitope of elastin that is exposed and accessible in degraded elastic fiber are described. The antibodies and/or antigen binding fragments can be operably linked to a secondary component, including biologically active agents such as therapeutics and/or imaging agents. Optionally, the antibodies and/or antigen binding fragments thereof can be attached to a surface of a carrier, such as a particle, for specific binding and delivery of the carried agents to degraded elastic fiber.

20 Claims, 27 Drawing Sheets

Specification includes a Sequence Listing.

(56) References Cited

U.S. PATENT DOCUMENTS

| | | |
|---|---|---|
| 6,368,859 B1 | 4/2002 | Atala |
| 6,391,538 B1 | 5/2002 | Vyavahare et al. |
| 6,468,649 B1 | 10/2002 | Zhong |
| 6,521,431 B1 | 2/2003 | Kiser et al. |
| 6,544,548 B1 | 4/2003 | Siller-Jackson et al. |
| 6,753,311 B2 | 6/2004 | Fertala et al. |
| 6,790,455 B2 | 9/2004 | Chu et al. |
| 6,858,222 B2 | 2/2005 | Nelson et al. |
| 6,861,142 B1 | 3/2005 | Wilkie et al. |
| 6,861,211 B2 | 3/2005 | Levy et al. |
| 7,056,580 B2 | 6/2006 | Dugan |
| 7,374,673 B2 | 5/2008 | Marcus |
| 7,479,164 B2 | 1/2009 | Girardot et al. |
| 7,713,543 B2 | 5/2010 | Vyavahare et al. |
| 7,918,899 B2 | 4/2011 | Girardot et al. |
| 8,926,974 B2 * | 1/2015 | Griswold-Prenner ...................... A61K 47/60 514/17.7 |
| 9,795,573 B2 | 10/2017 | Vyavahare et al. |
| 10,112,990 B2 * | 10/2018 | Adolfsson .............. C07K 16/18 |
| 10,688,061 B2 | 6/2020 | Vyavahare et al. |
| 2001/0033857 A1 | 10/2001 | Vyakarnam et al. |
| 2002/0022883 A1 | 2/2002 | Burg |
| 2005/0070930 A1 | 3/2005 | Kammerer |
| 2009/0104215 A1 | 4/2009 | Ekiel et al. |
| 2011/0129531 A1 | 6/2011 | Collette et al. |
| 2012/0045781 A1 | 2/2012 | Veidal et al. |
| 2014/0017263 A1 | 1/2014 | Vyavahare et al. |
| 2014/0086921 A1 | 3/2014 | Griswold-Prenner et al. |
| 2014/0193420 A1 | 7/2014 | Aburatani et al. |
| 2015/0087611 A1 | 3/2015 | Vyavahare et al. |
| 2015/0344548 A1 | 12/2015 | Simard |
| 2017/0002047 A1 | 1/2017 | Jimenez et al. |
| 2017/0015742 A1 | 1/2017 | Gu et al. |
| 2017/0209592 A1 | 7/2017 | Vyavahare et al. |
| 2017/0275376 A1 | 9/2017 | Igawa et al. |
| 2018/0036261 A1 | 2/2018 | Vyavahare et al. |
| 2020/0276131 A1 | 9/2020 | Vyavahare et al. |

FOREIGN PATENT DOCUMENTS

| | | |
|---|---|---|
| WO | WO 2006/115733 | 11/2006 |
| WO | WO 2015/104342 A1 | 7/2015 |

OTHER PUBLICATIONS

Lei et al. Targeted chelation therapy with EDTA-loaded albumin nanoparticles regresses arterial calcification without causing systemic side effects. J Controlled Release 196: 79-86, 2014.*

MacCallum et al. Antibody-antigen interactions: contact analysis and binding site topography. J Mol Biol 262: 732-745, 1996.*

Targeted drug delivery to emphysematous lungs: Inhibition of MMPs by doxycycline loaded nanoparticles. Pulmon Pharmacol Therpeutics 39: 64-73, 2016.*

Paul, William E., Fundamental Immunology, 3rd Edition, Raven Press, New York, Chapt. 8, pp. 292-295 (1993).*

Rudikoff et al. Single amino acid substitution altering antigen-binding specificity. Proc Natl Acad Sci USA 79: 1979-1983, 1982.*

Zhang et al. Comprehensive optimization of a single-chain variable domain antibody fragment as a targeting ligand for a cytotoxic nanoparticle. mAbs 7(1): 42-52, 2015 (published online Nov. 21, 2014).*

Bunge, M.B. "Bridging Areas of Injury in the Spinal Cord" *Neuroscientist* 7 (2001) pp. 325-339.

Conroy, et al. "Lubricious coatings for medical devices" *dds&s* 3 (2004) pp. 89-92.

Cruise, et al. "Characterization of permeability and network structure of interfacially photopolymerized poly(ethylene glycol) diacrylate hydrogels" *Biomaterials* 19 (1998) pp. 1287-1294.

Harris, et al. "Assessment of the cytocompatibility of different coated titanium surfaces to fibroblasts and osteoblasts" *J. Biomed. Mater. Res. A* 73 (2005) pp. 12-20.

ISA. "International Search Report and Written Opinion" PCT/US2019/014537 (May 7, 2019) pp. 1-12.

Park, J.B. "Biomaterials: An Introduction" *Springer* (1992) pp. 230-231.

Ratner, et al. "Biomaterials Science: An Introduction to Materials in Medicine" *Academic Press* (1996) pp. 170-173.

Sawhney, et al. "Bioerodible Hydrogels Based on Photopolymerized Poly(ethylene glycol)-co-poly(α-hydroxy acid) Diacrylate Macromers" *Macromolecules* 26 (1993) pp. 581-587.

Wei, et al. "Epitope specificity of monoclonal and polyclonal antibodies to human elastin" *Int'l Arch. Allergy Immunol.* 115 (1998) pp. 33-41.

Yeo, et al. "Tropoelastin bridge region positions the cell-interactive C terminus and contributes to elastic fiber assembly" *PNAS* 109 (2012) pp. 2878-2883.

Binder et al. "Half-Life Extension of Therapeutic Proteins via Genetic Fusion to Recombinant PEG Mimetics" Therapeutic Proteins: Strategies to Modulate Their Plasma Half-Lives pp. 63-80, 2012.

Fiedler et al. "Non-Antibody Scaffolds as Alternative Therapeutic Agents" Handbook of Therapeutic Antibodies, Second Edition 2014 pp. 435-474.

Urban et al. "Cytochrome P450 (Cyp) mutants and substrate-specificity alterations: segment-directed mutagenesis applied to human CYP1A1" Biochemical Society: Protein Engineering of Peroxidases and Cytochrome P450 2001 pp. 128-135.

Barroso et al., "Study of human lung elastin degradation by different elastases using high-performance liquid chromatography/mass spectrometry", Analytical Biochemistry, vol. 358, 2006, pp. 216-224.

Kristensen et al., "Serological assessment of neutrophil elastase activity on elastin during lung ECM remodeling", BMC Pulmonary Medicine, 2015, 7 pages, 15:53.

Skjot-Arkil et al., "Acute Myocardial Infarction and Pulmonary Diseases Result in Two Different Degradation Profiles of Elastin as Quantified by Two Novel ELISAs", PLOS One, vol. 8, Issue 6, Jun. 2013, 11 pages, e60936.

Supplementary European Search Report, dated Sep. 6, 2022, 3 pages, for EP 19911987.

Office Action from JP, Mailed on Mar. 6, 2024, 4 pages.

* cited by examiner

ANTI-ELASTIN ANTIBODIES AND METHODS OF USE

SEQUENCE LISTING

This application contains a Sequence Listing which has been submitted electronically in ASCII format and is hereby incorporated by reference in its entirety. Said ASCII copy, created on Feb. 22, 2019, is named CXU-985-PCT-US_Sequence List.txt and is 21,942 bytes in size.

BACKGROUND

Elastin is the protein constituent of elastic fibers found in most connective tissue and throughout the body. Elastic fibers include an insoluble core of amorphous elastin that is surrounded and supported by a mantle of microfibrils, which are formed from a variety of different proteins, glycoproteins and the elastin receptor complex. The amorphous elastin core of the elastic fibers is formed upon deposition and integration of soluble tropoelastin monomers into the microfibril scaffold followed by crosslinking of the monomers to form the insoluble fibrous polymer.

Degradation of elastic fibers is a common feature of many pathologies, including aneurysms (e.g., abdominal aortic aneurysm, brain aneurysm), chronic obstructive pulmonary disease (COPD), chronic kidney disease, hypertension, $\alpha$-1 antitrypsin deficiency, Marfan's syndrome, atherosclerosis, arteriosclerosis, and others, as well as aging (i.e., loss of firmness/smoothness of skin over time). Elastic fiber degradation is often caused by enzymes including elastase enzymes, cathepsins, and matrix metalloproteinase (MMP) enzymes that can attack either or both of the elastin and the scaffolding components of elastic fiber. Such enzymes can be secreted by native cells including vascular cells in arteries, dermal and lung fibroblasts in skin and lung, respectively, as well as by infiltrating inflammatory cells in a variety of different disease states.

Unfortunately, systemic delivery is still the most common delivery method of therapeutic and diagnostic compounds in the above-mentioned pathologies, as well as others. Agents introduced systemically are typically filtered by the body via first-pass effect and other mechanisms. Thus, systemic delivery methods often require large doses of the compounds, which, in addition to adding to costs, can also cause unnecessary and/or toxic side effects to the patient. For example, systemic and/or generic delivery of agents can have off-target effects—interactions with non-targeted structures in the body—which can alter normal tissue- and/or organ-level function and lead to deleterious side effects.

What are needed in the art are anti-elastin antibodies that can be used as targeting agents and that can be delivered in conjunction with a biologically active agent for targeted delivery of the agent for therapeutic or diagnostic purposes.

SUMMARY

According to one embodiment, disclosed is an anti-elastin antibody or antigen binding portion thereof that specifically recognizes and binds an epitope elastin, and in particular, binds an epitope of one of SEQ ID NO.: 1, SEQ ID NO: 2, or SEQ ID NO.: 3. For instance, an anti-elastin antibody or an antigen binding fragment as disclosed can include one or more CDR fragments selected from SEQ ID NOs: 9, 11, 13, 27, 29, or 31.

Also disclosed are compositions that include an anti-elastin antibody or antigen binding portion thereof as described. For instance, a composition can include the anti-elastin antibody or antigen binding portion thereof (e.g., an entire antibody or a fragment thereof including one or more CDR fragments selected from SEQ ID NOs: 9, 11, 13, 27, 29, or 31) directly or indirectly attached to an agent, e.g., a biologically active agent such as a therapeutic agent, or a diagnostic agent such as a detectable marker. Compositions can include a particle associated with an active agent (e.g., a therapeutic) and an anti-elastin antibody or antigen binding fragment thereof attached to an exterior surface of the particle such that upon binding with its antigen, the antibody or fragment thereof can anchor the particle to an elastic fiber.

Methods for using the antibodies are also described. For instance, a method of use can include contacting a degraded elastic fiber with an antibody or antigen binding fragment thereof as described that is operably linked to an agent, for instance a therapeutic and/or an imaging agent, optionally linked to a particle or other delivery mechanism. The therapeutic can be any therapeutic for use in the general area of the degraded elastic fiber. For instance, it can be for use in directly treating the connective tissue that contains the elastic fiber or it can be for another use, e.g., a condition indirectly related to the existence of the degraded elastic fiber or even unrelated to the existence of the degraded elastic fiber, but including targeted components (e.g., tissue) in the general area of the degraded elastic fiber.

Also disclosed are materials and methods for production of disclosed antibodies and/or an antigen-binding portion thereof. For instance, methods for forming a hybridoma cell that produces disclosed monoclonal anti-elastin antibodies and the hybridomas thus formed are disclosed as well as genetically modified cells, vectors, etc. that include one or more nucleic acid sequences encoding an anti-elastin antibody or antigen binding portion thereof, e.g., one or more CDR encoding segments selected from SEQ ID NOs: 8, 10, 12, 26, 28, or 30.

BRIEF DESCRIPTION OF THE DRAWINGS

A full and enabling disclosure, including the best mode thereof, to one of ordinary skill in the art, is set forth more particularly in the remainder of the specification, including reference to the accompanying Figures, in which.

DETAILED DESCRIPTION

Figure 1:
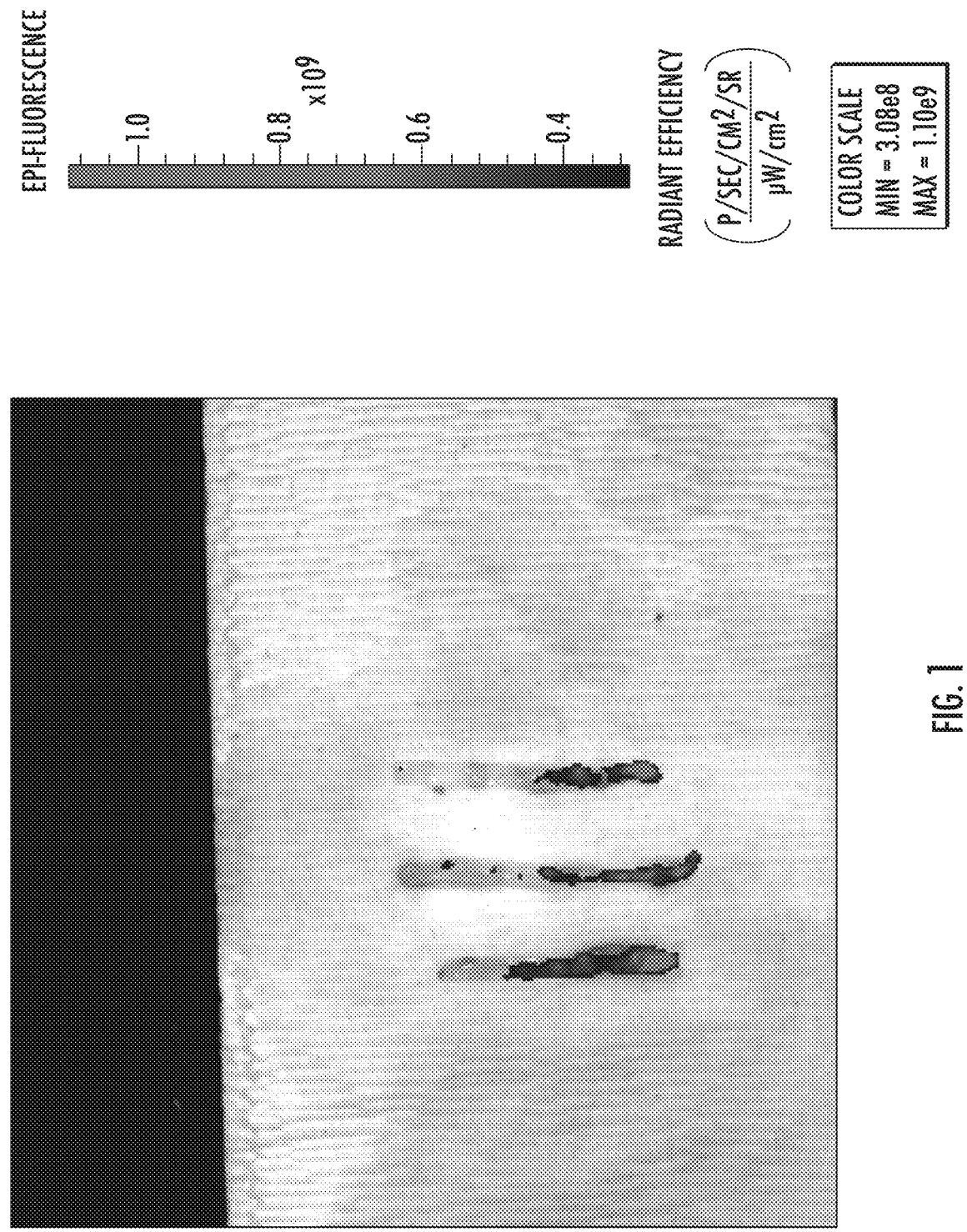
FIG. 1 illustrates rat aortae, a portion of each of which having been treated with elastase, following incubation with nanoparticles tagged with disclosed antibodies.

Reference will now be made in detail to various embodiments of the presently disclosed subject matter, one or more examples of which are set forth below. Each embodiment is provided by way of explanation, not limitation, of the subject matter. In fact, it will be apparent to those skilled in the art that various modifications and variations may be made to the present disclosure without departing from the scope or spirit of the disclosure. For instance, features illustrated or described as part of one embodiment, may be used in another embodiment to yield a still further embodiment. Thus, it is intended that the present disclosure cover such modifications and variations as come within the scope of the appended claims and their equivalents.

The present disclosure is generally directed to anti-elastin antibodies and antigen binding fragments thereof that can specifically bind an epitope of elastin. More specifically, disclosed is an isolated antibody or antigen binding fragment that is specific for rat, mice, pig, horse, dog, and human, as well as other forms of amorphous, crosslinked elastin. In particular, the disclosed antibodies and antigen binding fragments specifically recognize and bind an epitope sequence of one or more of GALGPGGKPPKPGAGLL (SEQ ID NO: 1), LGYPIKAPKLPGGYGLPY-TTGKLPYGYPGGVAGAAGKAGYPTTGTGV (SEQ ID NO: 2), or PGGYGLPYTTGKLPYGYP (SEQ ID NO: 3). Also disclosed are delivery agents that can incorporate the anti-elastin antibodies and antigen binding fragments thereof as targeting agents for delivery of biologically active agents to an area that includes elastin.

The epitope sequences exemplified by SEQ ID NOs: 1-3 are polypeptide components of the amorphous, crosslinked elastin component of an elastic fiber that can become exposed and accessible upon degradation of the elastic fiber, and in particular, upon degradation of the microfibril scaffolding structures of elastic fibers. As such, in one embodiment, the disclosed targeting agents can be utilized to bind to damaged elastic fibers and can exhibit little or no binding to healthy elastic fibers or soluble elastin precursors or break-down components as may circulate in the blood. For instance, a targeting agent that includes an antibody or antigen binding fragment(s) thereof that specifically recognizes and binds one or more of SEQ ID NOs: 1-3 can exhibit little or no binding to alpha-elastin degradation products. In one embodiment, targeting agents can bind immature elastin that is no longer soluble but that is not fully crosslinked and formed as elastic fibers, e.g., immature elastin in atherosclerotic fibrous caps.

The disclosed antibodies/fragments encompass immunoglobulin molecules and immunologically active portions of immunoglobulin molecules (i.e., molecules that contain an antigen binding site that immuno-specifically bind one or more of the polypeptides described herein). A complete antibody can generally be comprised of two immunoglobulin heavy chains and two immunoglobulin light chains. In one particular embodiment, an antibody as disclosed herein can include as heavy chain SEQ ID NO: 5 and as light chain SEQ ID NO: 23. However, it should be understood that the invention encompasses complete antibodies that include the variable portions of the disclosed antibodies (SEQ ID NO: 7 ($V_H$) and SEQ ID NO: 25 ($V_L$)) in conjunction with alternative constant regions, as well as isolated antigen binding portions thereof (e.g., one or more CDR regions SEQ ID NOs: 9, 11, 13, 27, 29, and 31, optionally in conjunction with their respective FR regions SEQ ID NOs: 15, 17, 19, 21, 33, 35, 37, 39). Targeting agents disclosed herein based upon the disclosed antibodies can include, without limitation, an immunoglobulin molecule, a monoclonal antibody, a polyclonal antibody, a chimeric antibody, a CDR-grafted antibody, a non-human antibody (e.g., from mouse, rat, goat or any other animal), a fully-human antibody, a humanized antibody, a Fab, a Fab', a F(ab')2, a Fv, a disulfide-linked Fv, a scFv, a single-domain antibody based on either a heavy chain variable domain or a light chain variable domain (a nanobody), a diabody, a multispecific antibody, a dual-specific antibody, an anti-idiotypic antibody, a bispecific antibody, a functionally active epitope-binding fragment thereof, bifunctional hybrid antibodies, a single chain of an antibody, etc. An antibody may be of any type (e.g., IgG, IgA, IgM, IgE, or IgD). In general, the antibody is an IgG, e.g., an IgG1, IgG2, or an IgG3 isotype. In one particular embodiment, an antibody can be an IgG1 isotype. In addition, an antibody can generally include kappa light chains.

Antigen binding compounds as disclosed herein are not limited to complete antibodies. In one embodiment, disclosed compounds and methods can utilize one or more antigen binding fragments of a complete antibody. For instance, methods and materials can incorporate one or more CDR regions of a full antibody that can target and bind an epitope of elastin. By way of example, a targeting agent can include one or more of SEQ ID NO: 9, SEQ ID NO: 11 or SEQ ID NO: 13, which describe CDR fragments of a variable region of a heavy chain (SEQ ID NO: 7) as described herein, optionally in conjunction with one or more of SEQ ID NO: 27, SEQ ID NO: 29, or SEQ ID NO: 31, which describe CDR fragments of a variable region of a light chain (SEQ ID NO: 25) as described herein. A CDR fragment can be provided in one embodiment bounded by one or both FR fragments as found in a complete variable region, or alternatively, can be utilized in an isolated format, independent of the natural FR fragments. By way of example, in one embodiment, a targeting agent as described herein can incorporate a peptide sequence including SEQ ID NOs: 15, 9, and 17, in sequential order, which includes a CDR fragment (SEQ ID NO: 9) of a monoclonal antibody described herein in conjunction with the FR fragments naturally found on either end of the CDR fragment (SEQ ID NO: 15 and SEQ ID NO: 17). FR fragments that can be utilized in conjunction with CDR fragments can include one or more of SEQ ID NOs: 15, 17, 19, 21, 33, 35, 37, and 39 in formation of a targeting agent that selectively recognizes an epitope of degraded elastin.

As utilized herein, the terms "selectively recognizes" and "selectively binds" mean that binding of the molecule to an epitope is 2-fold greater or more, for instance from about 2 fold to about 5 fold greater, than the binding of the molecule to an unrelated epitope or than the binding of an unrelated molecule to the epitope, as determined by techniques known in the art, such as, for example, ELISA, immunoprecipitation, two-hybrid assays, cold displacement assay, etc. Typically, specific binding can be distinguished from non-specific binding when the dissociation constant ($K_D$) is about $1\times10^{-5}$ M or less, or about $1\times10^{-6}$ M or less, for instance about $1\times10^{-7}$ M in some embodiments.

Functional antigen binding fragments of the disclosed antibodies can include Fab, a scFv-Fc bivalent molecule, F(ab')2, and Fv that are capable of specifically recognizing and binding with one or more of SEQ ID NOs: 1-3, e.g., one or more of SEQ ID NOs: 7, 9, 11, 13, 25, 27, 29, or 31.

Antigen binding peptides as described herein can incorporate modifications as would be understood by one of skill in the art. For instance, there are many natural amino acids, which occur as L-isomers in most living organisms; however, embodiments of the disclosure are not limited to only L-amino acids and can include modifications that substitute D-amino acids or other non-proteinogenic amino acids that are not naturally encoded by humans or any other organism. Herein, unless specifically referenced as a D-amino acid (i.e., the amino acid identifier followed by (d)), reference to a generic amino acid indicates the L-amino acid.

In embodiments of the disclosure, a targeting agent can include an ornithine substitution to disclosed peptides, e.g., to disclosed CDR fragments as may be utilized in a targeting agent. In some embodiments, a targeting agent can include one or more amino acid substitutions of a human proteinogenic amino acids selected from the following group: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

In one embodiment, a targeting agent can include structurally and/or functionally similar peptides to those disclosed herein. Structurally similar peptides can encompass variations such as the substitution of one amino acid having a first amino acid side chain with a second amino acid having a second amino acid side chain. Both the first amino acid side chain and the second amino acid side chain provide a similar characteristic to maintain functional similarity of the targeting agent, i.e., elastin epitope binding. A similar characteristic can include a side chain that has a similar polarity, charge, or size as the first amino acid side chain. As an example, leucine includes a hydrophobic side chain, and in some embodiments, a targeting agent can include substitution of a leucine of a disclosed sequence (e.g., a CDR sequence) with an isoleucine, valine, or alanine, as each of these amino acids includes a similar hydrophobic side chain. As another example, histidine includes an aromatic side chain that can also carry a positive charge, and in some embodiments, one or more histidines of an elastin binding antibody or fragment thereof can be substituted with an amino acid that includes an aromatic side chain or with an amino acid that can carry a positive charge, such as phenylalanine, tyrosine, tryptophan, arginine, or lysine. These are provided as examples of possible substitutions and are not meant to limit the scope of variations contemplated by substituting amino acids that have similar side chain properties.

In some embodiments, the antigen binding fragments comprise a Fab, in which the fragment contains a monovalent antigen binding fragment of the antibody molecule, and which can be produced by digestion of whole antibody with the enzyme papain to yield an intact light chain (e.g., SEQ ID NO: 23) or the variable region thereof (e.g., SEQ ID NO: 25) and a portion of one heavy chain (e.g., one or more of SEQ ID NO: 9, 11, 13, optionally in conjunction with one or more of SEQ ID NOs: 15, 17, 19, 21).

In one embodiment, the antigen binding fragment can comprise a Fab', which is the fragment of the antibody molecule that can be obtained by treating whole antibody with pepsin, followed by reduction, to yield an intact light chain (e.g., SEQ ID NO: 23) or the variable region thereof (e.g., SEQ ID NO: 25) and a portion of the heavy chain (e.g., one or more of SEQ ID NO: 9, 11, 13, optionally in conjunction with one or more of SEQ ID NOs: 15, 17, 19, 21); two Fab' fragments can be obtained per antibody molecule. A (Fab')2 fragment of the antibody is encompassed, which can be obtained by treating a whole antibody with the enzyme pepsin without subsequent reduction. A F(ab')2 fragment is a dimer of two Fab' fragments held together by two disulfide bonds. Also encompassed is a Fv, which is a genetically engineered fragment containing the variable region of the light chain and the variable region of the heavy chain expressed as two chains. In one embodiment, the antibody can encompass a single chain antibody ("SCA"), which is a genetically engineered molecule containing the variable region of the light chain and the variable region of the heavy chain, linked by a suitable polypeptide linker as a genetically fused single chain molecule. An antibody fragment can be an scFv-Fc, which is produced in one embodiment by fusing single-chain Fv (scFv) with a hinge region from an immunoglobulin (Ig), such as an IgG, and Fc regions.

An antibody or antigen binding fragment thereof can include a modification as is known in the art that does not interfere with the specific recognition and binding with the targeted epitope. For instance, a modification can minimize conformational changes during the shift from displayed to secreted forms of the antibody or fragment. As is understood by a skilled artisan, the modification can be a modification known in the art to impart a functional property that would not otherwise be present if it were not for the presence of the modification. The invention encompasses materials that are differentially modified during or after translation, e.g., by glycosylation, acetylation, phosphorylation, amidation, derivatization by known protecting/blocking groups, proteolytic cleavage, linkage to a particle, another molecule or other cellular ligand, etc. Any of numerous chemical modifications may be carried out by known techniques, including, but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

A modification can include a N-terminus modification and/or a C-terminal modification. For example, the modification can include a N-terminus biotinylation and/or a C-terminus biotinylation. In one embodiment, the secretable form of the antibody or antigen binding fragment comprises a N-terminal modification that allows binding to an Immunoglobulin (Ig) hinge region. In another embodiment, the Ig hinge region is from, but is not limited to, an IgA hinge region. In another embodiment, the secretable form of the antibody or antigen binding fragment comprises a N-terminal modification and/or a C-terminal modification that allows binding to an enzymatically biotinylatable site. In another embodiment, biotinylation of said site can functionalize the site to bind to any surface coated with streptavidin, avidin, avidin-derived moieties, or a secondary reagent.

A modification can include, for example, addition of N-linked or O-linked carbohydrate chains, attachment of chemical moieties to the amino acid backbone, chemical modifications of N-linked or O-linked carbohydrate chains, and addition or deletion of a N-terminal methionine residue.

The antibodies or antigen binding fragments can be produced by any synthetic or recombinant process such as is well known in the art. The antibodies or antigen binding fragments can further be modified to alter biophysical or biological properties by means of techniques known in the art. For example, an antibody can be modified to increase its stability against proteases, or to modify its lipophilicity, solubility, or binding affinity to one or more of SEQ ID NOs: 1-3.

By way of example, the antibodies can be produced by the immunization of various animals, including mice, rats, rabbits, goats, primates, chickens and humans with a target antigen such as an entire peptide sequence as described or a peptide fragment of elastin containing one or more of the sequences as described that include at least one anti-elastin epitope. In one embodiment, the antigen or peptide fragment containing the antigen can be purified prior to immunization of the animal. The antibody or antigen binding fragment obtained following the immunization can be purified by methods known in the art, for example, gel filtration, ion exchange, affinity chromatography, etc. Affinity chromatography or any of a number of other techniques known in the art can be used to isolate polyclonal or monoclonal antibodies from serum, ascites fluid, or hybridoma supernatants.

"Purified" means that the antibody is separated from at least some of the proteins normally associated with the antibody and preferably separated from all cellular materials other than proteins.

The antibodies or antigen binding fragments thereof may be produced by using gene recombination techniques. For example, in formation of a chimeric antibody, a humanized antibody, a functional fragment of antibody or the like, such as a Fv, a SCA, a scFv-Fc or the like, genetic recombination techniques.

In one embodiment, a method for producing a targeting agent that incorporates all or a portion of a variable region of a heavy chain (SEQ ID NO: 7) and a variable region of a light chain (SEQ ID NO: 25), e.g., including one or more CDR regions (SEQ ID NOs: 9, 11, 13, 27, 29, 31), for instance in formation of a chimeric antibody, can be carried out through utilization of genetic recombination techniques.

By way of example, DNA encoding an amino acid sequence ($V_H$ region) represented by SEQ ID NO: 7 is prepared. Likewise, DNA encoding an amino acid sequence ($V_L$) represented by SEQ ID NO: 25 is prepared. Examples of such DNA include those represented by SEQ ID NO: 6 and SEQ ID NO: 24; however, those having other nucleotide sequences may be used.

Portions or mutants of disclosed sequences, which still retain desired activity, are also considered within the scope of this disclosure. For example, mutants can include alterations to SEQ ID NO: 6 or SEQ ID NO: 24 that encode one or more amino acid substitutions (e.g., mutating a codon for valine to a codon for alanine). Additionally, or alternatively, mutants of a DNA sequence can include one or more point mutations to the native cDNA sequence to substitute a degenerate codon for the native codon.

For embodiments of the disclosure that include a mutant of a nucleic acid sequence as disclosed (e.g., SEQ ID NO: 6 or SEQ ID NO: 24 or portions thereof encoding a CDR region of an antibody), the mutant can include one or more codon mutations that modify the expressed protein to substitute one hydrophobic amino acid (e.g., valine) for another hydrophobic amino acid (e.g., alanine, leucine, isoleucine, proline, phenylalanine, methionine, or tryptophan) to produce an antibody variant.

Due to codon redundancy, there are many theoretically possible cDNA sequence variants that could encode an antibody or antigen binding fragment as described herein. Additionally, variants that modify the native protein sequence, while retaining binding activity, further increase this number. For these embodiments, a genetic modification can result in the expression of a peptide (e.g., SEQ ID NO: 7) or a peptide variant that retains the binding function of the native peptide.

A DNA encoding $V_H$ (e.g., SEQ ID NO: 7) or $V_L$ (e.g., SEQ ID NO: 25) can be inserted into a vector having a sequence encoding the respective constant regions ($C_H$ or $C_L$) of human antibody in one embodiment to construct a chimeric antibody expression vector. Vectors having a sequence encoding $C_H$ or $C_L$ of a human antibody as may be utilized are commercially available. By introducing the constructed expression vector into a host cell, a recombinant cell that expresses a chimeric antibody can be obtained. Following, the recombinant cell can be cultured, and a desired chimeric antibody can be acquired from the culture.

A host cell is not particularly limited as long as the expression vector is able to function therein. By way of example, animal cells (e.g., COS cells, CHO cells, HEK cells, and the like), yeast, bacteria (*Escherichia coli* and the like), plant cells, insect cells and the like may be appropriately employed.

In one embodiment, a recombination technique can be utilized to produce an antibody including specific CDR including one or more of SEQ ID NOs: 9, 11, 13, 27, 29, or 31. For instance, a method can be utilized in forming a humanized antibody, which, as utilized herein, refers to an antibody having a CDR derived from an animal other than human, and other regions (framework region, constant region and the like) derived from human.

For example, nucleotide sequences encoding heavy chain CDRs (SEQ ID NOs: 9, 11, 13) and light chain CDRs (SEQ ID NOs: 27, 29, 31) of an antibody can be prepared. As the DNA, a sequence corresponding to each CDR nucleotide sequence represented by SEQ ID NOs: 8, 10, 12, 26, 28, 30 is exemplified; however, as discussed above, those having other nucleotide sequences may be used. DNA may be prepared by known methods such as PCR. The DNA may be prepared by chemical synthesis.

Using these sequences, a sequence encoding a variable region in which heavy chain CDR encoding regions (e.g., SEQ ID NOs: 8, 10, 12) are grafted to the respective regions encoding framework regions (FR) of $V_H$ in a human antibody can be prepared. Likewise, sequences encoding a variable region in which light chain CDR encoding regions (e.g., SEQ ID NOs: 26, 28, 30) are grafted to the respective regions encoding FR of $V_L$ in a human antibody can be prepared. The prepared nucleic acid sequence can then be inserted into a vector having a sequence encoding the desired constant region ($C_H$ or $C_L$) of a human antibody, so as to construct a humanized antibody expression vector. By introducing the constructed expression vector into a host cell, a recombinant cell that expresses a humanized antibody can obtained. The recombinant cell can then be cultured, and a desired humanized antibody can be acquired from the culture.

A targeting agent including fewer than all of the CDRs of a full antibody can be produced in a similar procedure. For instance, a targeting agent that includes only the $V_H$ or only the $V_L$ region of an antibody, absent the constant region, can be produced in a similar fashion.

Methods for purifying a targeting agent formed according methods as described herein are not particularly limited and known techniques may be employed. For example, a culture supernatant of a hybridoma or a recombinant cell may be collected, and the antibody or antigen binding fragment may be purified by a combination of known techniques such as various kinds of chromatography, salt precipitation, dialysis, membrane separation and the like. When the isotype of the antibody is IgG, the antibody may be conveniently purified by affinity chromatography using protein A.

In utilization of disclosed materials, an antibody or antigen binding fragment can be operably linked to a secondary material for targeting and delivery of an agent to a degraded elastic fiber or to an area near a degraded elastic fiber. As utilized herein, the term "operably linked" refers to a direct or indirect linkage that can be either a permanent or temporary (e.g., degradable) linkage in which two or more molecules, sequences, particles or combination thereof are attached in such a manner as to ensure the proper function of the components, and in particular, in such a manner that the antibody or antigen binding fragment thereof can bind its epitope. As such, the antibodies or antigen binding fragment thereof can deliver any kind of useful agent to areas in or near connective tissues such as arteries, lungs, skin, etc. Moreover, in some embodiments, an antibody or antigen binding fragment can be directly linked to a carrier (e.g., a particle as described further herein) that can carry and deliver one or more active agents. As such, a composition can be utilized to deliver an active agent over an extended time period via controlled release of the agent from the carrier.

The antibodies or antigen binding fragments thereof can be utilized for delivery of biologically active agents in treatment or diagnosis of diseases for which elastin protein degradation is a hallmark including cardiovascular diseases, such as atherosclerosis and arteriosclerosis, and lung diseases, such as chronic bronchitis, COPD, and emphysema. Other conditions that can include elastic fiber degradation and for which the antibodies or antigen binding fragments thereof can be utilized in agent delivery can include those associated with aneurysm, arteriosclerosis, atherosclerosis, genetic disorders, blunt force injury, Marfan's syndrome, pseudoxanthoma elasticum, skin aging, and so forth. In one embodiment, the materials can be utilized for treatment of vascular calcification which is common in aging, as well as in a number of genetic and metabolic disorders. Vascular calcification is now recognized as a strong predictor of cardiovascular events in those suffering from other disorders such as in diabetes and chronic kidney disease (CKD), as well as in the general population. The materials can be utilized in treatment of medial arterial calcification (MAC), which can exist independently of atherosclerosis and is typically associated with elastic fiber degradation. Elastin-specific medial calcification leads to an elevation of systolic blood pressure (SBP) and pulse pressure (PP) and contributes to isolated systolic hypertension (ISH). In one embodiment, disclosed materials can be utilized in targeting immature and/or damaged elastin fiber simultaneously in intimal and medial calcification. For instance, when both atherosclerotic and medial calcification are present in a subject, disclosed materials can target by calcifications simultaneously.

In one embodiment, disclosed materials and methods can show benefit in stabilizing vulnerable atherosclerotic plaque. Atherosclerotic plaques have been found to include a fibrous cap that is produced over the plaque. It has recently been discovered that these fibrous caps can include immature (i.e., not fully crosslinked and formed). Currently research shows that some patients have stable plaques with thick fibrous cap, and some have a vulnerable thin cap. Rupture of plaque due to the presence of a relatively thin cap can lead to death. Disclosed antibodies can bind the immature elastin in these atherosclerotic fibrous caps and thereby assist in delivering bioactive agents to the local area, e.g., in conjunction with carrier nanoparticles. For example, agents that can stabilize collagen/elastin of the fibrous cap or that can otherwise increase the strength of the cap and prevent rupture can be delivered by use of the targeting antibodies.

The materials may have application in skin care, such as for conditions including scarring, skin sagging and wrinkles, which often occur with age due to loss/degradation of elastic fiber including that due to sun exposure or other disease states. Patients as may benefit from utilization of the delivery agents can also include those suffering from skin arterial conditions such as cutaneous vasculitis. Cutaneous vasculitis can cause elastic lamina damage in the small arteries in the skin, and use of the materials for delivery of treatment compositions can alleviate such damage.

Agents that can be delivered by use of the antibodies or antigen binding fragments thereof can include biologically active agents such as, and without limitation to, anticoagulants, antiplatelet agents, anti-inflammatory agents, SMC proliferation inhibitors, MMP and cathepsin inhibitors, cytostatic agents, antioxidants, chelating agents, elastin-stabilizing and regeneration agents, cytokines, enzymes, chemokines, radioisotopes, enzymatically active toxins, or chemotherapeutic agents.

In one embodiment, the materials can be utilized in delivery of genetic material that can include DNA and/or RNA nucleic acid constructs. Genetic material that can be delivered by use of the targeting materials described can include, without limitation, microRNA, transfer RNA, ribosomal RNA, silencing RNA, regulating RNA, antisense RNA, RNA interference, non-coding and coding RNA, DNA fragments, plasmids including genes in conjunction with regulatory sequences, precursors of functional constructs (e.g., mRNA precursors), DNA/RNA probes, etc., and the like.

Cystatins are one exemplary example of a cathepsin inhibitor as may be delivered by use of the materials. Examples of MMP inhibitors include inhibitors of MMP-2, MMP-9, and MMP-12, all of which have been implicated in elastin degradation. Such MMP inhibitors can include, without limitation, one or more of the four tissue inhibitor of metalloproteinases (TIMPs), i.e., TIMP1, TIMP2, TIMP3, or TIMP4. Synthetic MMP inhibitors include those containing a chelating group that binds the catalytic zinc atom at the MMP active site. As such, chelating agents as may be useful for MMP inhibition and/or other reasons are encompassed herein. Typical chelating groups include hydroxamates, carboxylates, thiols, and phosphinyls. Tetracycline antibiotics such as doxycycline, minocycline, and so forth can be delivered by use of the disclosed antibodies or antigen binding fragments thereof.

An antibody or antigen binding fragment thereof can be utilized in delivery of one or more immunomodulatory agents that may increase or decrease production of one or more cytokines, up- or down-regulate self-antigen presentation, mask MHC antigens, or promote the proliferation, differentiation, migration, or activation state of one or more types of immune cells. Immunomodulatory agents include, but are not limited to, non-steroidal anti-inflammatory drugs (NSAIDs); topical steroids; cytokine, chemokine, or receptor antagonists; heterologous anti-lymphocyte globulin; etc.

In one embodiment a biologically active compound for targeted delivery can include a compound as may be utilized to directly treat degraded elastin. Such compounds can include those that can encourage crosslinking of elastin, so as to provide additional structural support to the connective tissue, and compounds that can upregulate elastin formation, particularly through increased formation and/or crosslinking of tropoelastin. For instance, an elastin crosslinking agent such as pentagalloylglucose (PGG) can be delivered by use of the antibodies or antigen binding fragments thereof. Biologically active compounds that can encourage the formation and/or crosslinking of tropoelastin so as to encourage formation of new elastic fibers include lysyl oxidase enzyme and/or agents that increase lysyl oxidase activity such as copper ions, or forskolin, which is a cyclic AMP (cAMP) inducer. Another compound that can be utilized to encourage crosslinking of tropoelastin is TGF-β, which has been shown to increase lysyl oxidase activity. Copper ions ($Cu^{2+}$) can enhance extracellular transport of endogenous lysyl oxidase and functional activity of endogenous and exogenous lysyl oxidase by enabling electron transfer from oxygen to facilitate oxidative deamination and aldehyde formation at lysine residues in elastin. Accordingly, an antibody or antigen binding fragment thereof can be directly or indirectly linked with copper ions for delivery to a degraded elastic fiber.

In one embodiment, an agent that can dissolve minerals, such as for example, ethylenediaminetetraacetic acid (EDTA), which has been shown to be a versatile chelating agent; ethylene glycol-bis(3-aminoethyl ether)-N,N,N',N'-tetraacetic acid (EGTA), a calcium specific chelator; ethylene glycol tetraacetic acid; nitrilotriacetic acid, hydroxyethyl ethylenediaminetriacetic acid; 8-Hydroxy-7-iodo-5-quinolinesulfonic acid; poly(gamma-glutamic acid; sodium thiosulphate; alpha-lipoic acid; bisphosphonates; diethylenetriaminepentaacetic acid (DTPA); and/or other chelators as are known in the art can be delivered.

An antibody or antigen binding fragment thereof can be directly or indirectly linked to an imaging agent. Upon binding to degraded elastic fiber via the antibody, an imaging agent can be used in determination of the location and extent of elastic fiber degradation and diagnosis of a related or unrelated disease condition. Imaging agents can include those for CT or MRI scans, or SPECT imaging as is known in the art. Detectable markers as may be directly or indirectly linked to the materials can include photoactivatable agents, fluorophores, radioisotopes, bioluminescent proteins or peptides, fluorescent tags (e.g., fluorescein, isothiocyanate (FITC), a cyanine dye, etc.), fluorescent proteins or peptides, affinity labels (e.g., biotin, avidin, protein A, etc.), enzymatic labels (e.g., horseradish peroxidase or alkaline phosphatase), or isotopic labels (e.g., 125I), gold particles, rods, x-ray opaque substances, and micro bubbles (e.g., for ultrasound imaging), or any other such detectable moiety to allow for detection of the antibody and optionally imaging of the area.

As mentioned, the antibody or antigen binding fragment can be directly linked to a bulk material (generally, but not necessarily, in the form of a particle) that can carry an agent for delivery to the area of a degraded elastic fiber. In general, any bulk biocompatible synthetic or natural material capable of being formed to a useful size and shape can be utilized in forming the carrier. In one embodiment, a polymeric particle can be utilized. For instance, particles formed from natural or synthetic polymers including, without limitation, polystyrene, poly(lactic acid), polyketal, butadiene styrene, styrene-acrylic-vinyl terpolymer, poly(methyl methacrylate), poly(ethyl methacrylate), poly(alkyl cyanoacrylate), styrene-maleic anhydride copolymer, poly(vinyl acetate), poly(vinyl pyridine), poly(divinylbenzene), poly(butylene terephthalate), acrylonitrile, vinyl chloride-acrylates, poly(ethylene glycol), and the like, or an aldehyde, carboxyl, amino, hydroxyl, or hydrazide derivative thereof can be utilized. Particles formed of biological polymers such as proteins can be used. For instance, particles formed of albumin (e.g., bovine serum albumin), dextran, gelatin, chitosan, dendrimers, liposomes, etc. can be utilized. Such particles can be preferred in certain embodiments as they can be formed without the use of organic solvents according to known methods. Other biocompatible materials as may be utilized in forming carrier particles can include, without limitation, oxides such as silica, titania, zirconia, and the like, and noble metals such as gold, silver, platinum, palladium, and the like. In general, the materials will be biocompatible and non-immunogenic. Suitable biodegradable materials can include, without limitation, polysaccharide and/or poly(lactic acid) homopolymers and copolymers. For example, particles formed of poly(lactic-co-glycolic acid) (PLGA) copolymers, poly(ethylene glycol) (PEG)/poly(lactic acid) (PLA) block copolymers, and derivatives thereof can be utilized.

Selection of bulk carrier material can be utilized to provide control of release rate of a biologically active agent from the loaded particle. For instance, selection of a biodegradable material can be utilized to control the rate of agent release and provide a release mechanism that can be controlled to a large extent by particle degradation rate and to a lesser extent by diffusion of the active agent through and out of the bulk particle. Materials can be utilized such that active agent release rate is limited by one of diffusion (e.g., a nondegradable particle) or nanoparticle degradation rate (e.g., essentially no diffusion of the active agent through the particle due to small matrix mesh size), or to some combination thereof that can be engineered for a desired release rate.

Particles can be microparticles or nanoparticles. As utilized herein, the term nanoparticle generally refers to a particle of which the size, i.e., the average diameter, can be about 1000 nanometers (nm) or less, generally about 500 nm or less, for instance about 200 nm or less, or about 100 nm or less. In one particular embodiment, nanoparticles can be about 50 nm or less in size, for instance about 20 nm in average diameter. In one embodiment, nanoparticles can have an average diameter of from about 50 nm to about 400 nm, or from about 100 nm to about 300 nm.

Larger particles can alternatively be utilized. For instance, in other embodiments, microparticles having an average size of up to about 50 micrometers ($\mu m$) can be utilized as a carrier.

In general, the preferred size of particles can depend upon the specific application, e.g., the specific method of delivery of the agents, such as via surface application (as in a cream or lotion), via parenteral injection using the circulatory or digestive tract, via inhalation, etc., as well as the desired release rate of an agent from the particles. For instance, particles can be of a size to prevent cellular uptake so as to remain in the extracellular matrix and available for interaction with damaged elastic fibers. Thus, the particles may be about 100 nm or larger in one embodiment, as smaller particles have been shown to exhibit higher cellular uptake. Particles can also be small enough so as to penetrate endothelium and penetrate basement membrane so as to contact the elastic fibers of the connective tissue. For instance, particles can be about 400 nm or less in average diameter in one embodiment so as to penetrate endothelium and basement membrane. When intended for use in an intravenously administered formulation, large particles (e.g., greater than about 1 $\mu m$) are typically disfavored because they can become lodged in the microvasculature. In addition, larger particles can accumulate or aggregate in vivo. As such, for intravenous administration, particles under 1 $\mu m$ are typically used.

Generally, particulate carriers can be substantially spherical in shape, although other shapes including, but not limited to, plates, rods, bars, irregular shapes, etc., are suitable for use. As will be appreciated by those skilled in the art, the composition, shape, size, and/or density of the particles may vary widely.

Particles can be designed with a desirable surface charge so as to better target damaged elastic fibers. For instance, positively charged nanoparticles have shown superior cellular uptake in comparison to negatively charged particles. Thus, in one embodiment, particles can be developed with a negative surface charge to maintain the particles in the extracellular matrix and avoid cellular uptake.

Particles can be loaded with one or more agents according to any suitable method. For instance, a precipitation method can be utilized to form the loaded particles in a one-step formation process. According to this method, a particle bulk material (e.g., a biocompatible polymer such as poly-(D,L-lactide-co-glycolide or a PGA/PLA copolymer) can be dissolved in a solvent. Suitable solvents can depend upon the specific materials involved. For example, organic solvents including acetone, tetrahydrofuran, dimethylsulfoxide, dimethylformamide, or acetonitrile and the like can be utilized. The solution can undergo standard processing such as sonication, etc., so as to adequately solubilize the polymer. The solution can then be added, generally dropwise, to a second solution. Either spontaneously or following an emulsification method, for instance following sonication, particles of the bulk material can form in the second solution that.

When utilizing a single-step formation process, an agent for delivery (e.g., a therapeutic) can also be included in either the first solution or the second solution. Upon formation of the particles, the agent can be incorporated in the particles with the bulk material.

Initial concentration of an agent within or on a particle will obviously vary depending upon the nature of the agent, delivery rate, etc. For example, in one embodiment, loading concentration of a biologically active agent in/on a particle can vary from about 4 wt. % to greater than about 40 wt. % by weight of the particle, with higher and lower concentrations possible depending upon specific agent, particle bulk material, and the like. For instance, in an embodiment in which an agent for delivery exhibits high solubility in the bulk particle material, a very high loading level can be attained, particularly when both materials are highly hydrophobic.

Formation processes can include two-step processes in which particles are first formed followed by a second loading step in which one or more active agents are loaded into the formed particles or onto the surface of the formed particles. For instance, a method can include swelling a pre-formed, optionally crosslinked, polymeric particle in a solution that includes the agent for delivery so as to load the particle via a diffusion process. In another embodiment, loading method can include double emulsion polymerization, which enables loading of hydrophilic compounds into hydrophobic particles. The formation method for nanoparticles is not particularly limited and other formation methods as are known in the art, e.g., sonication methods, solvent precipitation methods, etc., may be utilized.

Loaded particles can be formed so as to control the rate of release of active compound from a particle. Suitable control mechanisms are known to those of skill in the art. For instance, release rates can depend upon the relative concentration of an agent for delivery to bulk particle material, upon the molecular weight and degradation characteristics of the bulk nanoparticle material, upon the mesh size of a polymer particle matrix, upon the binding mechanism between the surface of a particle and an agent, and so forth, as is known. In any of these cases, one of ordinary skill in the art is capable of engineering a system so as to achieve desirable release rate. For instance, in the case of purely diffusion-limited release, such control can be achieved by variation of agent concentration within particles and/or particle size, particle polymer mesh size, and so forth. In the case of purely degradation-limited release, polymer monomer units, for instance glycolic acid content of a PLGA polymer, and/or molecular weight of particle bulk material, as well as particle size, can be adjusted to "fine tune" active compound release rate. For example, use of PLGA polymers with higher glycolic acid content and lower molecular weight can lead to an increased degradation rate of a particle formed with the polymer. Release rate of an agent from particles can be adjusted utilizing the above parameters so as to produce carriers capable of sustained release for periods varying from a few days to a few months, with the maximum release rates generally varying from a few hours to a few weeks.

Agents for delivery need not necessarily be incorporated within the bulk material. For example, in one embodiment, an agent can be bonded to the surface of a particle. For example, an agent can be bonded to the surface of a particle utilizing chemistry similar to that as is described in more detail below with regard to the binding of the epitope binding antibodies or fragments to the particles.

An antibody or antigen binding fragment can be conjugated with a carrier according to any suitable process. For example, a particle can include surface reactive groups to facilitate conjugation of the particle with an antibody. Surface reactive groups can include, without limitation, aldehyde, carboxyl, amino, hydroxyl, and the like. Surface reactive groups can either exist on the particle surface as formed or can be added to the surface following formation, for instance via oxidation, amination, etc., of the formed particle, as is generally known in the art. An antibody or fragment can then be conjugated with the particle, for instance through reaction with maleimide in which the antibody is a thiolated antibody.

An antibody or fragment can be attached to a carrier (e.g., a particle) via either nonspecific adsorption or a covalent bond. Preferred attachment methods can generally depend upon the desired application of the formed conjugates. For instance, in those embodiments in which a system is designed to function in vivo, carrier particles can be expected to encounter multiple collisions with various biological agents and tissues. Accordingly, covalent binding can be preferred in such an embodiment to better ensure that the antibodies/fragments will not be dislodged through collision of the particles with other materials.

The specific chemistry utilized to bind the antibodies/fragments (and optionally, another agent such as an active treatment agent as well) to a carrier surface is not particularly limited. For example, in one embodiment, an antibody or fragment can be attached to a chloromethylated particle according to a nucleophilic substitution reaction between an amine group of the polypeptide and an alkyl chloride of the particle. In another embodiment, soluble carbodiimide (EDC) and glutaraldehyde chemistry can be used to achieve covalent binding of amine groups of the polypeptide to carboxylated and aminated particles, respectively. According to yet another embodiment, a peptide can be bonded to a particle through initial covalent attachment of a streptavidin monolayer to a particle followed by controllable attachment of desired amounts of biotinylated antibody. According to yet another embodiment, an antibody/fragment can be covalently attached to a particle using a crosslinking agent, for instance a phenylazide crosslinking agent such as Pierce™ sulfo-HSAB (N-Hydroxysulfosuccinimidyl-4-azidobenoate) a photoreactive reagent that can crosslink amine groups of the peptide and C—H or C—C bonds of a polymeric particle.

In one embodiment, a molecular spacer, for instance a hydrophilic spacer, can be utilized to tether an antibody/fragment to a particle. Utilization of a spacer can prevent interaction of covalently bound peptides with the particle surface and thus prevent structural changes of the antibodies/fragments that can lead to partial or complete loss of functionality. Spacers can include long (e.g., weight average molecular weight between about 2,000 and about 20,000 Da) hydrophilic polymers such as, without limitation, poly(ethylene glycol), polyvinyl alcohol, polysaccharides, and so forth.

The spacer and the particle can include or be processed to include functionality so as to facilitate binding to one another. For example, a PEG spacer can include aldehyde functionality and can bind to an aminated particle through covalent reaction between the aldehyde group of the spacer and the amine group of the particle. A thiolated antibody/fragment can then be attached to the spacer according to a simple process including mixing of a solution including the thiolated antibody with an aqueous suspension of particles in the presence of maleimide.

At the final stage of conjugation, a carrier particle can be blocked, for instance, with a surfactant, such as Tween® 20, Pluronic®, or dextrane that can be adsorbed on the particle to block any hydrophobic surface exposed to the solution as well as to displace any nonattached agents. Low concentrations of such materials generally do not interfere with the activity of agents. The presence of a surfactant can reduce undesirable protein-particle interactions and prevent particle aggregation. It can also prevent nonselective "fouling" of the surface of a particle with other proteins in the environment in which the material is utilized that could potentially deactivate a system.

In one embodiment, a carrier can be engineered to exhibit anchoring properties for a desired application. For example, the binding capacity and length of time a carrier particle can remain attached to degraded elastic fiber and can be engineered by altering particle size and/or concentration of the targeting antibodies/fragments on the particle surface.

Conjugated compounds can be delivered to degraded elastic fiber according to any suitable method, generally depending upon where the targeted fiber is. For example, when considering a systemic delivery method, such as an intravenous delivery route, the conjugates can circulate until the damaged elastic fiber is contacted, for purposes of illustration only and not intended to be limiting, as in the case of elastosis. Once bonded to an elastic fiber via the antibody/fragment, an agent can facilitate detection or can be released from the particle via, e.g., particle degradation, diffusion, etc. to provide the desired activity. Compounds may be delivered or administered acutely or chronically according to various delivery methods, including sustained release methods incorporating perivascular or endovascular patches, topical application, intravenous delivery, osmotic pumps, inhalation, and so forth.

The present disclosure may be better understood with reference to the Examples, below.

Formation Methods

Monoclonal Antibody Formation

Keyhole limpet hemocyanin (KLH) was conjugated to the selected amino acid peptide fragment of rat elastin (i.e., one of SEQ ID NOs: 1-3). Using standard protocols, RBF/dnj or balb/c mice were sensitized subcutaneously (s.c.) with an initial dose of 100 µg total KLH-peptide protein in phosphate buffered saline (PBS) and TiterMax® adjuvant in a total volume of 200 µL. A subsequent booster was given 14 days later in Freund's incomplete adjuvant. Adjuvant-free boosters were then given at 21-day intervals, for a total of 4 immunizations. The last immunization was given by an intraperitoneal (i.p.) injection. Five days after the last immunization, mice were euthanized in $CO_2$ chambers and spleens were harvested for cells that were then fused with either FOX-NY or Sp2/0-Ag14 myelomas in the presence of polyethylene glycol (PEG) to make hybridomas to be cultured in 96-well microtiter plates using standard cell growth procedures. Fourteen days after fusion, supernatants from these crude hybridoma mixtures were screened for immune reactivity against unconjugated free peptide fragments by ELISA steps. Positive hybridomas were further cultured and cloned by limiting dilution to yield a monoclonal antibody secreting cell line (hybridoma). Hybridoma culture supernatants were then re-checked for specificity and fully characterized as to isotype and technical applications.

Polyclonal Antibody Formation

Keyhole limpet hemocyanin (KLH) was conjugated to the selected amino acid peptide fragment of rat elastin (i.e., one of SEQ ID NOs: 1-3). White New Zealand rabbits were sensitized subcutaneously (s.c.) with an initial dose of 100 µg total KLH-peptide protein in phosphate buffered saline (PBS) and TiterMax® adjuvant in a total volume of 200 µL, given at each of the two shoulder regions, and at each of the two back haunch regions. A subsequent booster was given 14 days later in Freund's incomplete adjuvant. Adjuvant-free boosters were then given at 21-day intervals, for a total of 5 immunizations. Ten days later, the rabbits were euthanized and exsanguinated, the blood allowed to clot, and serum was collected after centrifugation. The serum was then characterized as to antibody titer.

Nanoparticle Formation.

Nanoparticles Loaded with DiR Dye (Useful for Fluorescent Labeling and In Vivo Imaging)

Particles loaded with DiR dye were prepared by coacervation. Briefly, fluorescent infra-red dye 1,1-dioctadecyl-3,3,3,3-tetramethylindotricarbocyanine iodide (DIR)-loaded nanoparticles (DIR-NPs) were obtained by dissolving 250 mg bovine serum albumin (BSA) (SeraCare™, MA) in 4 mL of deionized water. Then, 2.5 mg of DIR was dissolved in 100 µL of acetone and added to the BSA solution. After an hour of stirring, the mixture was added dropwise to 24 mL of ethanol under continuous sonication (Omni Ruptor 400 Ultrasonic Homogenizer, Omni International Inc, Kennesaw, GA) for half an hour. For crosslinking, glutaraldehyde (EM grade 70%, EMS, PA) was added during stirring (42 µg per mg of BSA). Next, 10 mg of DIR-NPs were incubated with 2.5 mg heterobifunctional crosslinker α-maleimide-ω-N-hydroxysuccinimide ester poly (ethylene glycol) (Maleimide-PEG-NHS ester, MW 2000 Da, Nanocs Inc., NY) to achieve a sulfhydryl-reactive particle system. Traut's Reagent (34 µg, G-Biosciences, Saint Louis, MO) was used for thiolation of 10 µg of rabbit anti-rat elastin antibody (United States Biological, Swampscott, MA) as control or an antibody formed against the sequences described herein, and the mixture was incubated in HEPES buffer (20 mM, pH=9.0) for an hour at room temperature. Thiolated antibodies were rinsed with HEPES buffer and were added to the nanoparticles (4 µg antibody per 1 mg NPs) and incubated overnight for conjugation.

Nanoparticles Loaded with EDTA (a Chelating Agent)

EDTA-loaded nanoparticles (EDTA-NPs) were obtained by dissolving 200 mg of BSA (SeraCare™, MA) and 100 mg ethylenediaminetetraacetic acid disodium salt (EDTA) (Fisher Scientific™, NJ) in 4 mL of deionized water and pH was adjusted to 8.5. The aqueous solution was added dropwise to 16 mL ethanol under probe sonication for 1 hour. For crosslinking, glutaraldehyde was added during sonication (10 µg per mg of BSA). The elastin antibody conjugation procedure was similar to that of DIR-NPs.

Nanoparticles Loaded with PGG (Useful for Stabilizing Elastin)

PGG-loaded nanoparticles (PGG-NPs) were obtained by dissolving 250 mg of BSA (SeraCare™, MA) in 4 mL of deionized (DI) water. PGG (125 mg) was dissolved in 400 µl of dimethyl sulfoxide and added slowly to the BSA solution. After an hour of stirring, the mixture was added dropwise to 24 mL of ethanol under continuous sonication for half an hour. Glutaraldehyde was added during stirring at a concentration of 12 µg/mg protein (BSA). The elastin antibody conjugation procedure was similar to that of DIR-NPs.

Nanoparticles Loaded with an MMP Inhibitor BB-94

Poly (D,L-lactide) (PLA) nanoparticles were prepared using a nano-precipitation method based on solvent diffusion. PLA (Average MW 75 k-120 k) (Sigma Aldrich, St. Louis, MO) was dissolved in acetone (VWR International, Radnor, PA). 1,2-distearoyl-sn-glycero-3-phosphoethanolamine-N-[methoxy(polyethylene glycol)-2000](DSPE-PEG (2000) Maleimide) (Avanti Polar Lipids, Inc., Alabaster, AL) and BB-94 (Sigma Aldrich, St. Louis, MO) were dissolved in dimethyl sulfoxide (DMSO) (Sigma Aldrich, St. Louis, MO) the above solution was then added to the PLA solution. Polymer solution was added dropwise (16 µl/sec) to water kept under sonication (Omni Ruptor 4000) for 20 minutes at 4° C. Following sonication, the particles were washed twice with distilled water by centrifugation at 14000×g for 30 minutes at 4° C. and then resuspended in distilled water. Non-solvent (water) to solvent (acetone) ratio was 1:15 for all experiments. Three different batches containing 5:1, 10:1 and 15:1 polymer-to-BB-94 ratio were prepared in which the ratio between the two polymers (PLA:DSPE-PEG(2000) Maleimide) was 4:1. The elastin antibody conjugation procedure was similar to that of DIR-NPs.

Nanoparticles Loaded with a Doxycycline Hyclate

Doxycycline hyclate (Sigma Aldrich, St. Louis, MO) loaded BSA nanoparticles were prepared using a similar procedure. Briefly, 25 mg of doxycycline hyclate (DOXTot) was dissolved along with 100 mg of BSA (BSATot) in 2 mL of water and was allowed to stir at 500 rpm for 30 minutes. Following, 4 mL of ethanol was added dropwise at a rate of 1 ml/min using an automated dispenser, which made the solution turbid. To this, 8% glutaraldehyde (40 µg/mg BSA) was added to crosslink the albumin, and the mixture was stirred for 2 hours at room temperature. The resulting solution was centrifuged at 14,000 rpm for 10 minutes to separate formed nanoparticles. Nanoparticles were washed thrice with DI water before proceeding with anti-elastin antibody conjugation. The supernatant obtained from the washout was used to estimate the amount of free doxycycline (DOXF) by measuring absorbance at 273 nm using a UV spectrophotometer (BioTek Instruments Inc., Winooski, VT). Difference between DOXTot and DOXF gave the amount of doxycycline encapsulated (DOXNP) which was about 17%.

Example 1

Monoclonal and polyclonal antibodies were formed against SEQ ID NO: 1 (GALGPGGKPPKPGAGLL) as described.

Figure 2:
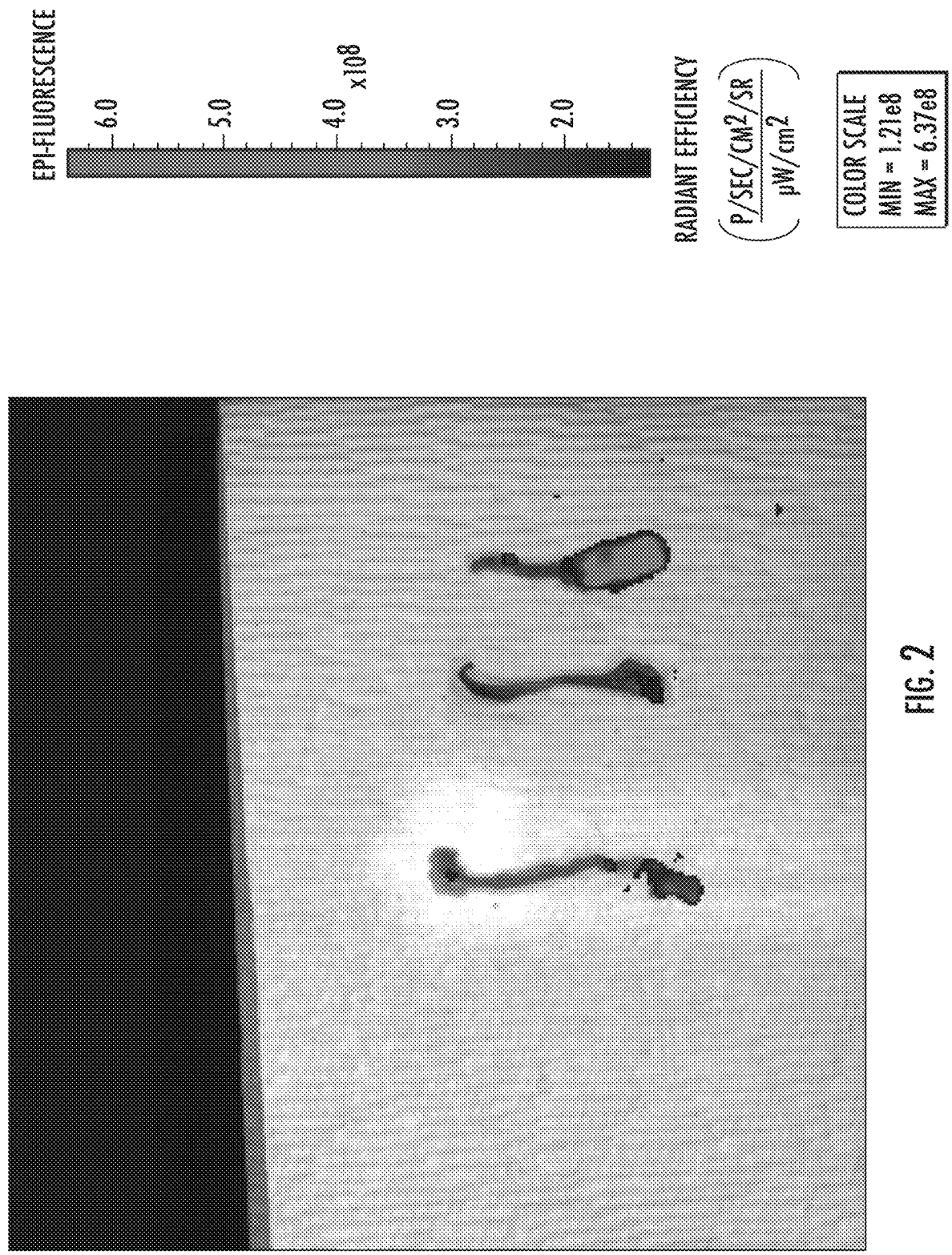
FIG. 2 illustrates mouse aortae, a portion of each of which having been treated with elastase, following incubation with nanoparticles tagged with disclosed antibodies.

Rat and mice aortae (n=8) were purchased from BioChemed Inc. Elastase solution was prepared by dissolving porcine pancreatic elastase (10 U/mL) in DI water. Aortae were tied to a suture and bottom halves of aortae were suspended in elastase solution for 1 hour at 37° C. The aortae were then washed in saline thoroughly and the whole aortae were incubated overnight in 10 mg/mL solution of DiR-NPs that were tagged with monoclonal antibodies to SEQ ID NO: 1. Following, aortae were washed in saline for 90 minutes on a shaker and imaged using IVIS imaging system. FIG. 1 illustrates the results for the rat aortae, and FIG. 2 illustrates the results for the mouse aortae. As shown, the anti-elastin antibodies preferentially bonded to the portions of the aortae that included the degraded elastic fibers.

Figure 3:
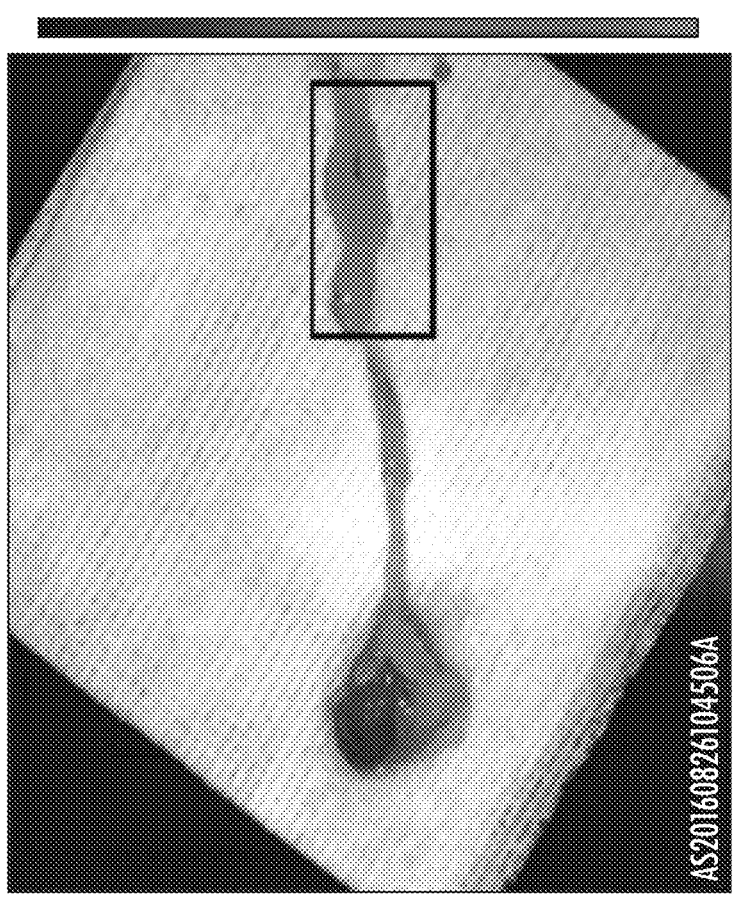
FIG. 3 illustrates damaged rat aortae following in vivo targeting by nanoparticles tagged with a detectable marker and disclosed antibodies.
Figure 3:
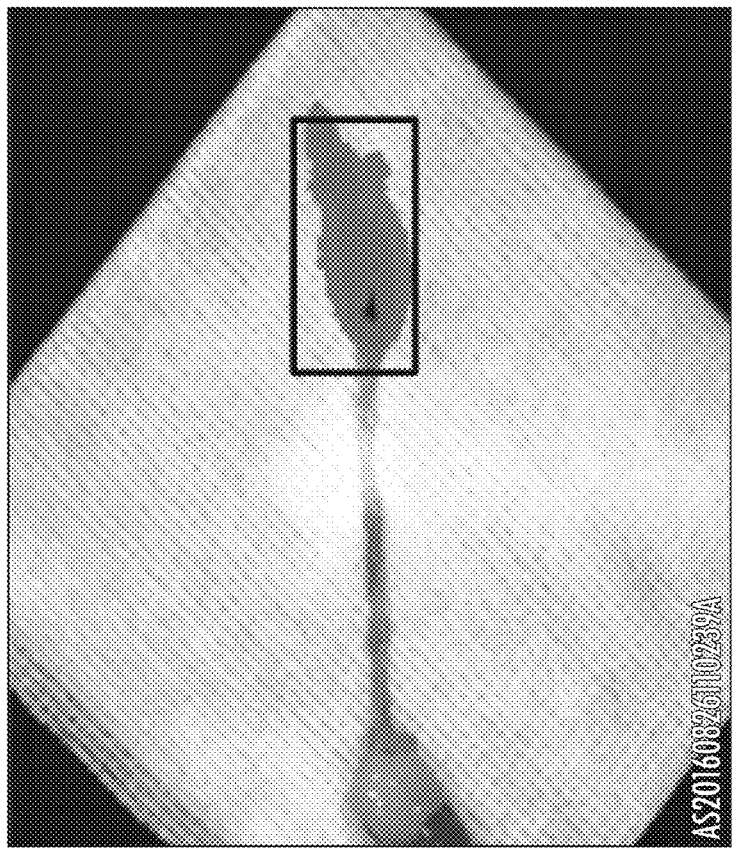

Eight Sprague Dawley male rats of 6 weeks of age were subjected to abdominal aortic injury by periadventitial application of 0.5 M CaCl$_2$ thrice for 5 minutes each. After 10 days of injury, rats were injected with BSA-DiR NPs, at a concentration of 10 mg/kg, tagged with anti-elastin monoclonal antibody to SEQ ID NO: 1. Twenty-four hours after injection, the animals were euthanized and their aortae were imaged using IVIS Imaging system for nanoparticle targeting. As indicated in FIG. 3, the antibody successfully targeted the damaged elastin (square area) in the aorta while sparing the healthy elastin in the other parts of aorta.

Example 2

Figure 4:
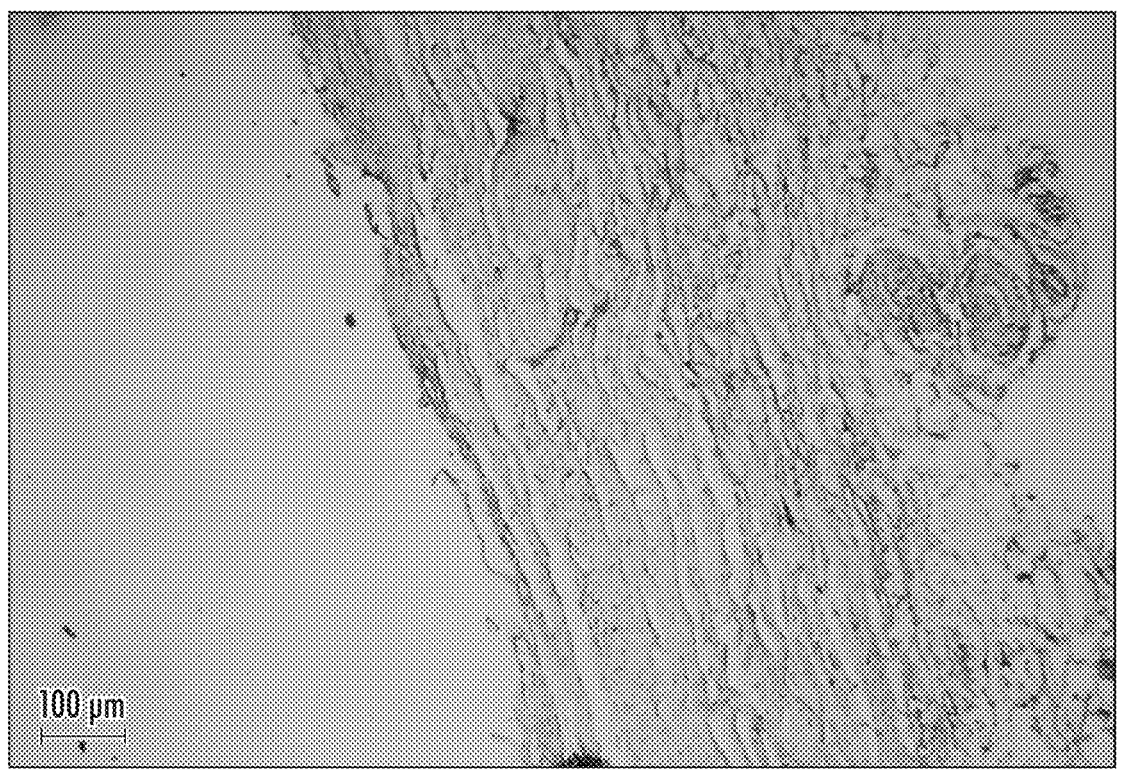
FIG. 4 illustrates immunohistochemistry staining using an antibody as disclosed herein as the primary antibody of the protocol.
Figure 5:
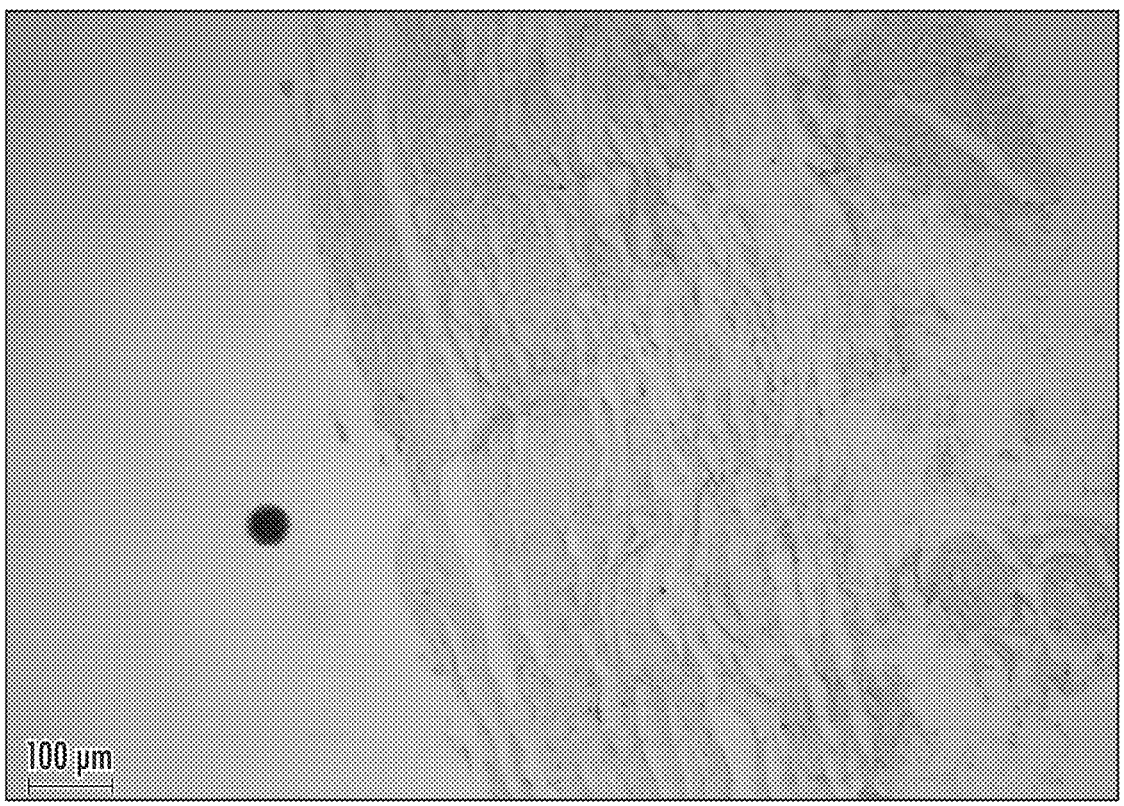
FIG. 5 illustrates immunohistochemistry (IHC) staining using a secondary antibody only as control
Figure 6:
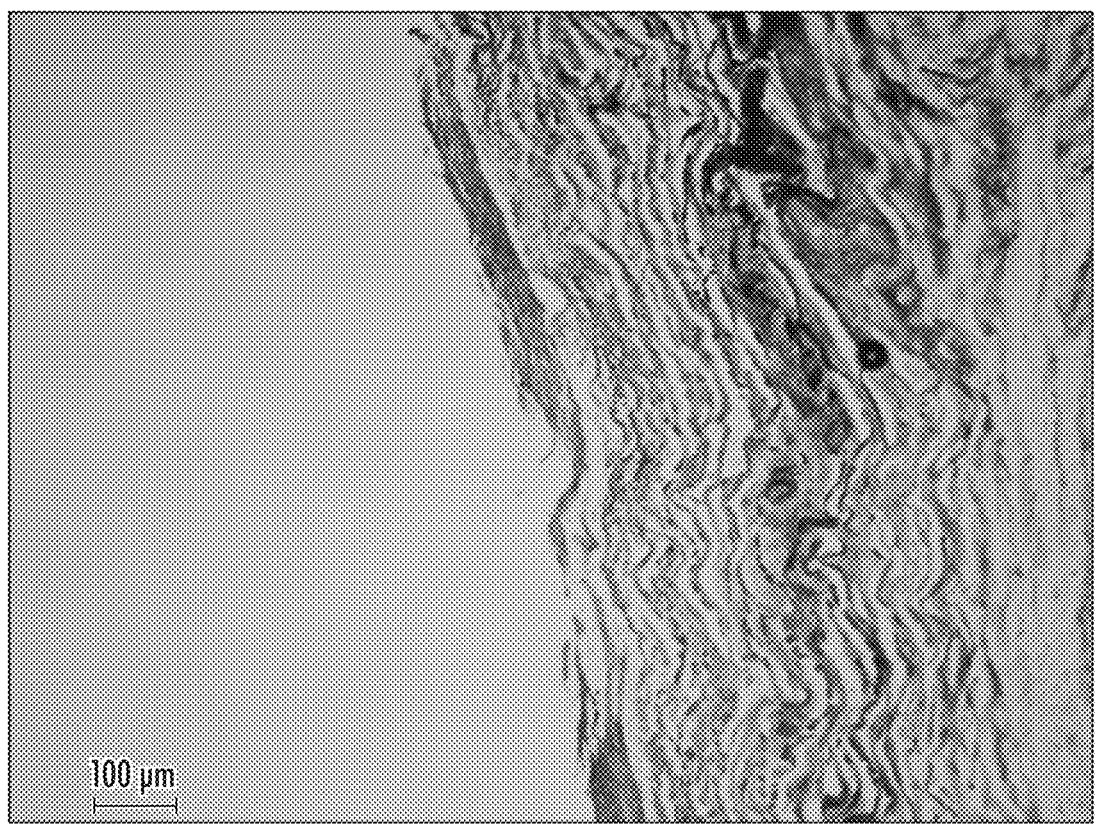
FIG. 6 illustrates the results of Verhoeff-van Gieson staining of human tissue tagged with an antibody as disclosed herein.
Figure 7:
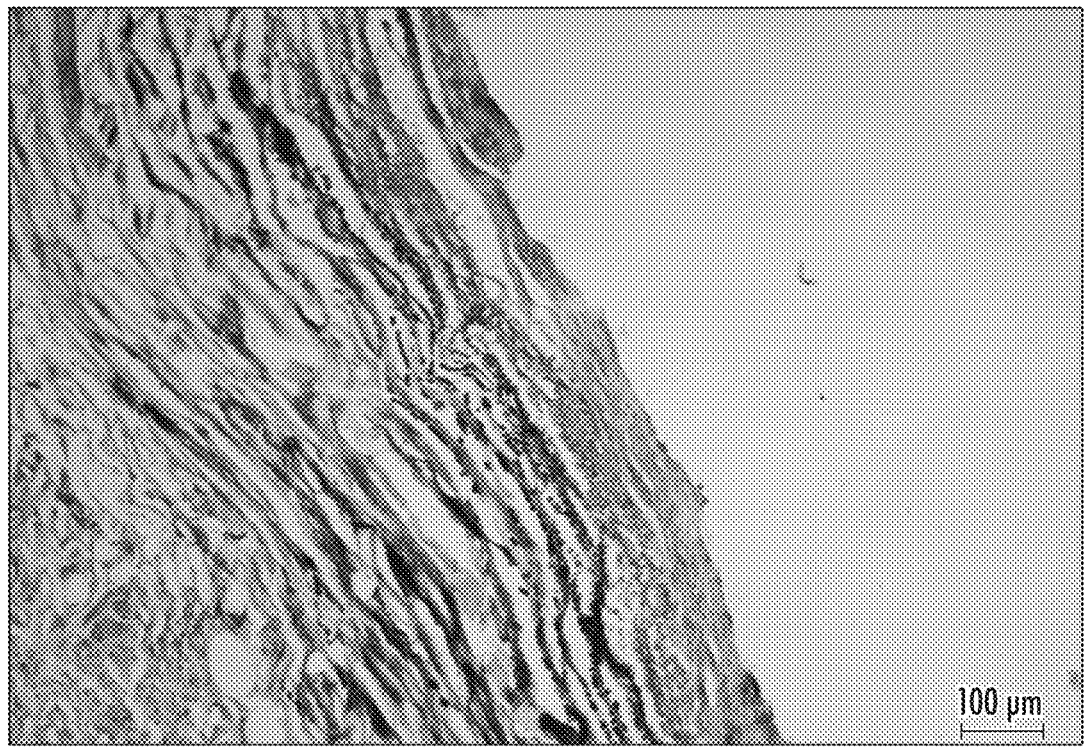
FIG. 7 illustrates the results of Verhoeff-van Gieson staining of human tissue showing damaged elastic fibers.

A portion of a calcified human leg artery was processed and embedded in paraffin. 5 µm sections were cut and mounted on positively charged glass slides and histological analysis was performed. Immunohistochemistry (IHC) to detect elastin with monoclonal antibody to SEQ ID NO: 1 as the primary antibody (10 µg/mL) was performed using a commercially available IHC Kit (Enzo Life Sciences, Inc.). Further, Verhoeff van Gieson (VVG) stains were used to identify broken (or damaged) elastin fiber. IHC revealed that the antibody to SEQ ID NO: 1 was able to successfully tag damaged elastin present in the artery indicated by the darker areas of FIG. 4. VVG stain showed that the elastin was broken and damaged (FIG. 6, FIG. 7). Even though damaged elastin fiber was visible with VVG, IHC for elastin did not show any dark staining when incubated with the control antibody only (FIG. 5), effectively confirming that the antibody to SEQ ID NO: 1 was able to recognize and bind to the human elastin of the damaged elastic fibers, whereas the control antibody did not.

Example 3

An emphysema model was developed in six-week old male Sprague-Dawley rats (n=6) that received an intratracheal injection of 50 U porcine pancreatic elastase (PPE) (Elastin Products Company Inc., Owensville, MO) dissolved in phosphate buffered saline (PBS) and filter sterilized. The elastase-treated rats developed elastin damage over four weeks. Animals were euthanized and aortae were carefully explanted after flushing the whole body with saline. A portion of lungs was processed and embedded in paraffin. Five-micron thick sections were made, and immunohistochemistry was performed using monoclonal antibody as described herein as primary antibody with various tissues using IHC kit (Enzo Life Sciences, Inc.). IHC for paraffin-embedded sections were performed according to manufacturer's protocol. Concentration of antibody was maintained at 10 µg/mL for all experiments.

Figure 11:
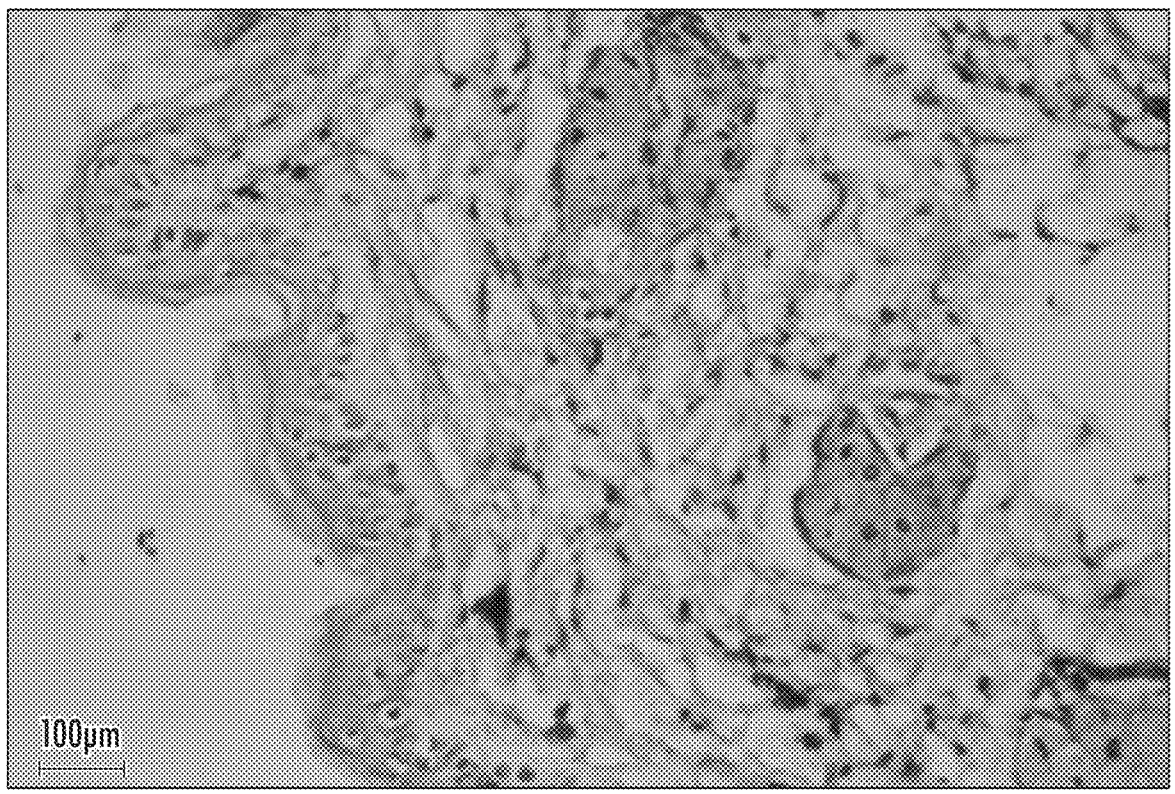
FIG. 11 illustrates IHC staining of elastase treated mouse skin using an antibody as disclosed herein as the primary antibody of the protocol.

A similar protocol was used to develop an emphysema model in mouse and an AngII aneurysm model in mouse. FIG. 8-FIG. 11 illustrate IHC staining of the various tissues following incubation with a monoclonal antibody to SEQ ID NO: 1 in the animal models including the elastase emphysema model in rat lungs (FIG. 8), the elastase emphysema model in mouse lungs (FIG. 9), the AngII aneurysm model in mouse aorta (FIG. 10), and elastase-treated mouse skin (FIG. 11). As shown, the antibody raised against SEQ ID NO: 1 was able to tag damaged elastin in multiple different tissue types.

Figure 8:
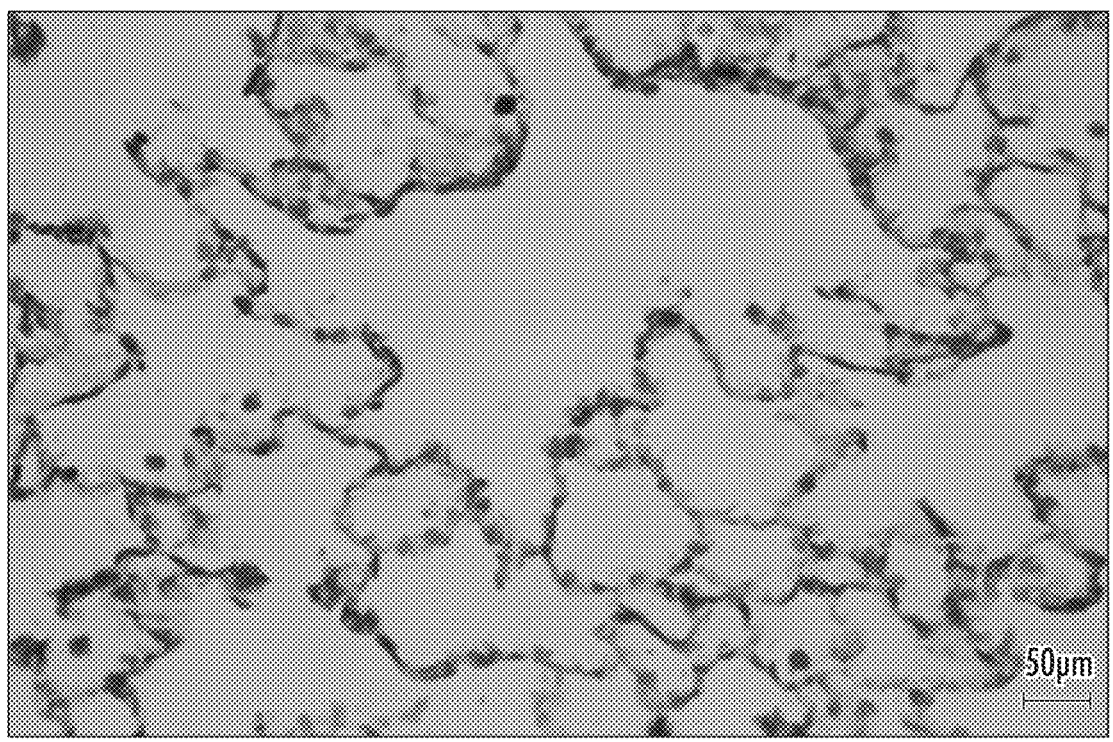
FIG. 8 illustrates IHC staining of tissue from an elastase emphysema model in rat lungs using an antibody as disclosed herein as the primary antibody of the protocol.
Figure 9:
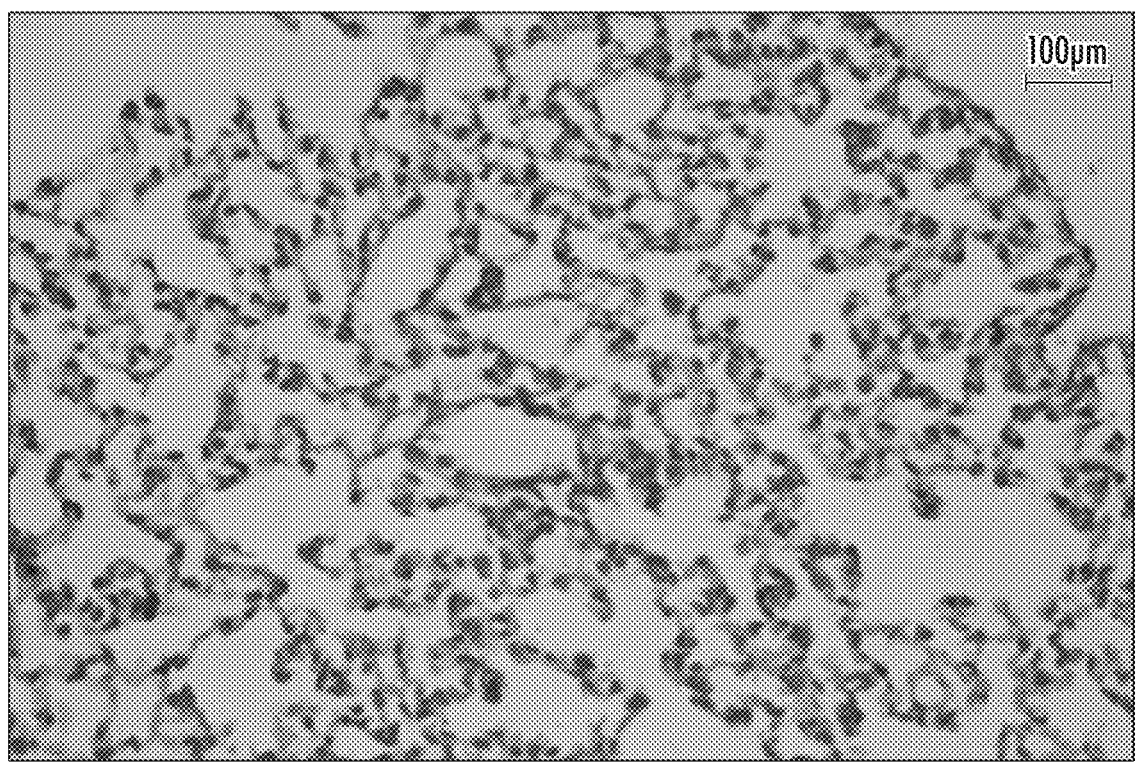
FIG. 9 illustrates IHC staining of tissue from an elastase emphysema model in mouse lungs using an antibody as disclosed herein as the primary antibody of the protocol.
Figure 10:
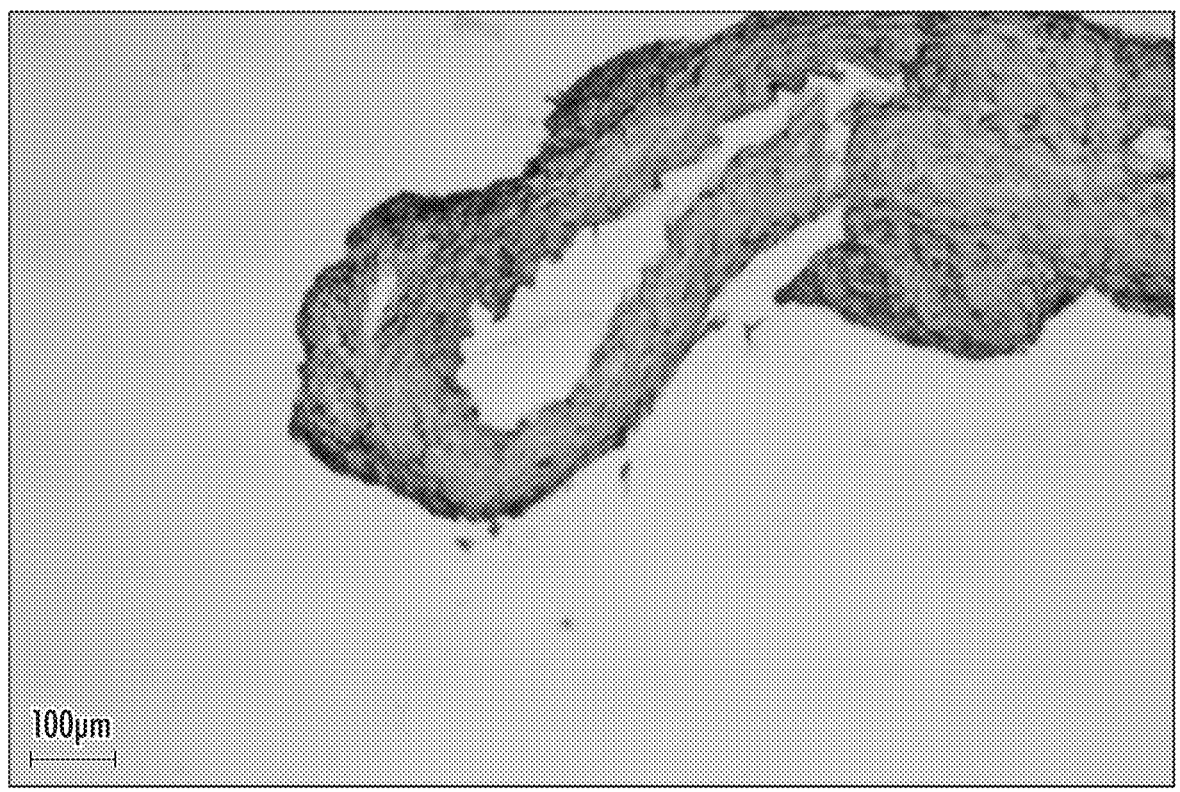
FIG. 10 illustrates IHC staining of tissue from an AngII aneurysm model in mouse aorta using an antibody as disclosed herein as the primary antibody of the protocol.
Figure 12:
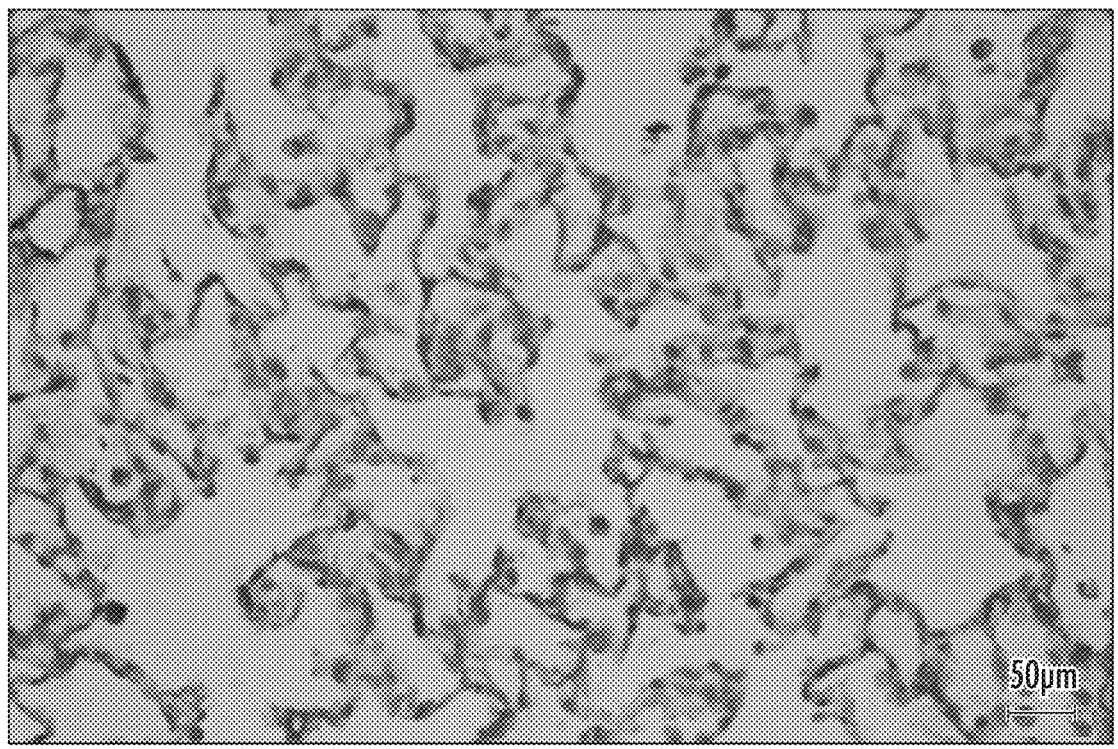
FIG. 12 illustrates IHC staining of tissue from an elastase emphysema model in rat lungs using an antibody as disclosed herein as the primary antibody of the protocol.
Figure 13:
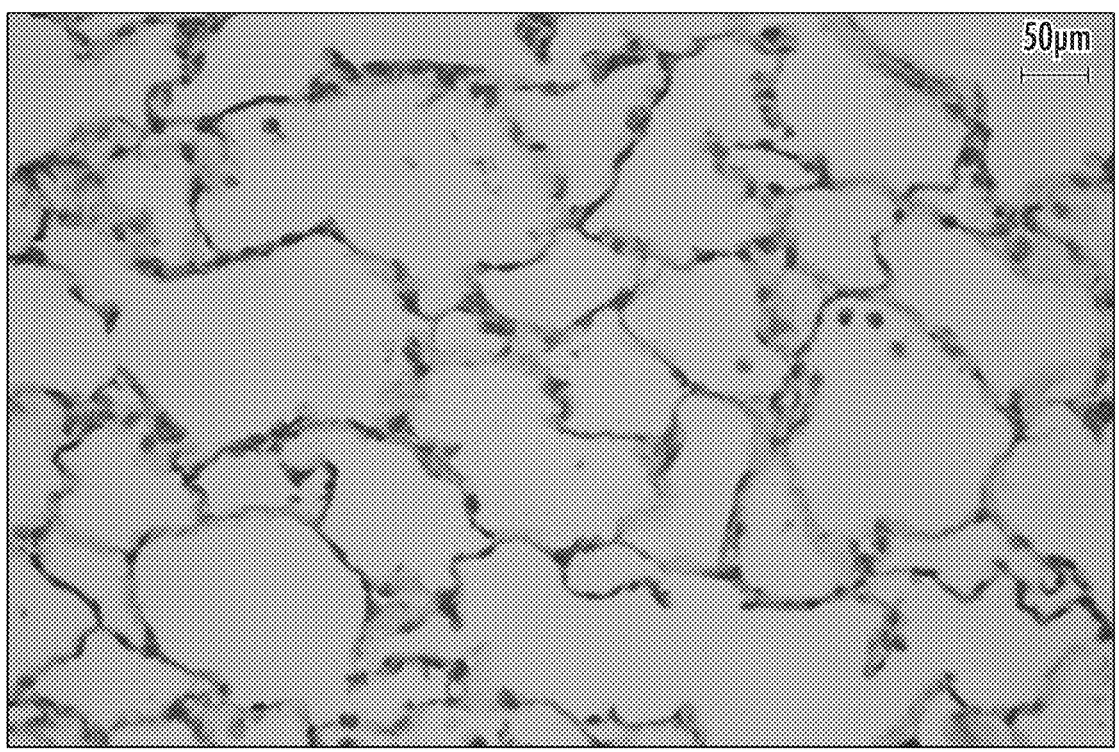
FIG. 13 illustrates IHC staining of tissue from an elastase emphysema model in rat lungs using a secondary antibody as control.
Figure 14:
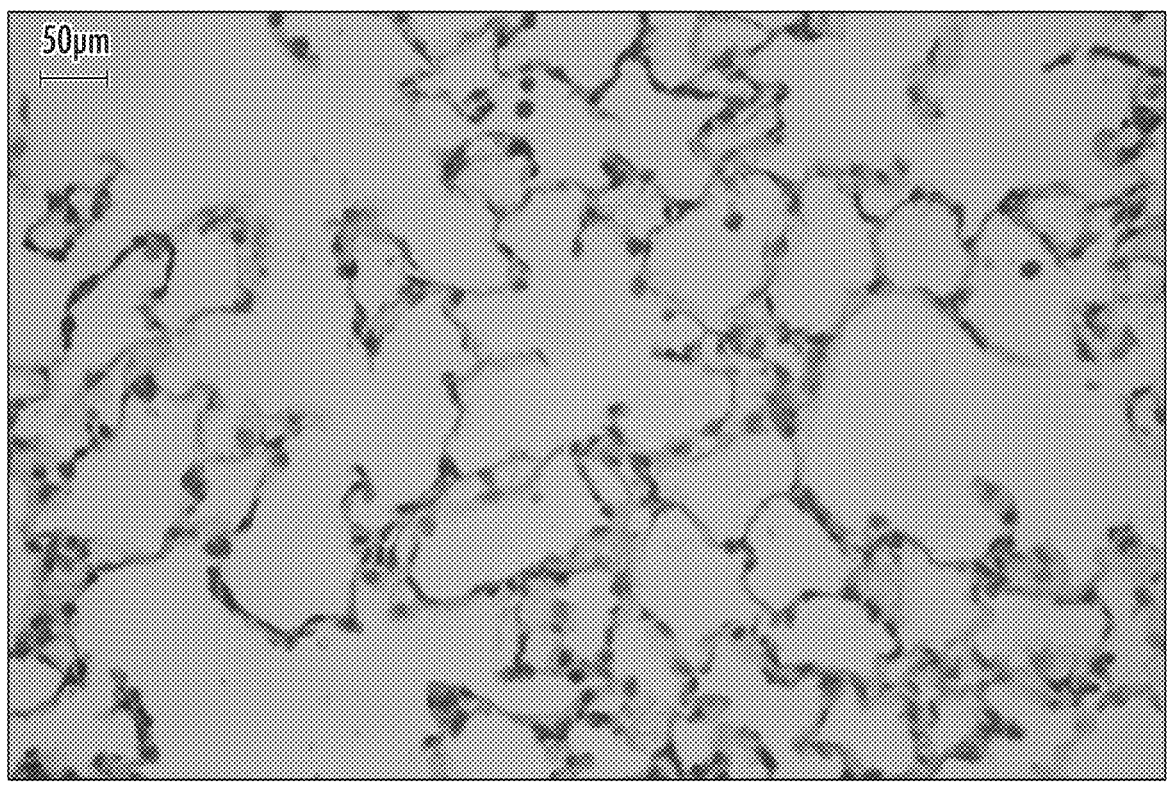
FIG. 14 illustrates IHC staining of tissue from an elastase emphysema model in rat lungs using a secondary antibody as control.

FIG. 8 and FIG. 12 illustrate lung tissues from the emphysema model in rat tissue following incubation with the antibody raised against SEQ ID NO: 1. FIG. 13 and FIG. 14 show lung tissues from the emphysema rat model following incubation with the control antibody. As can be seen, the antibody to SEQ ID NO: 1 showed excellent bonding to the damaged tissue.

Example 4

Figure 15:
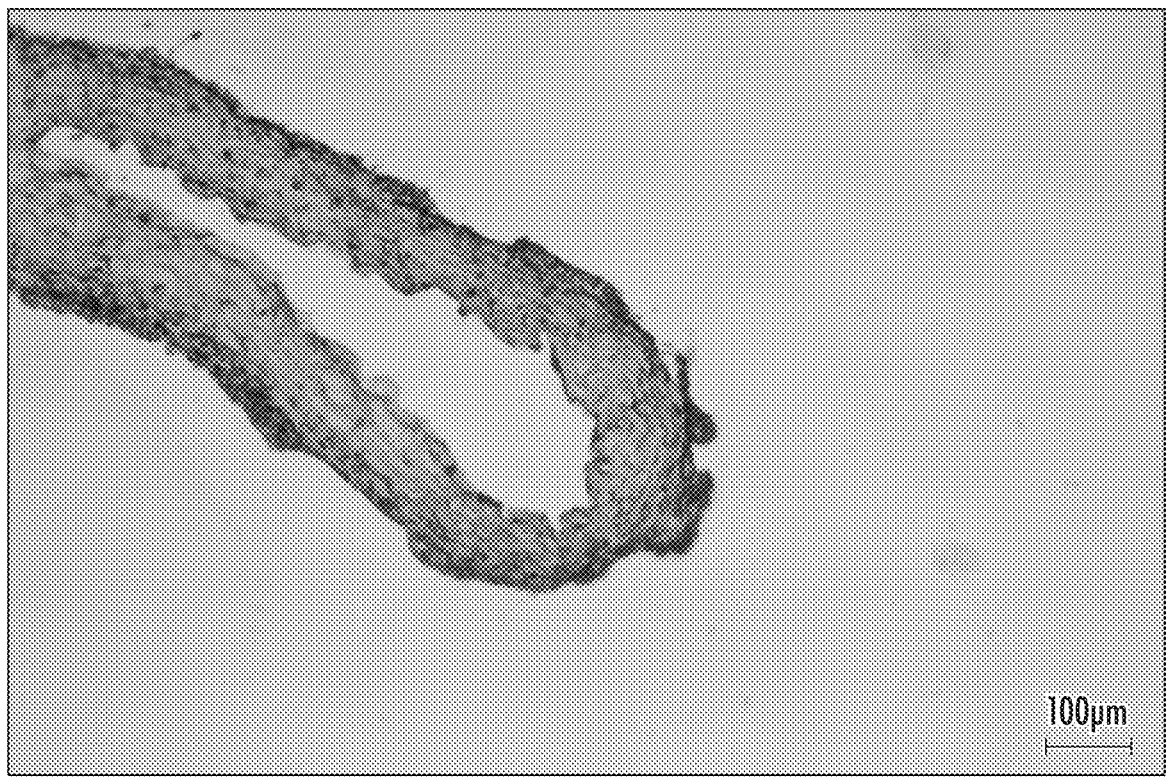
FIG. 15 illustrates IHC staining of tissue from an AngII aneurysm model in mouse aorta using an antibody as disclosed herein as the primary antibody of the protocol.
Figure 16:
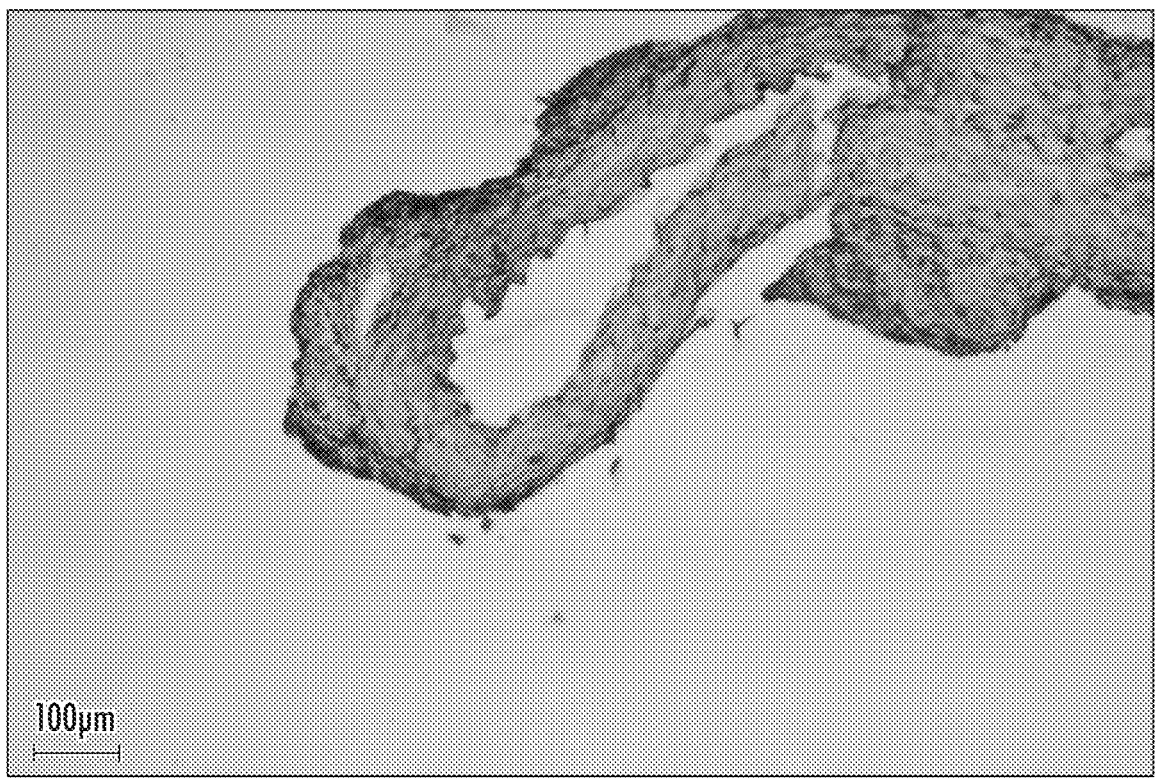
FIG. 16 illustrates IHC staining of tissue from an AngII aneurysm model in mouse aorta using an antibody as disclosed herein as the primary antibody of the protocol.

Mice were anesthetized and osmotic pumps filled with angiotensin were placed in subcutaneous pockets made perpendicular to the spine of the animals. Two weeks later, the animals spontaneously developed aneurysm in their aorta. A portion of aorta containing elastin damage was processed and embedded in paraffin. Five-micron thick sections were made, and immunohistochemistry was performed using a monoclonal antibody (mAb) RE2 raised against SEQ ID NO: 1 as primary antibody using IHC kit (Enzo Life Sciences, Inc.). IHC for paraffin-embedded sections were performed according to manufacturer's protocol. Concentration of antibody was maintained at 10 µg/mL for all experiments. Examples of the mice aortae are illustrated in FIG. 15 and FIG. 16. As can be seen by the dark areas in the images, the antibody bonded to the degraded elastin.

Example 5

Lung tissues shown in FIGS. 17-20 were obtained from eight-week old male C57BL/6 mice that received an intra-tracheal injection of 0.50 U porcine pancreatic elastase (PPE) (Elastin Products Company Inc., Owensville, MO) dissolved in phosphate buffered saline (PBS) and filter sterilized. The elastase treated mice developed elastin damage over four weeks. Animals were euthanized and aortae were explanted after flushing the whole body with saline. A portion of lungs was processed and embedded in paraffin. Five-micron thick sections were made, and immunohistochemistry was performed using mAb RE2, a monoclonal antibody raised against SEQ ID NO: 1 as primary antibody with various tissues using IHC kit (Enzo Life Sciences, Inc.). IHC for paraffin embedded sections were performed according to manufacturer's protocol. Concentration of mAb RE2 was maintained at 10 µg/mL for all experiments.

Figure 17:
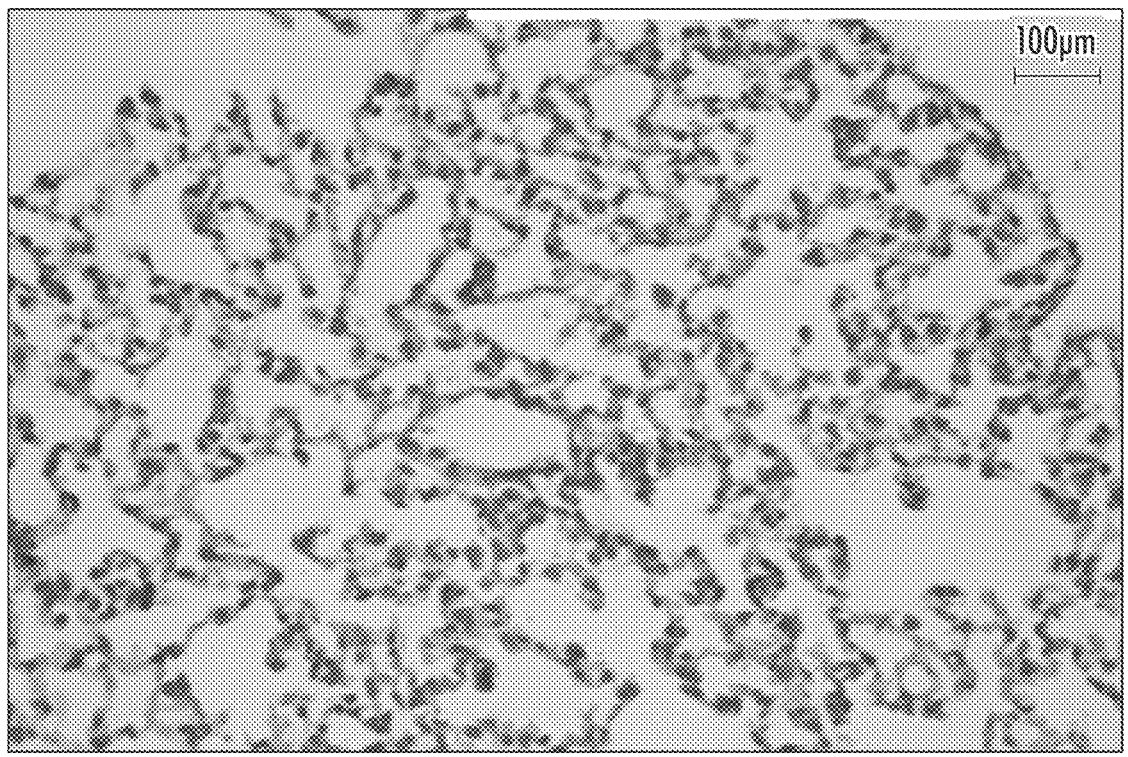
FIG. 17 illustrates IHC staining of tissue from an AngII aneurysm model in mouse aorta using an antibody as disclosed herein as the primary antibody of the protocol.
Figure 18:
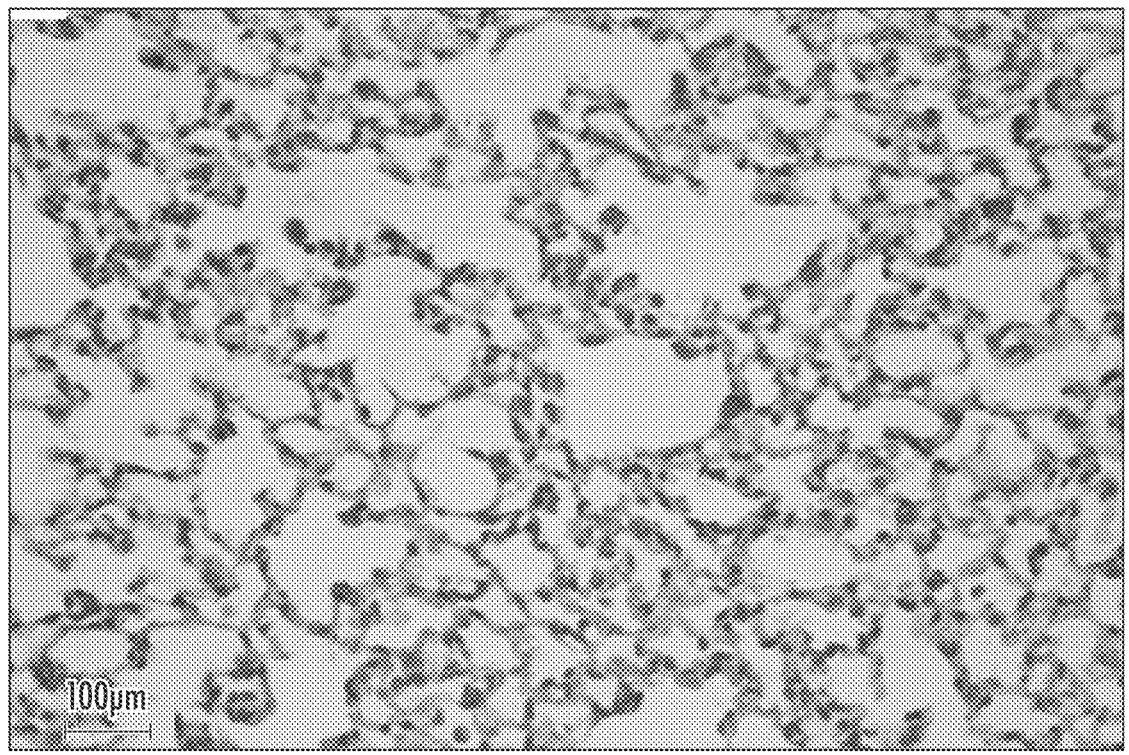
FIG. 18 illustrates IHC staining of tissue from an AngII aneurysm model in mouse aorta using an antibody as disclosed herein as the primary antibody of the protocol.
Figure 19:
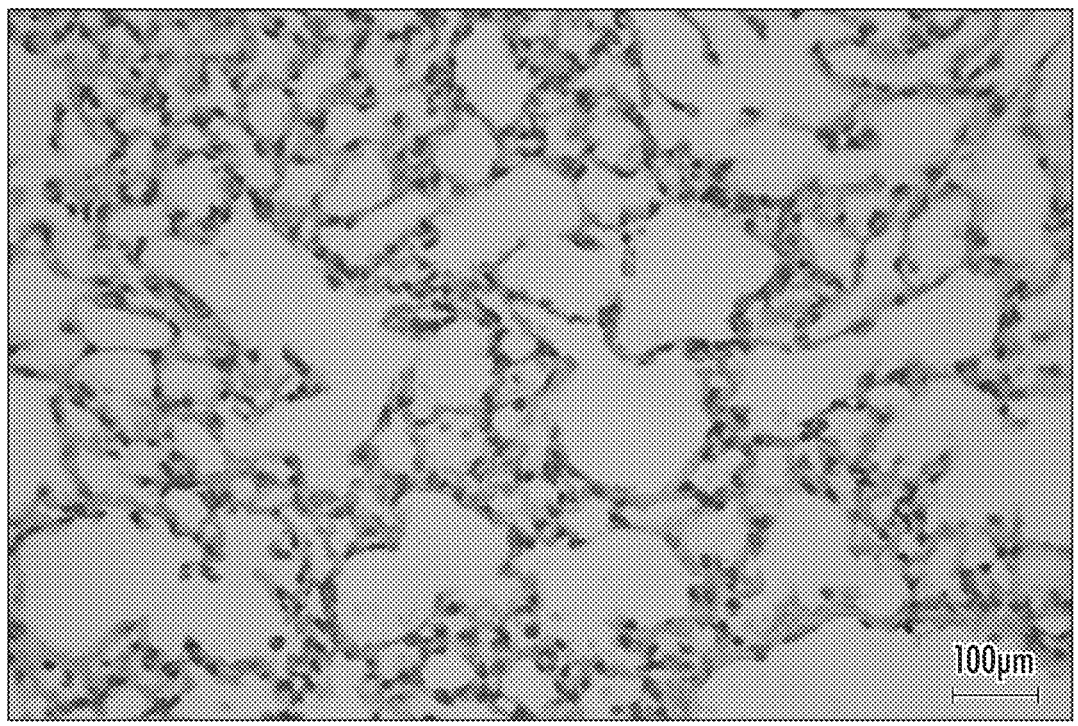
FIG. 19 illustrates IHC staining of tissue from an AngII aneurysm model in mouse aorta using a secondary antibody as control.
Figure 20:
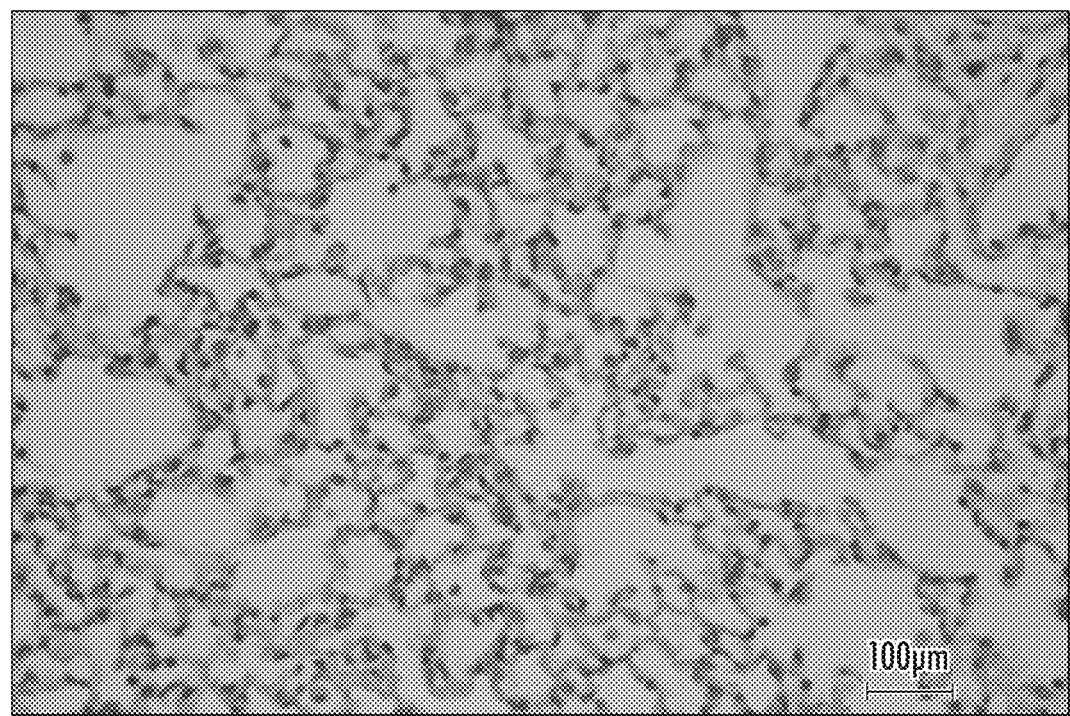
FIG. 20 illustrates IHC staining of tissue from an AngII aneurysm model in mouse aorta using a secondary antibody as control.

FIG. 17 and FIG. 18 illustrate the sections with IHC performed the antibody raised against SEQ ID NO: 1, and FIG. 19 and FIG. 20 illustrate sections with IHC performed with the control antibody. As can be seen, the antibody against SEQ ID NO: 1 strongly bonded to the damaged tissue.

Example 6

Figure 21:
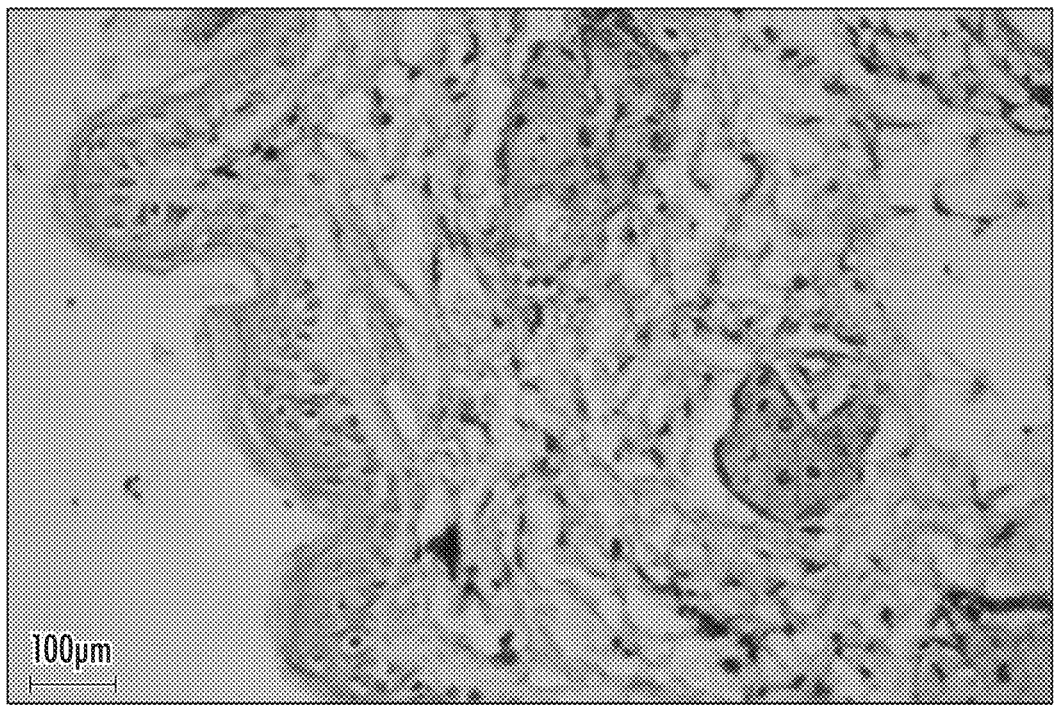
FIG. 21 illustrates IHC staining of elastase treated mouse skin using an antibody as disclosed herein as the primary antibody of the protocol.
Figure 22:
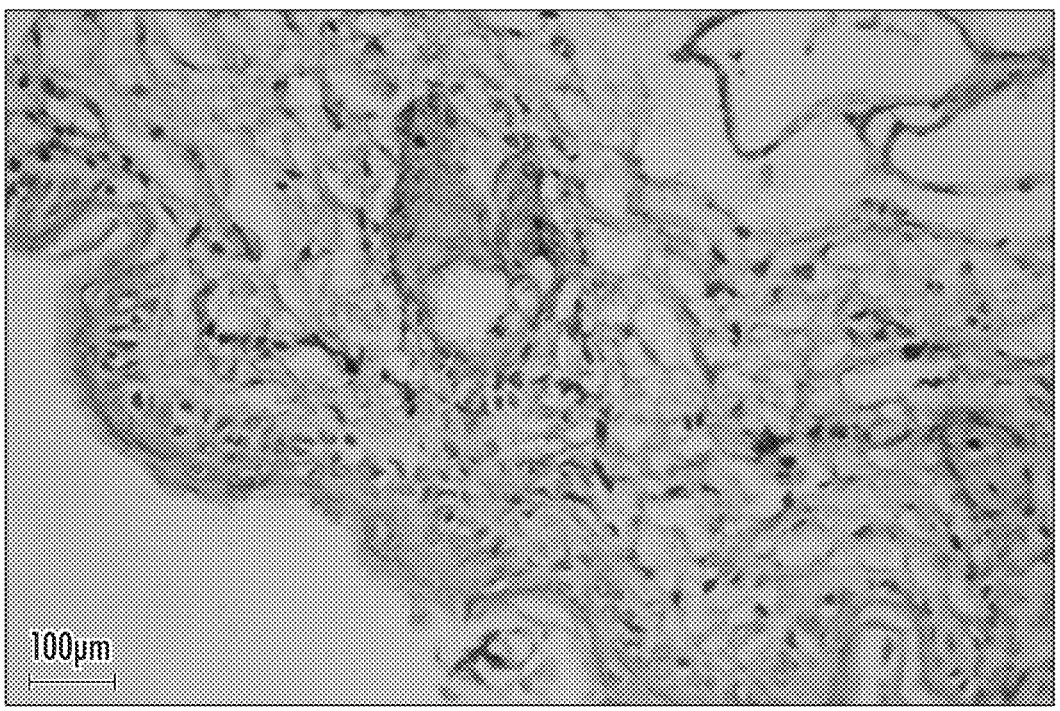
FIG. 22 illustrates IHC staining of elastase treated mouse skin using an antibody as disclosed herein as the primary antibody of the protocol.
Figure 23:
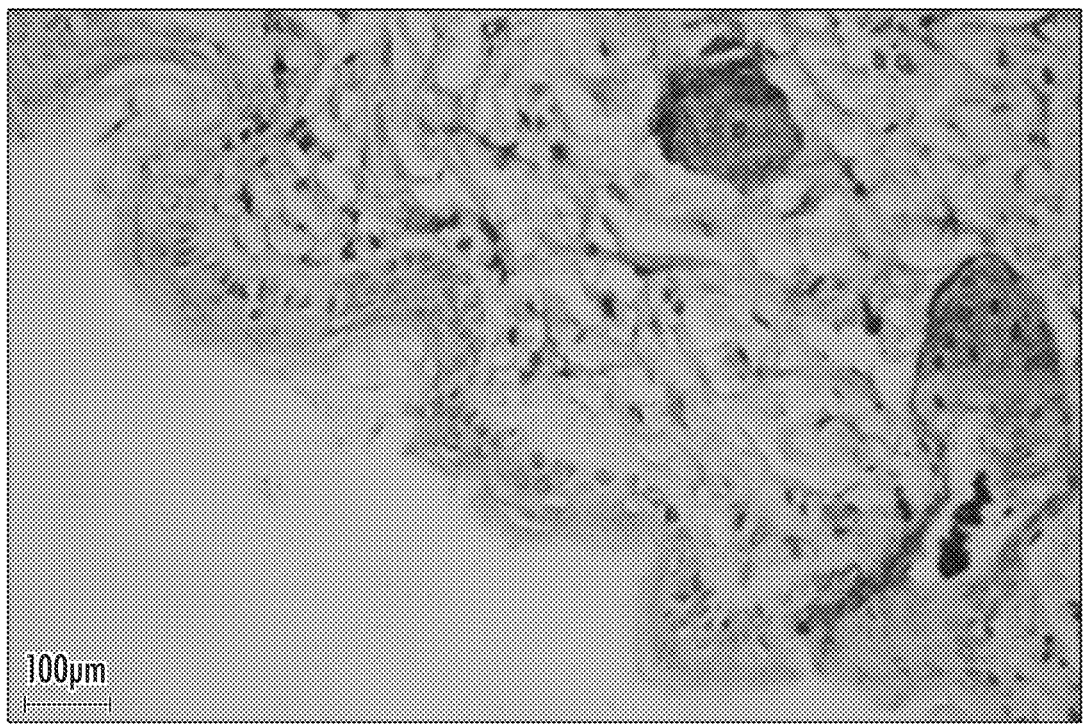
FIG. 23 illustrates IHC staining of elastase treated mouse skin using a secondary antibody as control.
Figure 24:
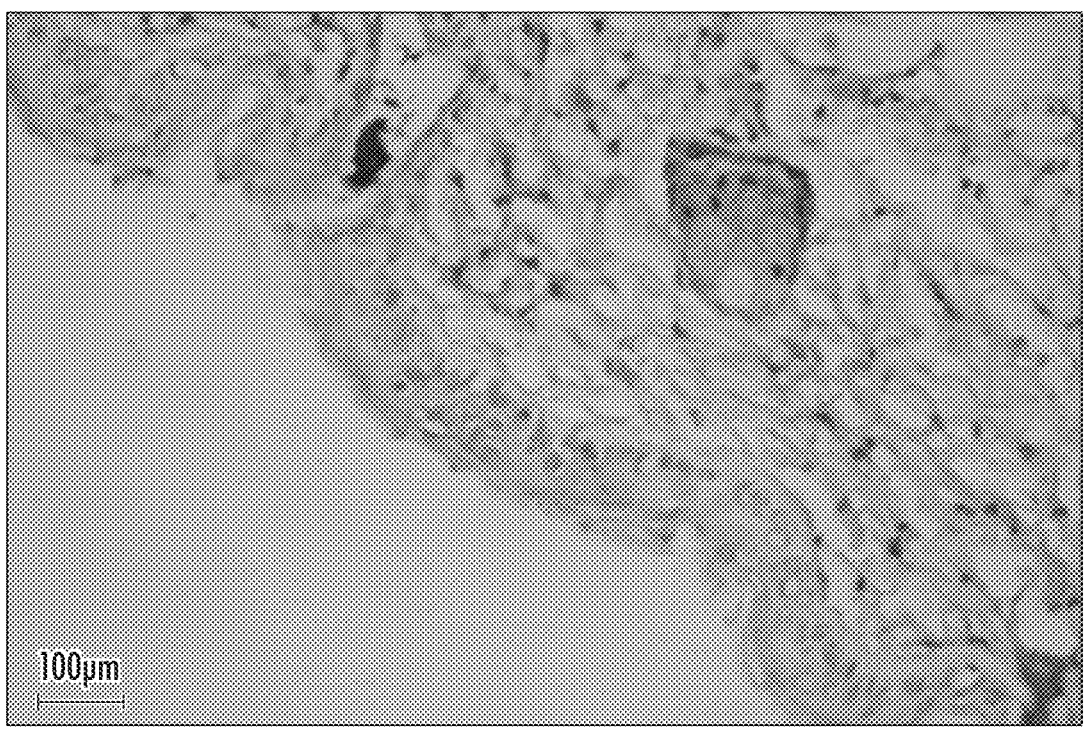
FIG. 24 illustrates IHC staining of elastase treated mouse skin using a secondary antibody as control.

Skin tissues were obtained from 8-week old hairless strain of mice. Animals' skins were divided into quadrants and porcine pancreatic elastase (30 U) dissolved in phosphate buffered saline and filter sterilized was injected intradermally. This was repeated after two weeks and after four weeks. Elastin in the skin was damaged due to the elastase activity. Animals were euthanized and skin was carefully collected and frozen. The skin samples were later processed and embedded in paraffin. Five-micron thick sections were made, and immunohistochemistry was done using mAb RE2 antibody as primary antibody (FIGS. 21 and 22) using IHC kit (Enzo Life Sciences, Inc.). FIG. 23 and FIG. 24 illustrate the results using the control antibody. IHC for paraffin-embedded sections were performed according to manufacturer's protocol. Concentration of the antibody was maintained at 10 µg/mL for all experiments.

Example 7

Figure 25:
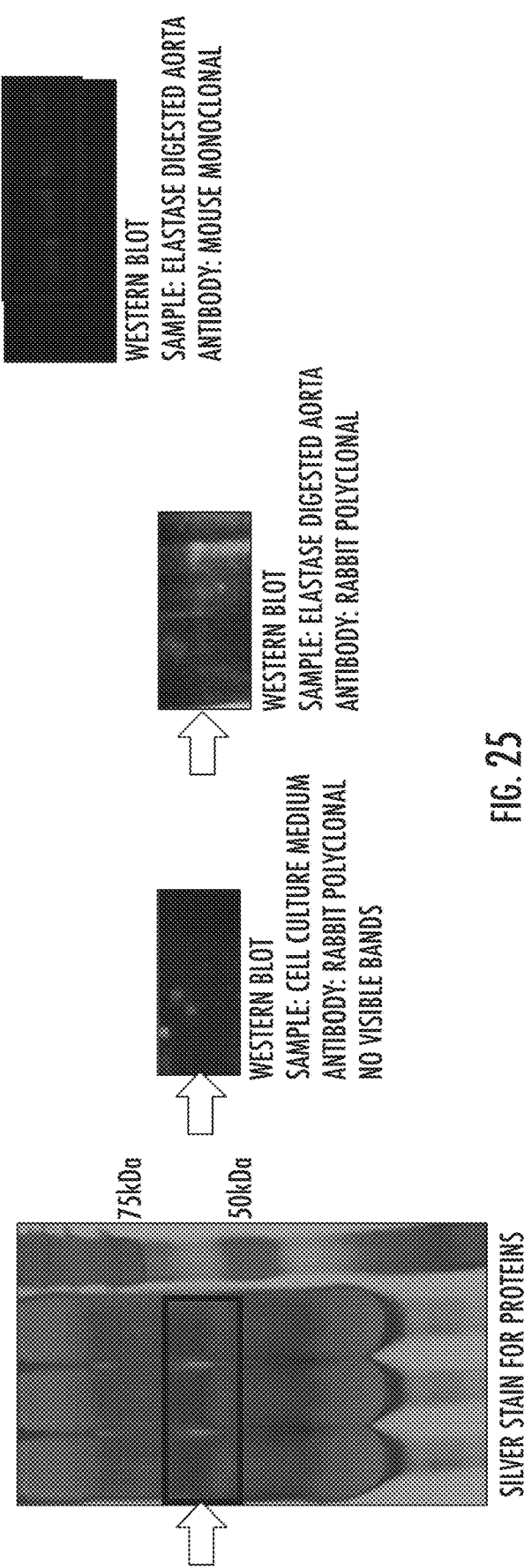
FIG. 25 illustrates silver staining and Western blot results in detection of binding between disclosed antibodies and soluble tropoelastin.

Western blot and silver staining were used to detect binding of disclosed antibodies with tropoelastin. Cell culture medium, alpha elastin standard, and supernatant solution from elastase digested rat aorta were used to test for detection of elastin by monoclonal antibody raised against SEQ ID NO: 1 and mouse monoclonal elastin antibody raised as control (a monoclonal antibody produced from mouse before hybridomas). Silver stain (FIG. 25) showed soluble elastin in between 75 kDa and 50 kDa protein markers but neither of the antibodies could detect the soluble elastin. When elastase-digested aorta sample was used, rabbit polyclonal antibody displayed a band around 50 kDa protein marker. Mouse monoclonal had a very specific single band above 150 kDa marker with elastase-digested aorta sample but not cell culture medium.

Example 8

A monoclonal IgG1 isotype antibody was formed against the human elastin sequence SEQ ID NO: 3 (PGGYGLPY-TTGKLPYGYP).

Figure 26:
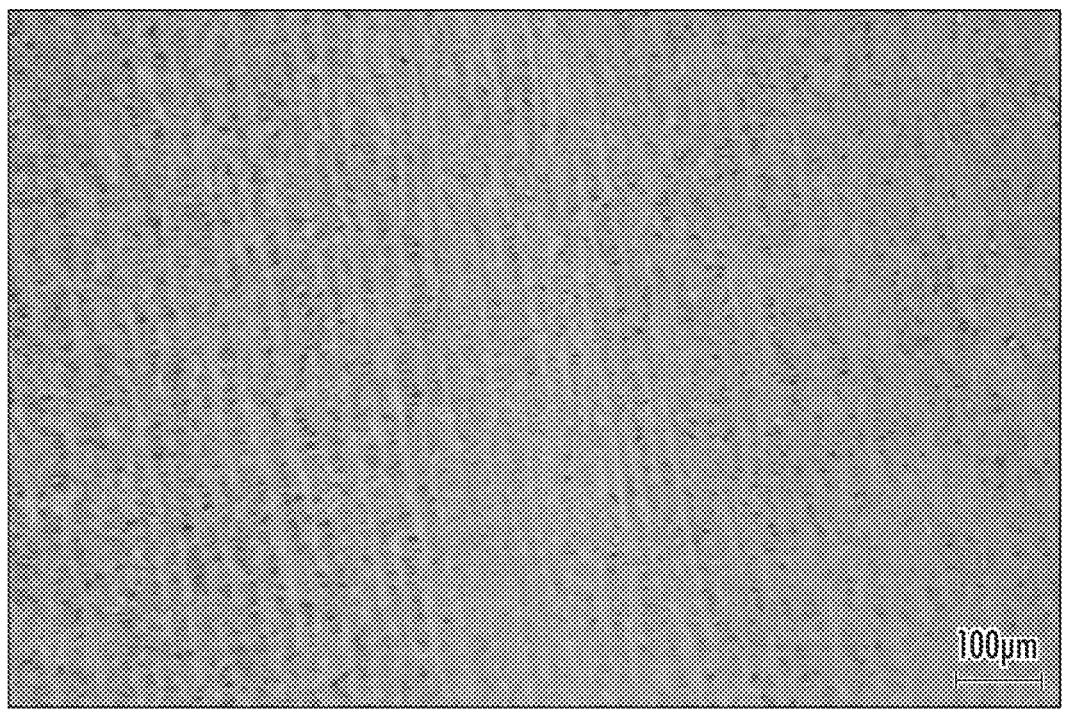
FIG. 26 illustrates IHC of H&E staining of human aorta with disclosed antibody.
Figure 27:
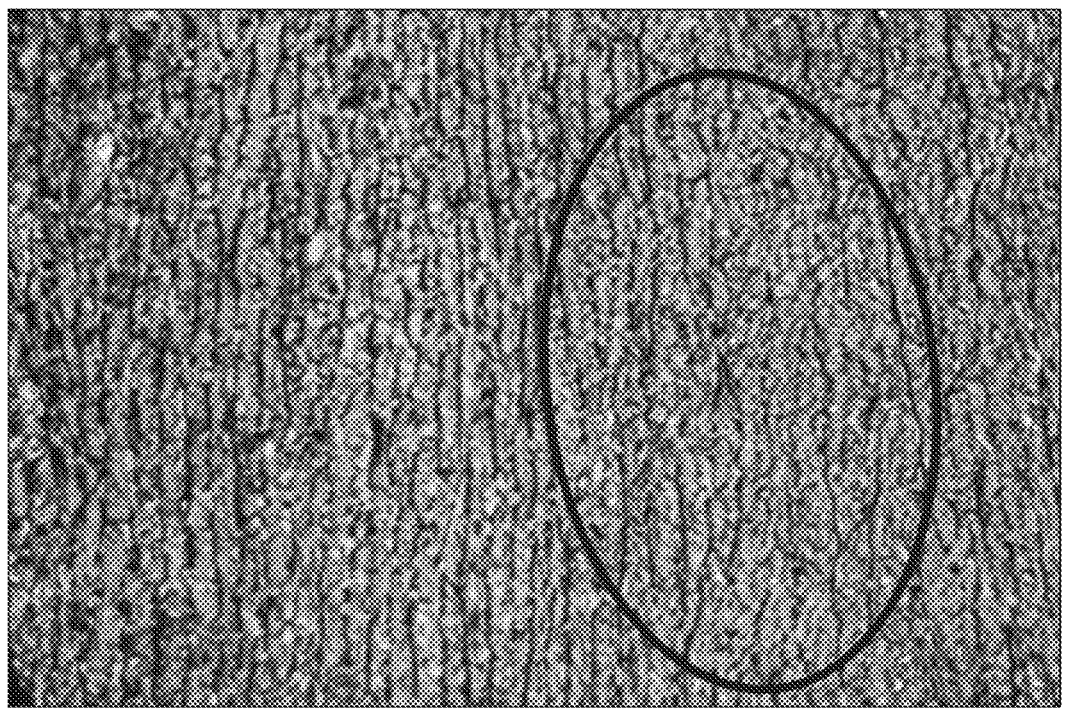
FIG. 27 shows Verhoeff van Gieson (VVG) staining of human aorta with mild aneurysm degradation.
Figure 28:
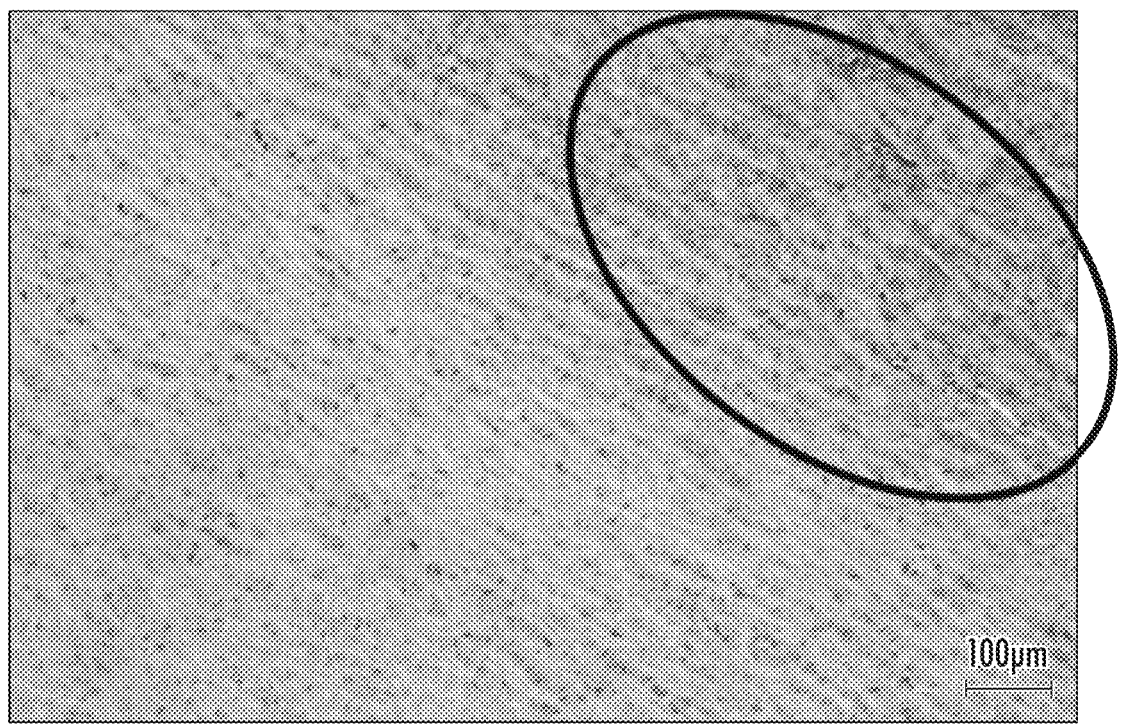
FIG. 28 shows binding of an antibody as described to the damaged tissue of FIG. 27.
Figure 29:
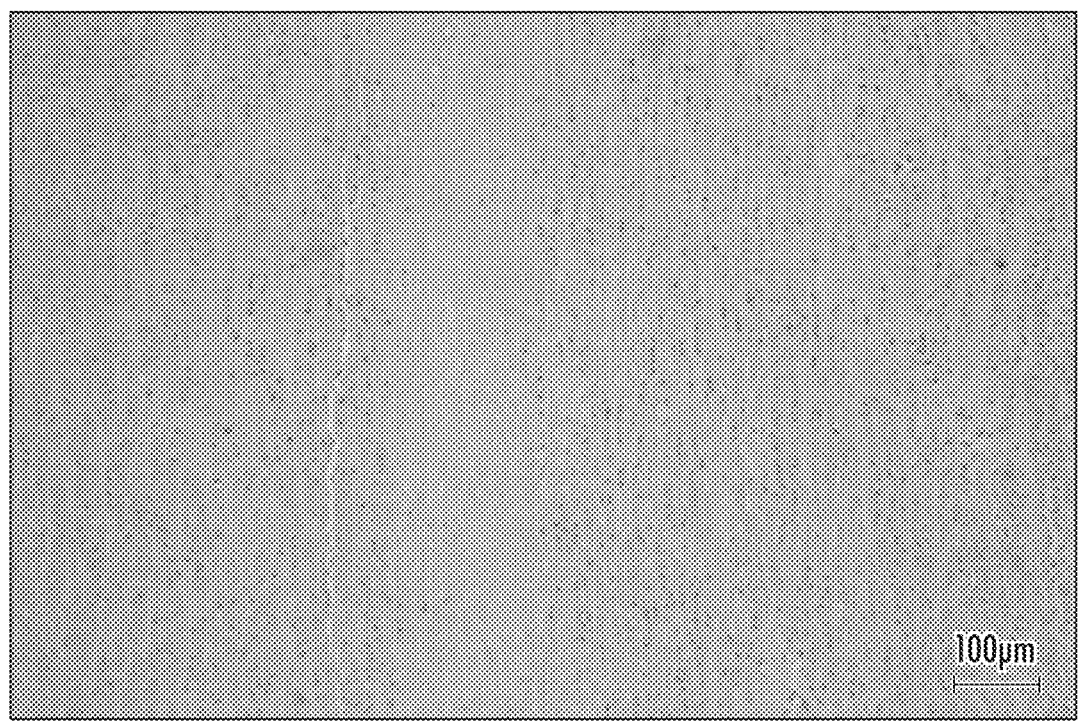
FIG. 29 shows a lack of binding to the human aorta tissue when using a control antibody.

IHC using H&E staining (FIG. 26) showed specificity for degraded elastin in human aorta with mild aneurysm. Circled portion in VVG staining for elastin (FIG. 27) showed degradation of elastin and the same area showed antibody binding to the section (FIG. 28). The control secondary antibody only showed no signal (FIG. 29).

Figure 30:
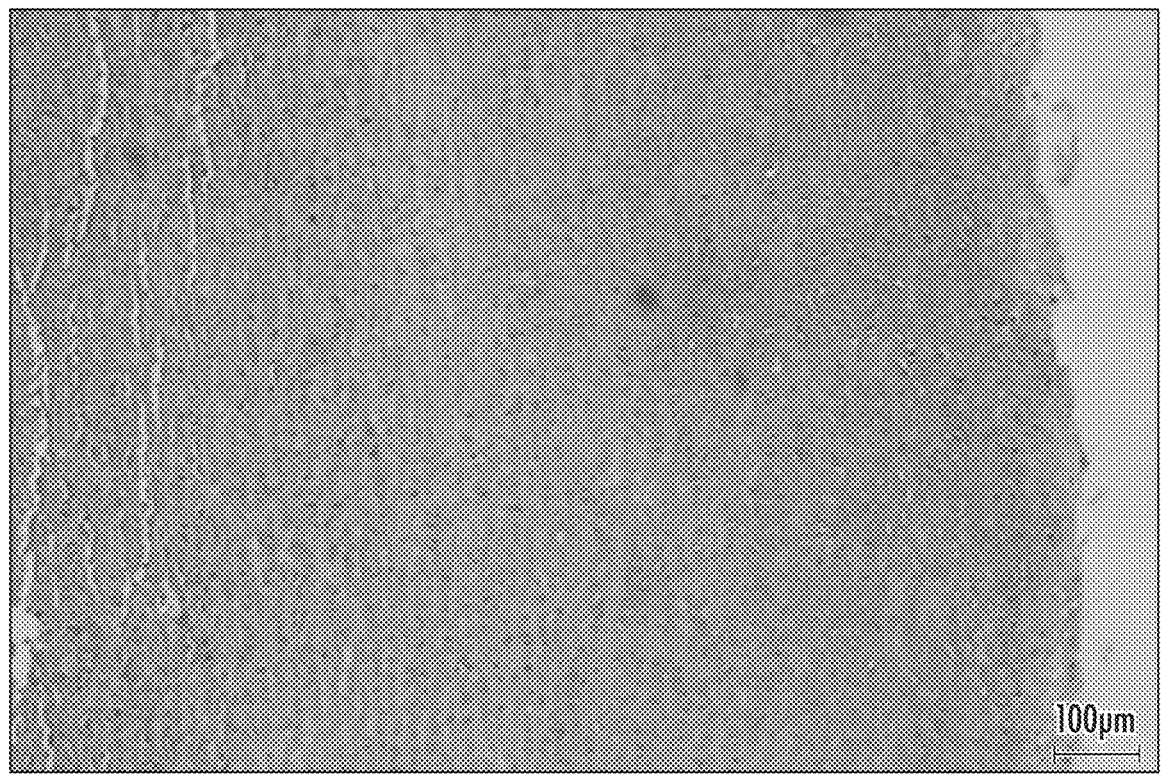
FIG. 30 illustrates IHC of H&E staining of human aorta with disclosed antibody.
Figure 31:
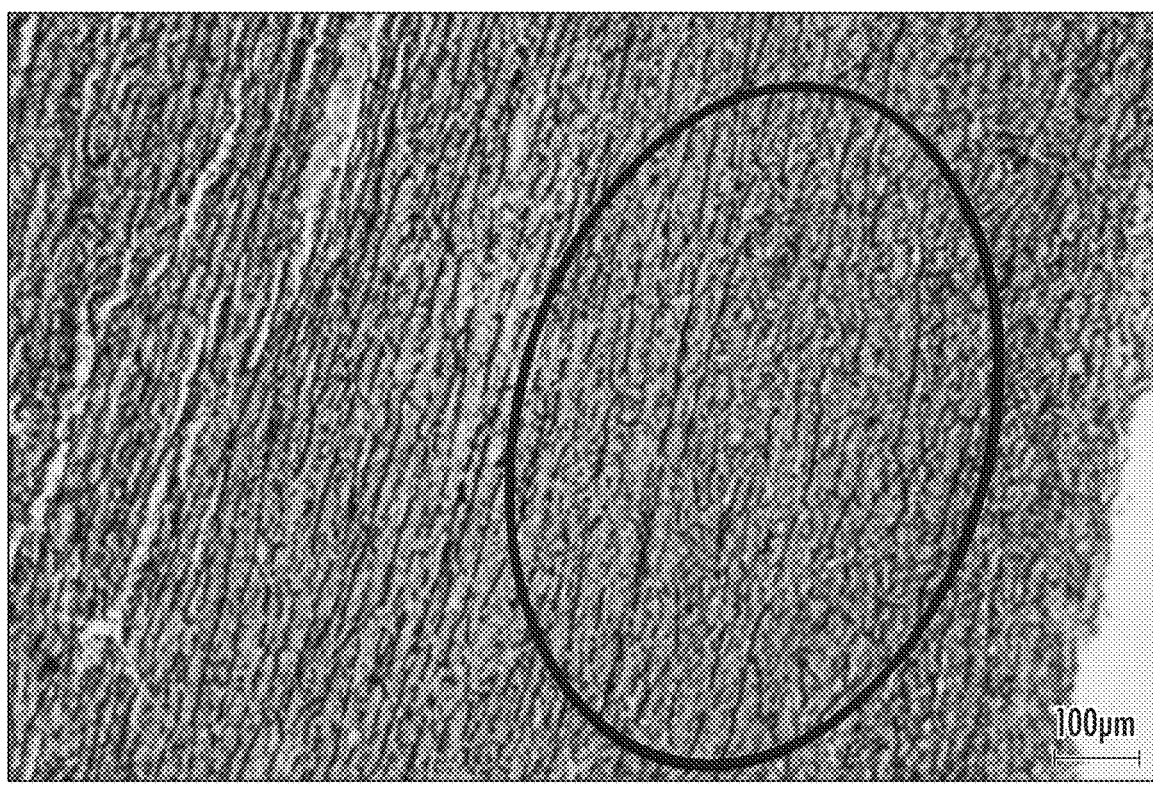
FIG. 31 shows Verhoeff van Gieson (VVG) staining of human aorta with mild aneurysm degradation.
Figure 32:
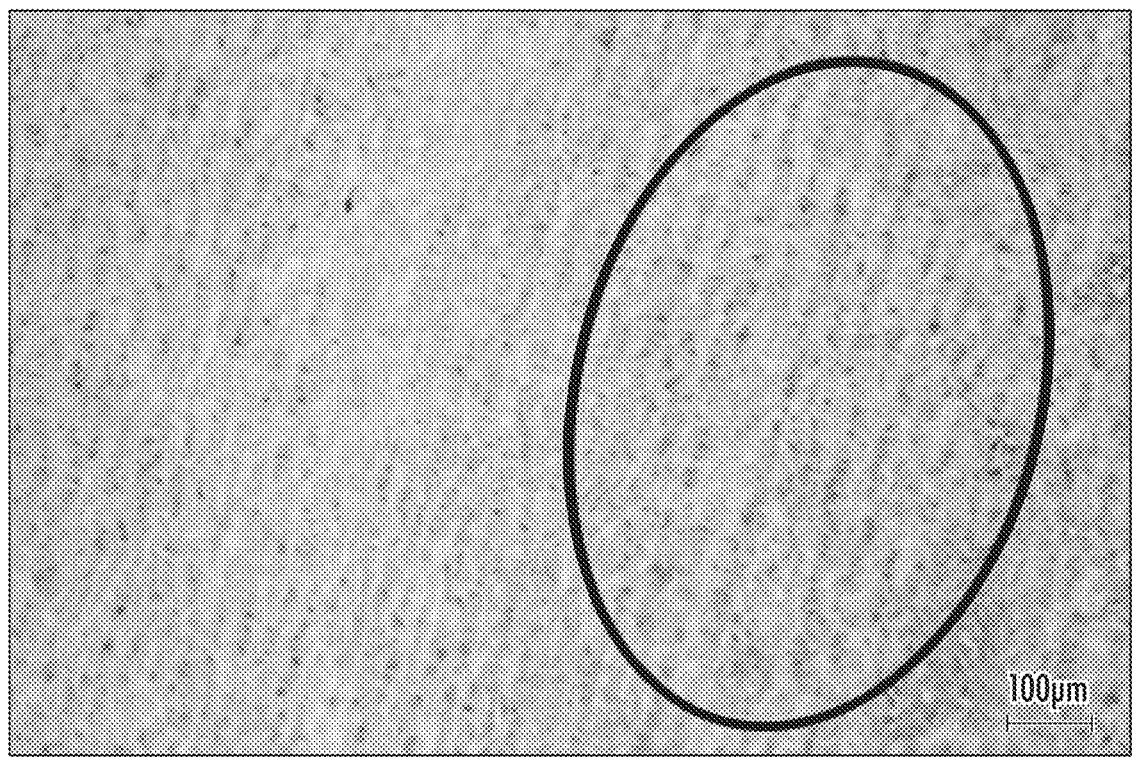
FIG. 32 shows binding of an antibody as described to the damaged tissue of FIG. 27.
Figure 33:
FIG. 33 shows a lack of binding to the human aorta tissue when using a control antibody.

IHC using H&E staining (FIG. 30) showed specificity for degraded elastin in human aorta with mild aneurysm. Circled portion in VVG staining for elastin (FIG. 31) showed degradation of elastin and the same area showed antibody binding to the section (FIG. 32). The control secondary antibody only showed no signal (FIG. 33).

Example 9

Figure 34:
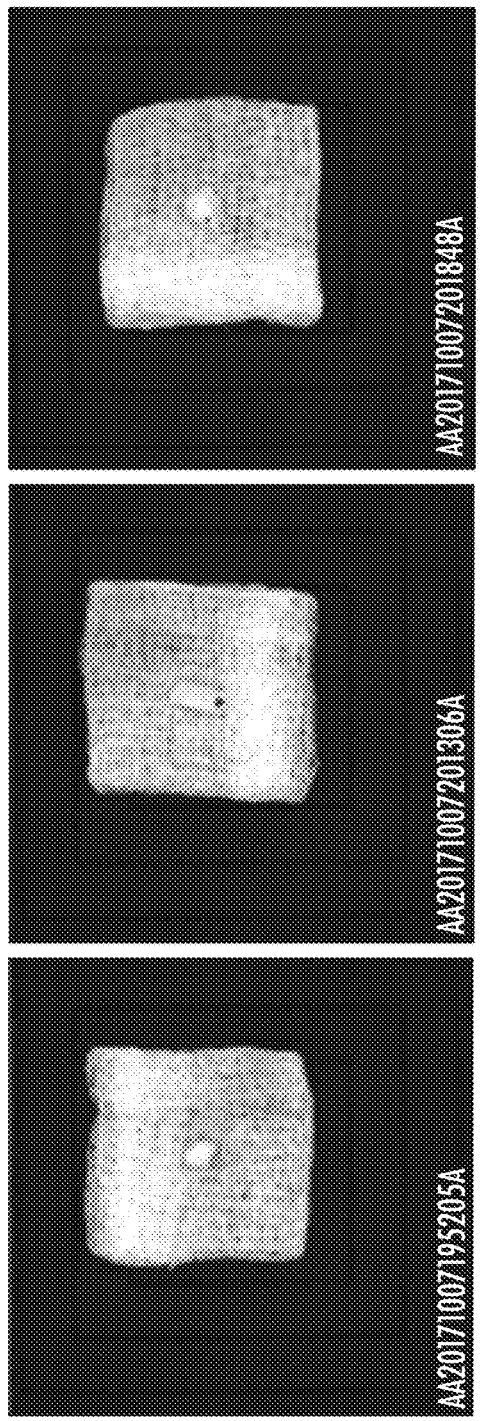
FIG. 34 illustrates binding of disclosed antibodies to atherosclerotic plaque (CEA) in an ex vivo targeting protocol.
Figure 34:
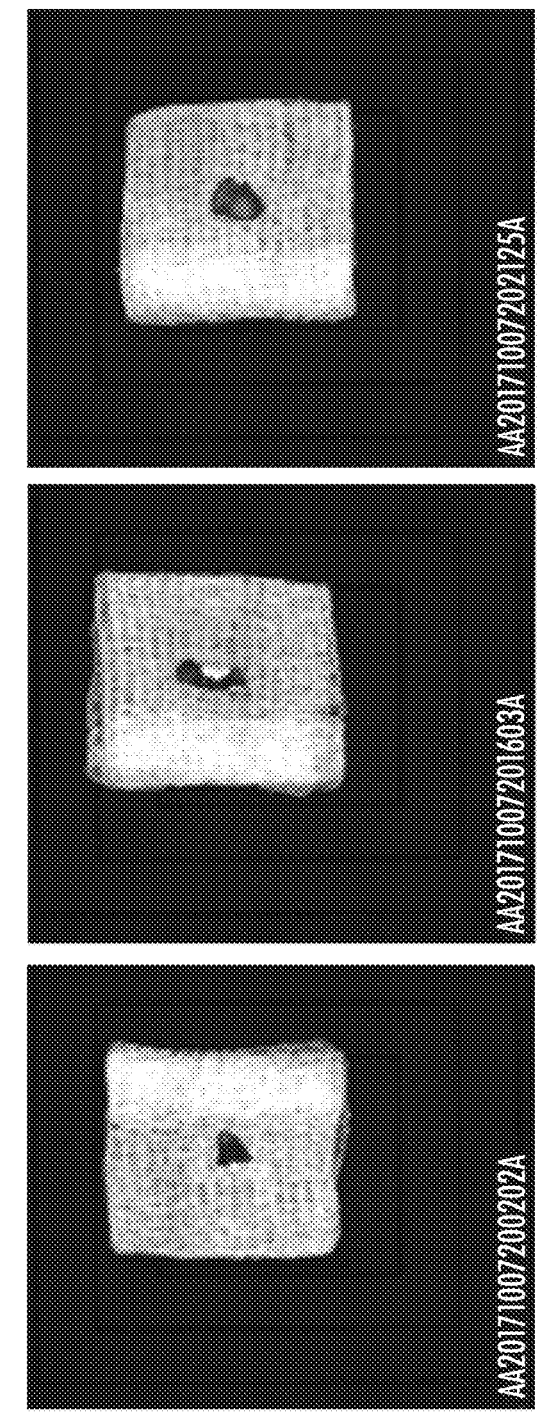

Fresh human carotid endarterectomy artery (CEA) samples were separated into two parts: One part was used for targeting with DIR-NPs loaded with antibody raised against SEQ ID NO: 3 (ELN group), and the other part was used for targeting with DiR-NPs without elastin antibody (control group). The samples were incubated at 4° C. for 12 hours. The samples were then washed with PBS, and nanoparticle attachment was tested with IVIS. The IVIS results (FIG. 34) showed that ELN conjugated DiR-NPs were attached to degraded and immature elastin in the artery while control NPs without antibody were not attached.

Figure 35:
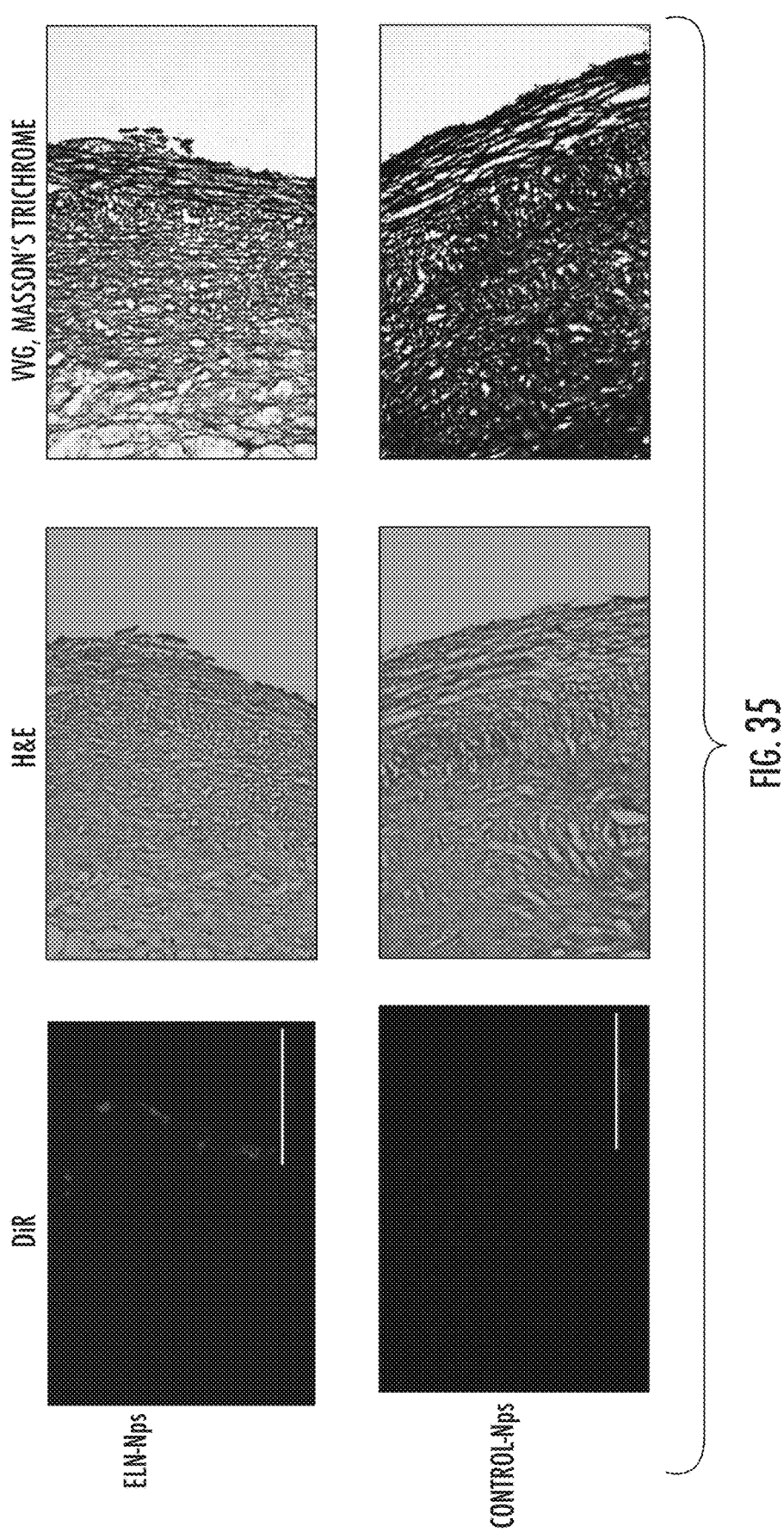
FIG. 35 demonstrates illustrates IHC including direct examination of dye loaded particles, H&E staining, and VVG staining showing binding of disclosed antibodies to elastin in atherosclerotic plaque of human aorta.
Figure 36:
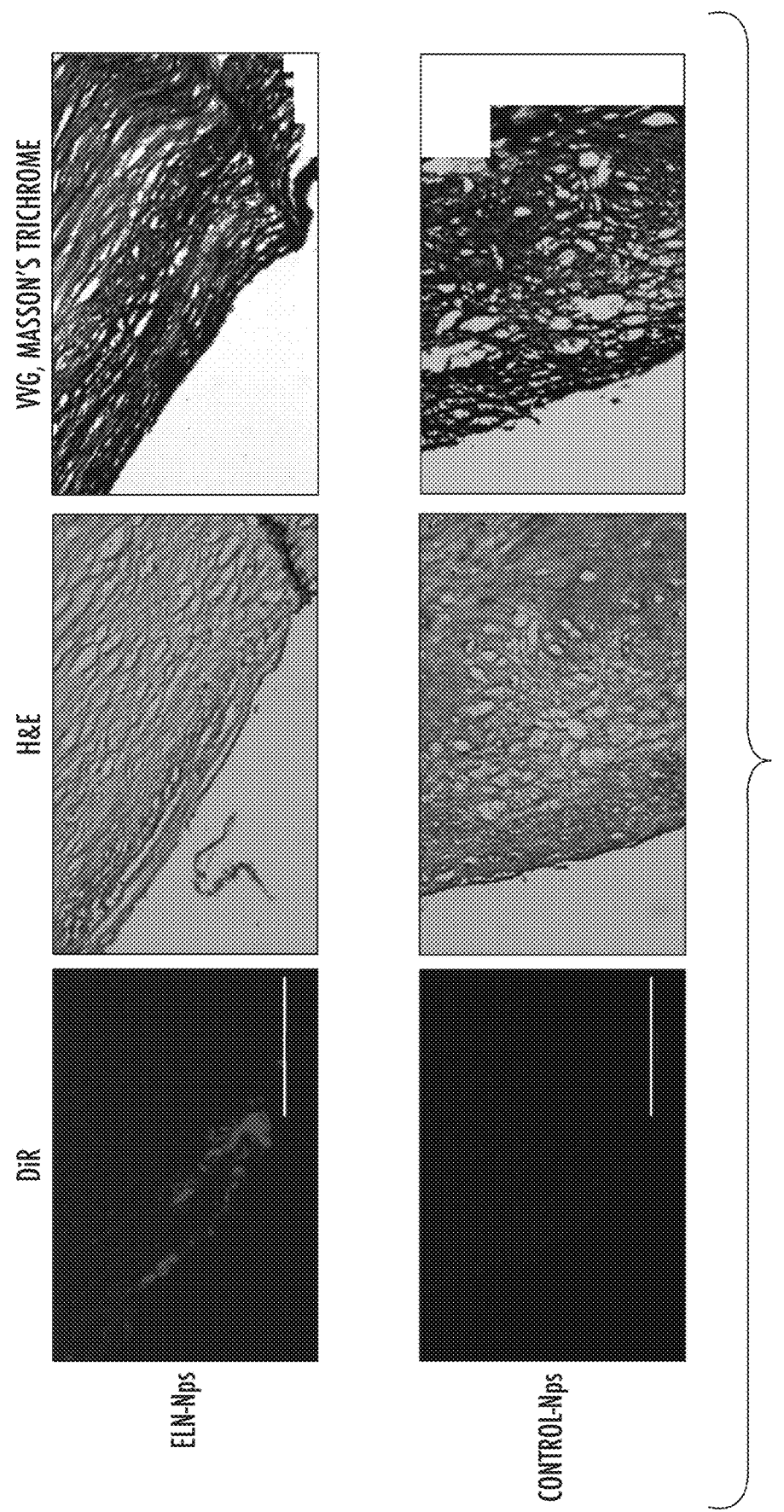
FIG. 36 demonstrates illustrates IHC including direct examination of dye loaded particles, H&E staining, and VVG staining showing binding of disclosed antibodies to elastin in atherosclerotic plaque of human aorta.

The samples then underwent decalcification for histology preparation and were embedded in OCT® to obtain frozen sections for staining. As demonstrated in FIG. 35 and FIG. 36, targeting of nanoparticles to the elastin in atherosclerosis was seen by direct examination (left panels), H&E staining (middle panels), and VVG staining (right panels). Control NPs without the antibody (bottom panels) were not targeted.

Example 10

Hybridomas expressing a monoclonal IgG1 isotype antibody formed against the human elastin sequence SEQ ID NO: 3 were characterized. Total RNA was isolated from hybridoma cells following the technical manual of TRIzol® Reagent. Total RNA was then reverse-transcribed into cDNA using either isotype-specific anti-sense primers or universal primers following the technical manual of PrimeScript™ 1st Strand cDNA Synthesis Kit. Antibody fragments of $V_H$, $V_L$, $C_H$ and $C_L$ were amplified according to the standard operating procedure of rapid amplification of cDNA ends (RACE) of GenScript®. Amplified antibody fragments were cloned into a standard cloning vector separately. Colony PCR was performed to screen for clones with inserts of correct sizes. No less than five colonies with inserts of correct sizes were sequenced for each fragment. The sequences of different clones were aligned, and a consensus sequence was obtained.

Figure 37:
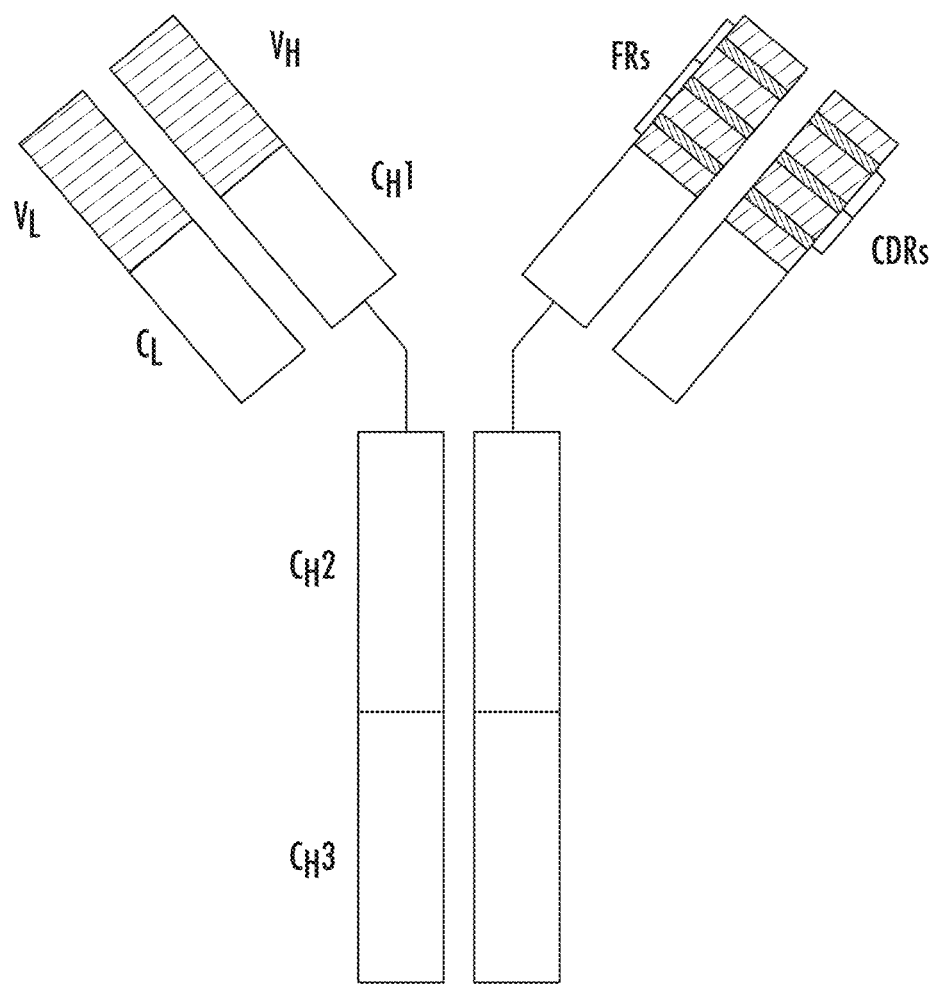
FIG. 37 schematically illustrates a monoclonal antibody as described herein.

FIG. 37 schematically illustrates the monoclonal antibody. The isotype was mouse IgG/kappa, as analyzed by the sequences of the constant region. For the consensus sequence, five clones were sequenced for the $V_H$, $C_H$, $V_L$, and $C_L$ sequences, all with greater than 99% sequence identity. The IMGT Analysis of V(D)J junctions is provided in Table 1, below. All variable sequences were productive, and no D segments were detected.

TABLE 1

| Sequence | V-GENE and Allele | V-Region (identity % (nt) | J-Gene and Allele | AA Junction | Junction Frame |
|---|---|---|---|---|---|
| $V_H$ | Musmus IGHV9-3-1*01F | 96.53% (278/288 nt) | Musmus IGHJ2*01F | CAREDYW | In-frame |
| $V_L$ | Musmus IGKV1-135*01F | 98.64% (290/294 nt) | Musmus IGKJ1*01F | CWQGTHFPWTF | In-frame |

SEQ ID NO: 4 provides the complete DNA sequence and SEQ ID NO: 5 provides the complete amino acid sequence for the heavy chain of the monoclonal antibody. SEQ ID NO: 6 (nt) and SEQ ID NO: 7 (aa) provide the sequences for the variable region of the heavy chain, with the CDR and FR regions described in SEQ ID NOs: 8-21. SEQ ID NO: 22 provides the complete DNA sequence, and SEQ ID NO: 23 provides the complete amino acid sequence for the light chain of the monoclonal antibody. SEQ ID NO: 24 (nt) and SEQ ID NO: 25 (aa) provide the sequences for the variable region of the light chain, with the CDR and FR regions described in SEQ ID NOs: 26-39.

Example 11

Citrate capped gold nanoparticles (GNPs) were purchased from Meliorum Technologies, Rochester, NY) with an average size of 150±25 nm. A heterobifunctional thiol-PEG-acid (SH-PEG-COOH) (2000MW, Nanocs, New York, NY) was added to the GNPs at a weight ratio of 4:1 and the mixture was incubated at 4° C. for 48 hours with gentle rocking to achieve PEGylation. PEGylated GNPs were collected after centrifuging at 10,000 rpm for 20 minutes at room temperature and resuspended in 0.1M MES (pH: 5.5). EDC/NHS chemistry was utilized to conjugate the PEGylated GNPs with anti-elastin antibody as described herein. Briefly, EDC (N-(3-Dimethylaminopropyl)-N'-ethylcarbodiimide hydrochloride) (Oakwood Chemical, Estill, SC) and Sulfo-NHS (N-hydroxysulfosuccinimide) (Sigma Aldrich, St. Louis, MO) were added at a weight ratio of 2:1 and 4:1 separately to the PEGylated GNPs. This mixture was incubated at room temperature for 6 hours with gentle vortexing. Resulted GNPs were collected after centrifuging at 10,000 rpm for 20 minutes at room temperature and resuspended in 1 mL of PBS (pH 7.8). 4 µg anti-elastin antibody per mg GNPs was added and the mixture was incubated overnight at 4° C. under slow rocking. Excessive antibody was removed by centrifuging the resulted solution at 10,000 rpm for 20 minutes. Resultant antibody/nanoparticle conjugates (EL-GNPs) were resuspended in saline to a concentration of 3 mg/mL for injection.

Fifteen male low density-lipoprotein receptor deficient (LDLr) (−/−) mice (2 months of age, on a C57BL/6 background) were obtained from the Jackson Laboratory (Bar Harbor, ME). Eleven mice were used for aneurysm study while four other mice were used as healthy age controls. Aneurysms were induced by systemic infusion of angiotensin II (AngII, Bachem Americas Inc., Torrance, CA) in combination with a diet with saturated fat (21% wt/wt) and cholesterol (0.2% wt/wt; catalog no. TD88137; Harlan Teklad). Briefly, mice were fed with high fat diet for 1 week prior to, and 6 weeks during, AngII infusion. Osmotic pumps (Model 2004; Alzet®, Cupertino, CA) filled with AngII were implanted subcutaneously through an incision at the right back shoulder of the mice under isoflurane anesthesia. 2% to 3% isoflurane was inhaled by the mice as anesthesia throughout the surgical process. The pumping rate for AngII was set to 1000 ng/kg/min. Pumps were explanted 4 weeks after the implantation and mice were allowed to recover for 2 weeks. Disease progression was monitored with a high-frequency ultrasound machine, FUJIFILM VisualSonics® Vevo® 2100 (FUJIFILM, Toronto, ON, Canada), by utilizing a linear array probe (MS-550D, broadband frequency 22 MHz-55 MHz).

Figure 38:
FIG. 38 presents an image of a three-dimensional model formed based on a CT scan that visualizes the morphology of an aneurysmal aorta (left) and illustrates the distribution of antibody-tagged gold nanoparticles within the aorta (right).

EL-GNPs were given to the mice (n=15) as a contrast agent through a retro-orbital injection at a dosage of 10 mg/kg animal weight under 2%-3% isoflurane inhalation. Mice were euthanized 24 hours after the injections and the whole aortas (from ascending aorta to iliac bifurcation) were explanted. Surrounding connective tissue on the aortas were cleaned before micro-CT scanning. Aortas were immersed in corn oil and imaged (90 kV, 250 mAs, 300 ms, 0.2 mm Al filter) with a high performance in vivo micro-CT system (SKYSCAN 1176, Bruker, Billerica, MA). Reconstruction was carried out using the SKYSCAN Nrecon software based on Feldkamp algorithm. The reconstructed images of the aortas were visualized, and the dimensions of the aneurysms were measured using DataViewer and CTVox software. 3D maximum intensity projection (MIP) images (FIG. 38, left) were obtained to determine the distribution of EL-GNPs within the aortas, while attenuation images (FIG. 38, right) were acquired to study the intensity of the signals given by both EL-GNPs and the tissue. Signal intensity was further quantified using CTAn software.

Cryo-sectioned histological samples (5 µm) were examined with a CytoViva enhanced darkfield microscope optics system (CytoViva, Inc., Auburn, AL). The system (Olympus BX51) employs an immersion oil (Type A, nd>1.515, Cargille Brand) ultra-dark-field condenser and a 40× air Plan-FL objective with an adjustable numerical aperture from 1.2 to 1.4. Illumination was provided by a Fiber-Lite® DC-950 regulated laminator. Enhanced darkfield microscopy images (FIG. 39) were obtained using Exponent 7 software with a 2.8 gain and 53 ms exposure time to visualize the EL-GNPs. Hyperspectral imager (mounted on a microscope and controlled by Environment for Visualization for Rich Data Interpretation (VERDI) software from Exelis Visual Information Solutions, Inc.) was used to extract spectral information for mapping the EL-GNPs in the samples (FIG. 41) at an exposure time of 0.25 ms with a full field of view (643 lines). Negative control samples were imaged and analyzed to create a spectral library as reference. Mapping was achieved by applying a filtered spectral library by subtracting the negative control's spectral library from the positive control's.

Figure 40:
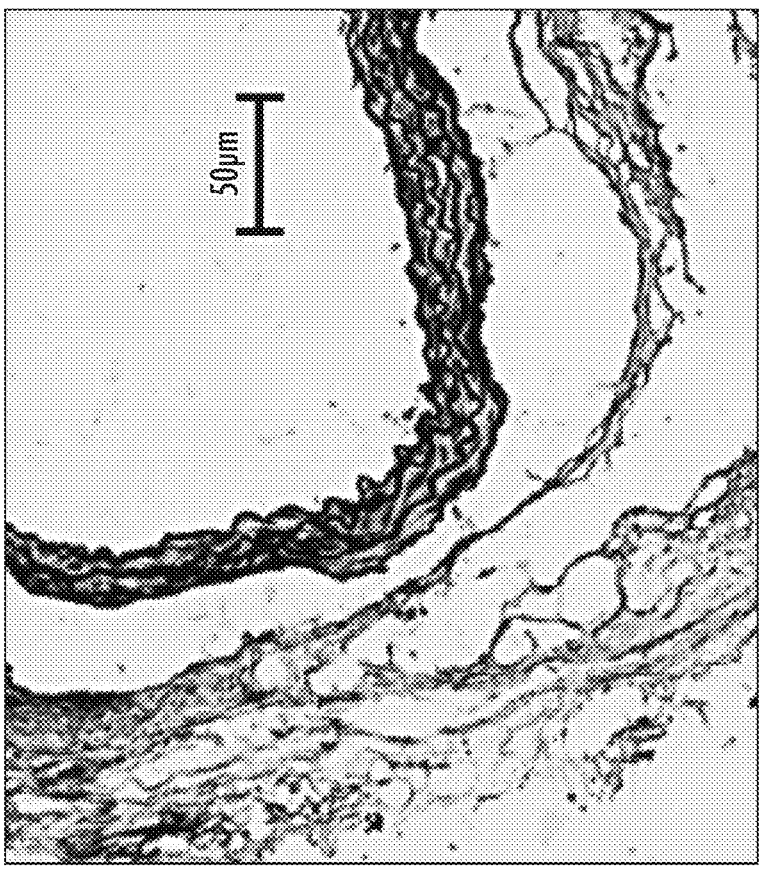
FIG. 40 illustrates histological analysis of aneurysmal aorta tagged with gold nanoparticles by use of antibodies as described herein.
Figure 40:
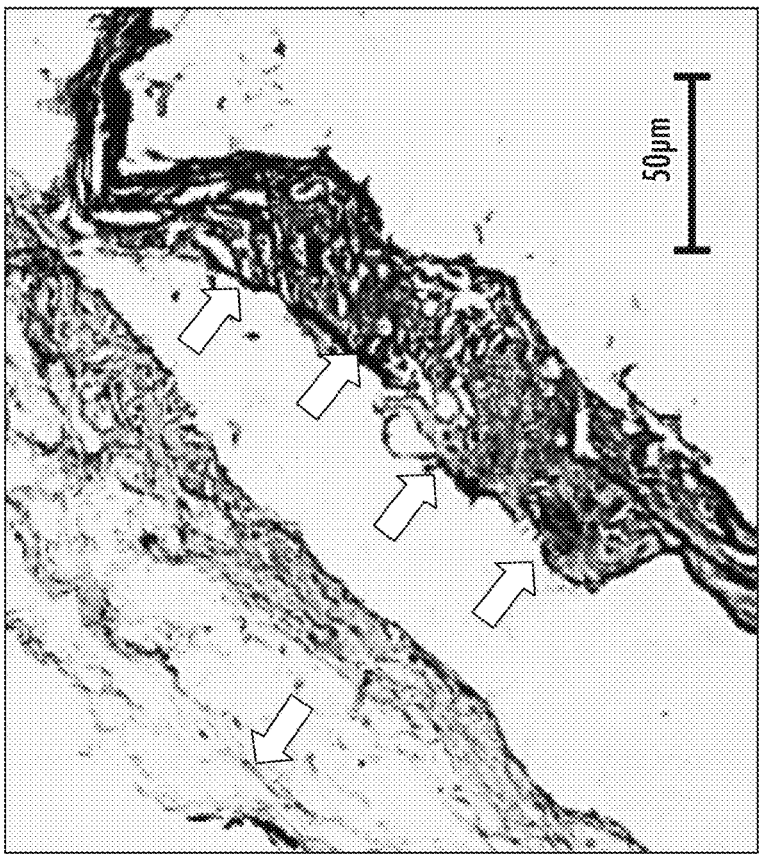

Cryosections of both aneurysms and healthy aortas were used for histological analysis (FIG. 40). Aortas were fixed in buffered formalin, embedded in optimal cutting temperature (OCT) compound (Sakura Finetek USA, Torrance, CA) after being washed in DI water and sectioned per standard procedures. Five-micrometer sections were mounted on positively charged glass slides. Slides were placed in 100% pre-cold acetone (Fisher Science Education, Nazareth, PA) for 10 minutes to adhere tissues to the slides. Subsequently, the slides were rinsed with tap water for 3 minutes to remove the OCT compound for further staining. Slides were stained with VVG to determine the elastin damage in different samples.

Figure 39:
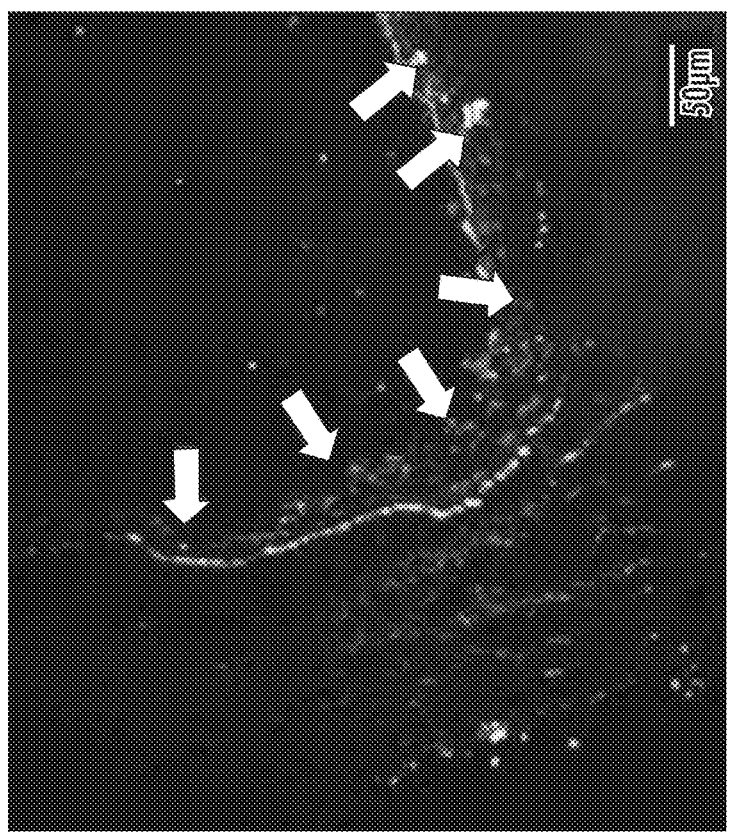
FIG. 39 provides two dark field microscopy images of aneurysmal aorta tagged with gold nanoparticles by use of antibodies as described herein.
Figure 39:
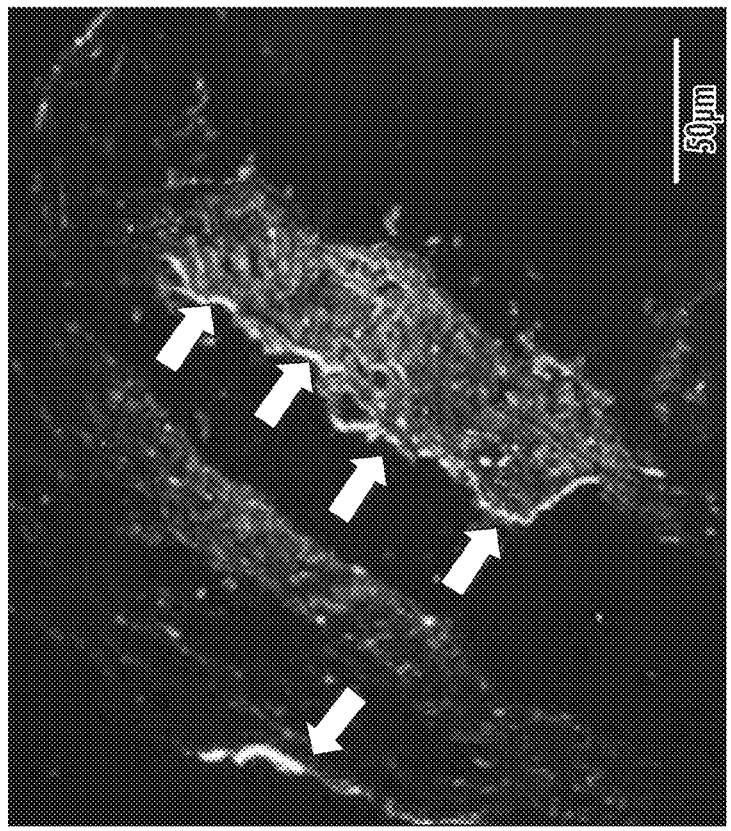

FIG. 39 and FIG. 40 present the dark field images (FIG. 39) and VVG stained images (FIG. 40) of two sections (left and right in the images) of aorta. As can be seen, a stronger dark field image signal is seen in the left image of FIG. 39, which showed more elastin damage (left, FIG. 40) as compared to the tissue section shown on the right of each figure, which contained mostly intact elastin fibers (right, FIG. 40). Signals given by the gold nanoparticles were found at positions where degraded elastin was exposed, indicated by the darker arrows in the images, while healthy and intact elastin fibers were devoid of GNP signal as indicated by the lighter arrows in the images.

Figure 41:
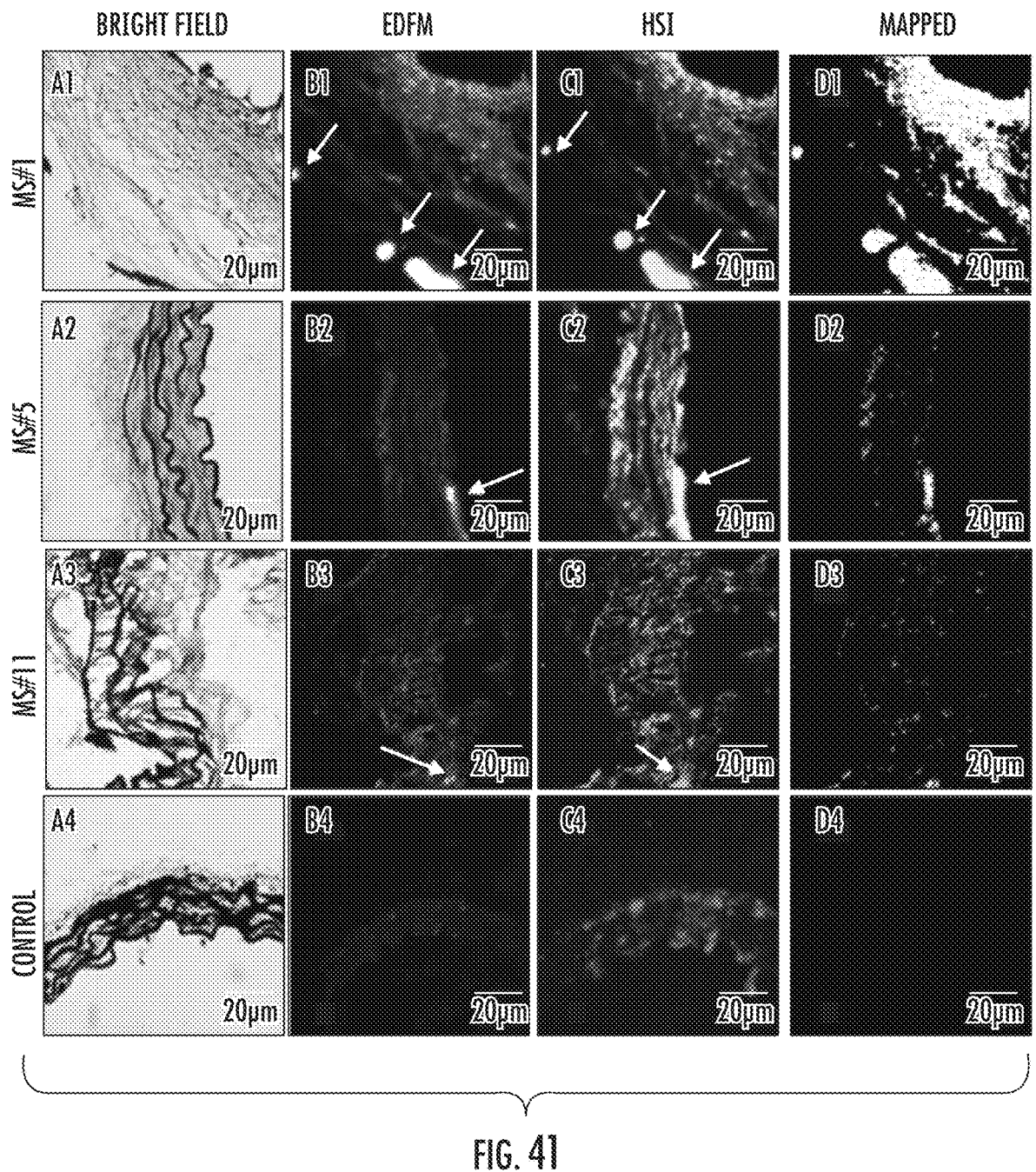
FIG. 41 provides hyperspectral mapping of suprarenal aorta tissue tagged with gold nanoparticles by use of antibodies as described herein. Images A1-A4 presents bright field microscopy images (40×) after VVG stain and demonstrated different elastin degradation level. Images B1-B4 presents enhanced darkfield microscopy (40×) images showing the presence of the high contrast EL-GNPs in the tissues as indicated by the arrows. Images C1-C4 includes hyperspectral images (40×). Images D1-D4 includes the hyperspectral images mapped against the respective reference spectrum library generated with negative controls.

FIG. 41 provides the results of the hyperspectral mapping of suprarenal aorta tissue tagged with gold nanoparticles by use of the antibody tagged EL-GNPs. The rows on FIG. 41, from top to bottom, correspond to suprarenal aortas with different levels of elastin damage within the aortic walls, from high to low, respectively. The first column (A) presents bright field microscopy images (40×) after VVG stain and demonstrated different elastin degradation level. The second column (B) presents enhanced darkfield microscopy (40×) images showing the presence of the high contrast EL-GNPs in the tissues as indicated by the arrows. The third column (C) includes hyperspectral images (40×) the fourth column (D) includes the hyperspectral images mapped against the respective reference spectrum library generated with negative controls. This identified a wider distribution of EL-GNPs as compared to the darkfield microscopy (FIG. 39). In addition, the mapped EL-GNPs quantity increased as the tissue showed more elastin damage.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. An antibody or antigen binding fragment thereof which binds to degraded elastin, the antibody or antigen binding fragment thereof comprising the amino acid sequence of SEQ ID NO: 9, SEQ ID NO: 11, SEQ ID NO: 13, SEQ ID NO: 27, SEQ ID NO: 29, and SEQ ID NO: 31.

2. The antibody or antigen binding fragment thereof of claim 1, wherein the antibody is a monoclonal antibody.

3. The antibody or antigen binding fragment thereof of claim 1, wherein the antibody is a polyclonal antibody.

4. The antibody or antigen binding fragment thereof of claim 1, wherein the antibody or antigen binding fragment thereof is an antibody that is a fully human antibody, a non-human antibody, a chimeric antibody, a humanized antibody, or a single domain antibody.

5. The antibody or antigen binding fragment thereof of claim 1, wherein the antibody or antigen binding fragment thereof is an antigen binding fragment that comprises a Fab, a Fab', a F(ab')2, a Fv, a disulfide linked Fv, or a scFv.

6. A composition comprising the antibody or antigen binding fragment thereof of claim 1 directly or indirectly operably linked to a secondary material.

7. The composition of claim 6, wherein the secondary material comprises a biologically active agent.

8. The composition of claim 7, wherein the biologically active agent comprises an anticoagulant, an antiplatelet, an anti-inflammatory, an SMC proliferation inhibitor, a matrix metalloproteinase inhibitor, a cathepsin inhibitor, a cytostatic agent, an anti-oxidant, a collagen stabilizing agent, an elastin-stabilizing agent, an elastin regeneration agent, a cytokine, an enzyme, a chemokine, a radioisotope, a toxin, an immunomodulatory agent, a chelator, a nucleic acid construct, a chemotherapeutic agent, an elastin crosslinking agent or a tropoelastin crosslinking agent.

9. The composition of claim 6, wherein the secondary material comprises an imaging agent.

10. The composition of claim 9, wherein the imaging agent comprises a photoactivatable agent, a fluorophore, a radioisotope, a bioluminescent peptide, a fluorescent tag, a fluorescent peptide, an affinity label, an enzymatic label, an MRI agent, a gold particle, an x-ray opaque substance, or an isotopic label.

11. The composition of claim 6, wherein the secondary material comprises a carrier.

12. The composition of claim 11, wherein the carrier comprises a liposome.

13. The composition of claim 11, wherein the carrier is a particle.

14. The composition of claim 13, wherein the particle is a nanoparticle.

15. The composition of claim 13, wherein the particle comprises a degradable polymer.

16. The antibody or antigen binding fragment thereof of claim 1, comprising the amino acid sequence of SEQ ID NO: 7.

17. The antibody or antigen binding fragment thereof of claim 1, comprising the amino acid sequence of SEQ ID NO: 25.

18. A method of binding to degraded elastin fiber comprising contacting a degraded elastic fiber with an antibody or antigen binding fragment thereof of claim 1, wherein the antibody or antigen binding fragment thereof is operably linked to a secondary material.

19. The method of claim 18, wherein the secondary material comprises a carrier and a biologically active agent incorporated into the carrier, wherein the biologically active agent is released from the carrier following the binding of the antibody or antigen binding fragment thereof to the degraded elastic fiber.

20. The method of claim 18, the secondary material comprising an imaging agent.

* * * * *

SEQUENCE LISTING

```
<160> NUMBER OF SEQ ID NOS: 41

<210> SEQ ID NO 1
<211> LENGTH: 17
<212> TYPE: PRT
<213> ORGANISM: Rattus sp.

<400> SEQUENCE: 1

Gly Ala Leu Gly Pro Gly Gly Lys Pro Pro Lys Pro Gly Ala Gly Leu
1               5                   10                  15

Leu

<210> SEQ ID NO 2
<211> LENGTH: 47
<212> TYPE: PRT
<213> ORGANISM: Rattus sp.

<400> SEQUENCE: 2

Leu Gly Tyr Pro Ile Lys Ala Pro Lys Leu Pro Gly Gly Tyr Gly Leu
1               5                   10                  15

Pro Tyr Thr Thr Gly Lys Leu Pro Tyr Gly Tyr Pro Gly Gly Val Ala
            20                  25                  30

Gly Ala Ala Gly Lys Ala Gly Tyr Pro Thr Thr Gly Thr Gly Val
            35                  40                  45

<210> SEQ ID NO 3
<211> LENGTH: 18
<212> TYPE: PRT
<213> ORGANISM: Unknown
<220> FEATURE:
<223> OTHER INFORMATION: Description of Unknown:
      Elastin sequence

<400> SEQUENCE: 3

Pro Gly Gly Tyr Gly Leu Pro Tyr Thr Thr Gly Lys Leu Pro Tyr Gly
1               5                   10                  15

Tyr Pro

<210> SEQ ID NO 4
<211> LENGTH: 1368
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 4

```
atggcttggg tgtggacctt gctattcctg atggcagctg cccaaagtgc ccaagcacag        60
atccagttgg agcagtctgg acctgagctg aagaagcctg agagacagt caagatctcc       120
tgcaaggctt ctgggtatac cttcagaaag tatggaatga gctgggtgaa gcaggctcca       180
ggaaaacatt taaagtggat gggctggata aacacctaca ctggaaagcc aacatatgct       240
gatgacttca agggacggtt tgccttctct ttgggaacct ctgccagcac tgcctatttg       300
cagatcaaca acctcagaaa tgaggacacg gctacatatt tctgtgcaag agaagactac       360
tggggccaag gcaccactct cacagtctcc tcagccaaaa cgacaccccc atctgtctat       420
ccactggccc ctggatctgc tgcccaaact aactccatgg tgaccctggg atgcctggtc       480
aagggctatt tccctgagcc agtgacagtg acctggaact ctggatccct gtccagcggt       540
gtgcacacct tcccagctgt cctgcagtct gacctctaca ctctgagcag ctcagtgact       600
gtcccctcca gcacctggcc cagcgagacc gtcacctgca acgttgccca ccggccagc       660
agcaccaagg tggacaagaa aattgtgccc agggattgtg gttgtaagcc ttgcatatgt       720
acagtcccag aagtatcatc tgtcttcatc ttcccccaa agcccaagga tgtgctcacc       780
attactctga ctcctaaggt cacgtgtgtt gtggtagaca tcagcaagga tgatcccgag       840
gtccagttca gctggtttgt agatgatgtg gaggtgcaca cagctcagac gcaaccccgg       900
gaggagcagt tcaacagcac tttccgctca gtcagtgaac ttcccatcat gcaccaggac       960
tggctcaatg gcaaggagtt caatgcagg gtcaacagtg cagctttccc tgcccccatc      1020
gagaaaacca tctccaaaac caaggcaga ccgaaggctc acaggtgta caccattcca       1080
cctcccaagg agcagatggc aaggataaa gtcagtctga cctgcatgat aacagacttc      1140
ttccctgaag acattactgt ggagtggcag tggaatgggc agccagcgga gaactacaag      1200
aacactcagc ccatcatgga cacagatggc tcttacttcg tctacagcaa gctcaatgtg      1260
cagaagagca actgggaggc aggaaatact ttcacctgct ctgtgttaca tgagggcctg      1320
cacaaccacc atactgagaa gagcctctcc cactctcctg gtaaatga                    1368
```

<210> SEQ ID NO 5
<211> LENGTH: 455
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Met Ala Trp Val Trp Thr Leu Leu Phe Leu Met Ala Ala Ala Gln Ser
1               5                   10                  15

Ala Gln Ala Gln Ile Gln Leu Glu Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Arg Lys Tyr Gly Met Ser Trp Val Lys Gln Ala Pro Gly Lys His Leu
    50                  55                  60

Lys Trp Met Gly Trp Ile Asn Thr Tyr Thr Gly Lys Pro Thr Tyr Ala
65                  70                  75                  80

Asp Asp Phe Lys Gly Arg Phe Ala Phe Ser Leu Gly Thr Ser Ala Ser
                85                  90                  95
```

Thr Ala Tyr Leu Gln Ile Asn Ser Leu Arg Asn Glu Asp Thr Ala Thr
                100                 105                 110

Tyr Phe Cys Ala Arg Glu Asp Tyr Trp Gly Gln Gly Thr Thr Leu Thr
            115                 120                 125

Val Ser Ser Ala Lys Thr Thr Pro Pro Ser Val Tyr Pro Leu Ala Pro
130                 135                 140

Gly Ser Ala Ala Gln Thr Asn Ser Met Val Thr Leu Gly Cys Leu Val
145                 150                 155                 160

Lys Gly Tyr Phe Pro Glu Pro Val Thr Val Thr Trp Asn Ser Gly Ser
                165                 170                 175

Leu Ser Ser Gly Val His Thr Phe Pro Ala Val Leu Gln Ser Asp Leu
            180                 185                 190

Tyr Thr Leu Ser Ser Ser Val Thr Val Pro Ser Ser Thr Trp Pro Ser
        195                 200                 205

Glu Thr Val Thr Cys Asn Val Ala His Pro Ala Ser Ser Thr Lys Val
210                 215                 220

Asp Lys Lys Ile Val Pro Arg Asp Cys Gly Cys Lys Pro Cys Ile Cys
225                 230                 235                 240

Thr Val Pro Glu Val Ser Ser Val Phe Ile Phe Pro Pro Lys Pro Lys
                245                 250                 255

Asp Val Leu Thr Ile Thr Leu Thr Pro Lys Val Thr Cys Val Val Val
            260                 265                 270

Asp Ile Ser Lys Asp Asp Pro Glu Val Gln Phe Ser Trp Phe Val Asp
        275                 280                 285

Asp Val Glu Val His Thr Ala Gln Thr Gln Pro Arg Glu Glu Gln Phe
290                 295                 300

Asn Ser Thr Phe Arg Ser Val Ser Glu Leu Pro Ile Met His Gln Asp
305                 310                 315                 320

Trp Leu Asn Gly Lys Glu Phe Lys Cys Arg Val Asn Ser Ala Ala Phe
                325                 330                 335

Pro Ala Pro Ile Glu Lys Thr Ile Ser Lys Thr Lys Gly Arg Pro Lys
            340                 345                 350

Ala Pro Gln Val Tyr Thr Ile Pro Pro Lys Glu Gln Met Ala Lys
        355                 360                 365

Asp Lys Val Ser Leu Thr Cys Met Ile Thr Asp Phe Phe Pro Glu Asp
370                 375                 380

Ile Thr Val Glu Trp Gln Trp Asn Gly Gln Pro Ala Glu Asn Tyr Lys
385                 390                 395                 400

Asn Thr Gln Pro Ile Met Asp Thr Asp Gly Ser Tyr Phe Val Tyr Ser
                405                 410                 415

Lys Leu Asn Val Gln Lys Ser Asn Trp Glu Ala Gly Asn Thr Phe Thr
            420                 425                 430

Cys Ser Val Leu His Glu Gly Leu His Asn His His Thr Glu Lys Ser
        435                 440                 445

Leu Ser His Ser Pro Gly Lys
        450                 455

<210> SEQ ID NO 6
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
cagatccagt tggagcagtc tggacctgag ctgaagaagc ctggagagac agtcaagatc    60
tcctgcaagg cttctgggta taccttcaga aagtatggaa tgagctgggt gaagcaggct   120
ccaggaaaac atttaaagtg gatgggctgg ataaacacct acactggaaa gccaacatat   180
gctgatgact caagggacg gtttgccttc tctttgggaa cctctgccag cactgcctat   240
ttgcagatca caacctcag aaatgaggac acggctacat atttctgtgc aagagaagac   300
tactggggcc aaggcaccac tctcacagtc tcctca                            336
```

<210> SEQ ID NO 7
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Gln Ile Gln Leu Glu Gln Ser Gly Pro Glu Leu Lys Lys Pro Gly Glu
1               5                   10                  15

Thr Val Lys Ile Ser Cys Lys Ala Ser Gly Tyr Thr Phe Arg Lys Tyr
            20                  25                  30

Gly Met Ser Trp Val Lys Gln Ala Pro Gly Lys His Leu Lys Trp Met
        35                  40                  45

Gly Trp Ile Asn Thr Tyr Thr Gly Lys Pro Thr Tyr Ala Asp Asp Phe
    50                  55                  60

Lys Gly Arg Phe Ala Phe Ser Leu Gly Thr Ser Ala Ser Thr Ala Tyr
65                  70                  75                  80

Leu Gln Ile Asn Asn Leu Arg Asn Glu Asp Thr Ala Thr Tyr Phe Cys
                85                  90                  95

Ala Arg Glu Asp Tyr Trp Gly Gln Gly Thr Thr Leu Thr Val Ser Ser
            100                 105                 110
```

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
aagtatggaa tgagc                                                    15
```

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

```
Lys Tyr Gly Met Ser
1               5
```

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 10
tggataaaca cctacactgg aaagccaaca tatgctgatg acttcaaggg a          51

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Trp Ile Asn Thr Tyr Thr Gly Lys Pro Thr Tyr Ala Asp Asp Phe Lys
1               5                   10                  15

Gly

<210> SEQ ID NO 12
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12 gaagactac                                                          9

<210> SEQ ID NO 13
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Asp Tyr
1

<210> SEQ ID NO 14
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cagatccagt tggagcagtc tggacctgag ctgaagaagc ctggagagac agtcaagatc   60
tcctgcaagg cttctgggta taccttcaga                                   90

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Ile Gln Leu Glu Gln Ser Gly Pro Glu Leu Lys Lys Pro Gly Glu
1               5                   10                  15

Thr Val Lys Ile Ser Cys Lys Ala Ser Gly Tyr Thr Phe Arg

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tgggtgaagc aggctccagg aaaacattta aagtggatgg gc                            42

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Trp Val Lys Gln Ala Pro Gly Lys His Leu Lys Trp Met Gly
1               5                   10

<210> SEQ ID NO 18
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cggtttgcct tctctttggg aacctctgcc agcactgcct atttgcagat caacaacctc        60
agaaatgagg acacggctac atatttctgt gcaaga                                   96

<210> SEQ ID NO 19
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Arg Phe Ala Phe Ser Leu Gly Thr Ser Ala Ser Thr Ala Tyr Leu Gln
1               5                   10                  15

Ile Asn Asn Leu Arg Asn Glu Asp Thr Ala Thr Tyr Phe Cys Ala Arg
            20                  25                  30

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tggggccaag gcaccactct cacagtctcc tca                                      33

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Trp Gly Gln Gly Thr Thr Leu Thr Val Ser Ser
1               5                   10

<210> SEQ ID NO 22
<211> LENGTH: 717
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
atgagtcctg cccagttcct gtttctgtta gtgctctgga ttcgggaaac caacggtgat    60
gttgtgatga cccagactcc actcactttg tcggttacca ttggacaacc agcctccatc   120
tcttgcaagt caggtcagag cctcttaaat agtgatggaa agacatattt gaattggttg   180
ttacagcggc caggccagtc tccaaagcgc ctaatctatc tggtgtctaa actggactct   240
ggagtccctg acaggttcac tggcagtgga tcagggacag atttcacact aaaaatcagc   300
agagtggagg ctgaggattt gggagtttat tattgctggc aaggtacaca ttttccgtgg   360
acgttcggtg gaggcaccaa gctggaaatc aaacgggctg atgctgcacc aactgtatcc   420
atcttcccac catccagtga gcagttaaca tctggaggtg cctcagtcgt gtgcttcttg   480
aacaacttct accccaaaga catcaatgtc aagtggaaga ttgatggcag tgaacgacaa   540
aatggcgtcc tgaacagttg gactgatcag gacagcaaag acagcaccta cagcatgagc   600
agcaccctca cgttgaccaa ggacgagtat aacgcacata cagctatac ctgtgaggcc    660
actcacaaga catcaacttc acccattgtc aagagcttca caggaatga gtgttag      717
```

<210> SEQ ID NO 23
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

Met Ser Pro Ala Gln Phe Leu Phe Leu Leu Val Leu Trp Ile Arg Glu
1               5                   10                  15

Thr Asn Gly Asp Val Val Met Thr Gln Thr Pro Leu Thr Leu Ser Val
                20                  25                  30

Thr Ile Gly Gln Pro Ala Ser Ile Ser Cys Lys Ser Gly Gln Ser Leu
            35                  40                  45

Leu Asn Ser Asp Gly Lys Thr Tyr Leu Asn Trp Leu Leu Gln Arg Pro
        50                  55                  60

Gly Gln Ser Pro Lys Arg Leu Ile Tyr Leu Val Ser Lys Leu Asp Ser
65                  70                  75                  80

Gly Val Pro Asp Arg Phe Thr Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Trp Gln Gly Thr His Phe Pro Trp Thr Phe Gly Gly Gly Thr Lys Leu
        115                 120                 125

```
Glu Ile Lys Arg Ala Asp Ala Ala Pro Thr Val Ser Ile Phe Pro Pro
            130                 135                 140
Ser Ser Glu Gln Leu Thr Ser Gly Gly Ala Ser Val Val Cys Phe Leu
145                 150                 155                 160
Asn Asn Phe Tyr Pro Lys Asp Ile Asn Val Lys Trp Lys Ile Asp Gly
                165                 170                 175
Ser Glu Arg Gln Asn Gly Val Leu Asn Ser Trp Thr Asp Gln Asp Ser
                180                 185                 190
Lys Asp Ser Thr Tyr Ser Met Ser Ser Thr Leu Thr Leu Thr Lys Asp
                195                 200                 205
Glu Tyr Glu Arg His Asn Ser Tyr Thr Cys Glu Ala Thr His Lys Thr
            210                 215                 220
Ser Thr Ser Pro Ile Val Lys Ser Phe Asn Arg Asn Glu
225                 230                 235
```

<210> SEQ ID NO 24
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
gatgttgtga tgacccagac tccactcact ttgtcggtta ccattggaca accagcctcc    60
atctcttgca agtcaggtca gagcctctta aatagtgatg gaaagacata tttgaattgg   120
ttgttacagc ggccaggcca gtctccaaag cgcctaatct atctggtgtc taaactggac   180
tctggagtcc ctgacaggtt cactggcagt ggatcaggga cagatttcac actaaaaatc   240
agcagagtgg aggctgagga tttgggagtt tattattgct ggcaaggtac acattttccg   300
tggacgttcg gtggaggcac caagctggaa atcaaa                             336
```

<210> SEQ ID NO 25
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Asp Val Val Met Thr Gln Thr Pro Leu Thr Leu Ser Val Thr Ile Gly
1               5                   10                  15
Gln Pro Ala Ser Ile Ser Cys Lys Ser Gly Gln Ser Leu Leu Asn Ser
            20                  25                  30
Asp Gly Lys Thr Tyr Leu Asn Trp Leu Leu Gln Arg Pro Gly Gln Ser
        35                  40                  45
Pro Lys Arg Leu Ile Tyr Leu Val Ser Lys Leu Asp Ser Gly Val Pro
    50                  55                  60
Asp Arg Phe Thr Gly Ser Gly Ser Gly Thr Asp Phe Thr Leu Lys Ile
65                  70                  75                  80
Ser Arg Val Glu Ala Glu Asp Leu Gly Val Tyr Tyr Cys Trp Gln Gly
                85                  90                  95
Thr His Phe Pro Trp Thr Phe Gly Gly Gly Thr Lys Leu Glu Ile Lys
            100                 105                 110
```

<210> SEQ ID NO 26
<211> LENGTH: 48

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aagtcaggtc agagcctctt aaatagtgat ggaaagacat atttgaat          48

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Ser Gly Gln Ser Leu Leu Asn Ser Asp Gly Lys Thr Tyr Leu Asn
1               5                   10                  15

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ctggtgtcta aactggactc t                                       21

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Val Ser Lys Leu Asp Ser
1               5

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tggcaaggta cacattttcc gtggacg                                 27

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Trp Gln Gly Thr His Phe Pro Trp Thr
1               5
```

<210> SEQ ID NO 32
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gatgttgtga tgacccagac tccactcact ttgtcggtta ccattggaca accagcctcc    60
atctcttgc                                                            69

<210> SEQ ID NO 33
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Val Val Met Thr Gln Thr Pro Leu Thr Leu Ser Val Thr Ile Gly
1               5                   10                  15

Gln Pro Ala Ser Ile Ser Cys
            20

<210> SEQ ID NO 34
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tggttgttac agcggccagg ccagtctcca aagcgcctaa tctat                    45

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Trp Leu Leu Gln Arg Pro Gly Gln Ser Pro Lys Arg Leu Ile Tyr
1               5                   10                  15

<210> SEQ ID NO 36
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ggagtccctg acaggttcac tggcagtgga tcagggacag atttcacact aaaaatcagc    60
agagtggagg ctgaggattt gggagtttat tattg                               95

<210> SEQ ID NO 37
<211> LENGTH: 32
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 37

Gly Val Pro Asp Arg Phe Thr Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ttcggtggag gcaccaagct ggaaatcaaa                                    30

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Phe Gly Gly Gly Thr Lys Leu Glu Ile Lys
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Ala Arg Glu Asp Tyr Trp
1               5

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Cys Trp Gln Gly Thr His Phe Pro Trp Thr Phe
1               5                   10
```